US012698306B2

(12) United States Patent
Slusher et al.

(10) Patent No.: US 12,698,306 B2
(45) Date of Patent: Aug. 4, 2026

(54) BILE ACID-GCPII INHIBITOR CONJUGATES TO TREAT INFLAMMATORY DISEASES, INCLUDING INFLAMMATORY BOWEL DISEASE (IBD)

(71) Applicants: The Johns Hopkins University, Baltimore, MD (US); INSTITUTE OF ORGANIC CHEMISTRY & BIOCHEMISTRY AV CR V.V.I., Prague (CZ)

(72) Inventors: Barbara Slusher, Baltimore, MD (US); Diane E. Peters, Baltimore, MD (US); Rana Rais, Baltimore, MD (US); Pavel Majer, Prague (CZ); Lukas Tenora, Prague (CZ); Ivan Snajdr, Prague (CZ)

(73) Assignees: The Johns Hopkins University, Baltimore, MD (US); Institute of Organic Chemistry & Biochemistry as CR V.V.I., Prague (CZ)

( * ) Notice: Subject to any disclaimer, the term of this patent is extended or adjusted under 35 U.S.C. 154(b) by 845 days.

(21) Appl. No.: 17/795,426

(22) PCT Filed: Jan. 29, 2021

(86) PCT No.: PCT/US2021/015732

§ 371 (c)(1),
(2) Date: Jul. 26, 2022

(87) PCT Pub. No.: WO2021/155167

PCT Pub. Date: Aug. 5, 2021

(65) Prior Publication Data

US 2023/0128984 A1 Apr. 27, 2023

Related U.S. Application Data

(60) Provisional application No. 62/968,602, filed on Jan. 31, 2020.

(51) Int. Cl.

| | |
|---|---|
| ***C07J 51/00*** | (2006.01) |
| ***A61P 29/00*** | (2006.01) |
| ***C07J 33/00*** | (2006.01) |
| ***C07J 41/00*** | (2006.01) |

(52) U.S. Cl.

CPC ............... *C07J 51/00* (2013.01); *A61P 29/00* (2018.01); *C07J 33/002* (2013.01); *C07J 41/0055* (2013.01)

(58) Field of Classification Search

CPC ...... C07J 51/00; C07J 33/002; C07J 41/0055; C07J 41/0033; C07F 9/005

See application file for complete search history.

(56) References Cited

U.S. PATENT DOCUMENTS

| | | | |
|---|---|---|---|
| 9,220,265 | B2 | 12/2015 | Hoekstra et al. |
| 10,105,415 | B2 | 10/2018 | Heslet et al. |
| 10,172,921 | B2 | 1/2019 | Couvineau et al. |
| 2011/0064657 | A1 | 3/2011 | Pomper et al. |
| 2016/0095921 | A1 | 4/2016 | Ebsworth et al. |
| 2016/0289262 | A1 | 10/2016 | Wang et al. |
| 2018/0180630 | A1 | 6/2018 | Monteleone |

FOREIGN PATENT DOCUMENTS

| | | | |
|---|---|---|---|
| JP | H0995496 | A | 4/1997 |
| JP | 2010517931 | A | 5/2010 |
| JP | 2017533923 | A | 11/2017 |
| JP | 2017535570 | A | 11/2017 |
| JP | 2017536379 | A | 12/2017 |
| JP | 2020525426 | A | 8/2020 |
| WO | WO 2002/092553 | | 11/2002 |
| WO | WO 2004/078742 | | 9/2004 |
| WO | WO 2016/022809 | | 2/2016 |
| WO | WO 2016/022827 | | 2/2016 |

OTHER PUBLICATIONS

Fini et al. (Archiv der Pharmazie, 320(10), 1014-1019). (Year: 1987).*
O'Brien (Polymer Engineering and Science, 29(13), 846-849). (Year: 1989).*
Extended EP Search Report for EP21747380.0, mailed Mar. 7, 2024, 5 pages.
Wu et al., Phosphoramidate derivatives of hydroxysteroids as inhibitors of prostate-specific membrane antigen. Bioorganic & Medicinal Chemistry Letters, vol. 18, No. 1, Oct. 30, 2007, pp. 281-284.
International Search Report and Written Opinion for PCT/US2021/015732. Mailed Apr. 15, 2021. 10 pages.
Baldwin et al., Neuroinflammation triggered by ß-glucan/dectin-1 signaling enables CNS axon regeneration. Proc Natl Acad Sci U S A. Feb. 24, 2015;112(8):2581-6.
Berge et al., Pharmaceutical salts. J Pharm Sci. Jan. 1977;66(1):1-19.
Calmus et al., Shaping macrophages function and innate immunity by bile acids: mechanisms and implication in cholestatic liver diseases. Clin Res Hepatol Gastroenterol. Oct. 2014;38(5):550-6.
Colombel et al., Adalimumab for maintenance of clinical response and remission in patients with Crohn's disease: the CHARM trial. Gastroenterology. Jan. 2007;132(1):52-65.
Coskun et al., Novel Targeted Therapies for Inflammatory Bowel Disease. Trends Pharmacol Sci. Feb. 2017;38(2):127-142.
Ferraris et al., Structure-Activity Relationships of Glutamate Carboxypeptidase II (GCPII) Inhibitors. Current Medicinal Chemistry, 2012, 19(9), 1282-1294.
Greene et al., Protective Groups in Organic Synthesis, 3rd ed. John Wiley & Sons. 1999. TOC only. 3 pages.

(Continued)

*Primary Examiner* — Susanna Moore
(74) *Attorney, Agent, or Firm* — Casimir Jones, SC; Jeffrey W. Childers

(57) ABSTRACT

GCPII inhibitors comprising 2-(phosphonomethyl) pentanedioic acid (2-PMPA) conjugated to a bile acid and their use for treating a disease or condition associated with elevated levels of GCPII, including inflammatory bowel disease.

6 Claims, 11 Drawing Sheets

(56) References Cited

OTHER PUBLICATIONS

Hamilton et al., Update on biologic pathways in inflammatory bowel disease and their therapeutic relevance. J Gastroenterol. Jan. 2012;47(1):1-8.
Hanauer et al., Maintenance infliximab for Crohn's disease: the Accent I randomised trial. Lancet. May 4, 2002;359(9317):1541-9.
Hazra et al., Bile acid amides derived from chiral amino alcohols: novel antimicrobials and antifungals. Bioorg Med Chem Lett. Feb. 9, 2004;14(3):773-7.
Ho et al., Obeticholic acid, a synthetic bile acid agonist of the farnesoid X receptor, attenuates experimental autoimmune encephalomyelitis. Proc Natl Acad Sci U S A. Feb. 9, 2016;113(6):1600-5.
Jackson et al., Design and pharmacological activity of phosphinic acid based NAALADase inhibitors. J Med Chem. Nov. 22, 2001;44(24):4170-5.
Jackson et al., Design, synthesis, and biological activity of a potent inhibitor of the neuropeptidase N-acetylated alpha-linked acidic dipeptidase. J Med Chem. Jan. 19, 1996;39(2):619-22.
Kaser et al., Inflammatory bowel disease. Annu Rev Immunol. 2010;28:573-621.
Kozuch et al., Treatment of inflammatory bowel disease: a review of medical therapy. World J Gastroenterol. Jan. 21, 2008;14(3):354-77.
Kuehne et al., Steroidal Dihydro-1,3-Oxazines as Antitumor Agents. J Med Pharm Chem. Mar. 1962;5:281-96.
Kull et al., Mixturs of quaternary ammonium compounds and long-chain fatty acids as antifungal agents. Appl Microbiol. Nov. 1961;9(6):538-41.
Laukens et al., Tauroursodeoxycholic acid inhibits experimental colitis by preventing early intestinal epithelial cell death. Lab Invest. Dec. 2014;94(12):1419-30.
Lawrance. What is left when anti-tumour necrosis factor therapy in inflammatory bowel diseases fails? World J Gastroenterol. Feb. 7, 2014;20(5):1248-58.
Li et al., Synthesis, Anticancer Activities, Antimicrobial Activities and Bioavailability of Berberine-Bile Acid Analogues. Lett. Drug Des. Discov. 2012, 9(6), 573-580.
Mesters et al, Structure of glutamate carboxypeptidase II, a drug target in neuronal damage and prostate cancer. The EMBO Journal. 2006;25,1375-1384.
Mostarda et al., Glucuronidation of bile acids under flow conditions: design of experiments and Koenigs-Knorr reaction optimization. Org Biomol Chem. Dec. 21, 2014;12(47):9592-600.
Nedelcovych et al., Enhanced Brain Delivery of 2-(Phosphonomethyl)pentanedioic Acid Following Intranasal Administration of Its γ-Substituted Ester Prodrugs. Mol Pharm. Oct. 2, 2017;14(10):3248-3257.
Nedelcovych et al., Glutamine Antagonist JHU083 Normalizes Aberrant Glutamate Production and Cognitive Deficits in the EcoHIV Murine Model of HIV-Associated Neurocognitive Disorders. J Neuroimmune Pharmacol. Sep. 2019;14(3):391-400.
Pellicciari et al., Bile acid derivatives as ligands of the farnesoid X receptor. Synthesis, evaluation, and structure-activity relationship of a series of body and side chain modified analogues of chenodeoxycholic acid. J Med Chem. Aug. 26, 2004;47(18):4559-69.
Rais et al., FOLH1/GCPII is elevated in IBD patients, and its inhibition ameliorates murine IBD abnormalities. JCI Insight. Aug. 4, 2016;1(12):e88634. 11 pages.
Regueiro et al., Infliximab dose intensification in Crohn's disease. Inflamm Bowel Dis. Sep. 2007;13(9):1093-9.
Robinson et al., Hydrolysis of the brain dipeptide N-acetyl-L-aspartyl-L-glutamate. Identification and characterization of a novel N-acetylated alpha-linked acidic dipeptidase activity from rat brain. J Biol Chem. Oct. 25, 1987;262(30):14498-506.
Rojas et al., Kinetics and inhibition of glutamate carboxypeptidase II using a microplate assay. Anal Biochem. Nov. 1, 2002;310(1):50-4.
Rubin and Farber, Pathology. J.B. Lippincott Company. 1994. TOC only. 4 pages.
Sartor et al., Mechanisms of disease: pathogenesis of Crohn's disease and ulcerative colitis. Nat Clin Pract Gastroenterol Hepatol. Jul. 2006;3(7):390-407.
Schmidt et al., Predictive value of mucosal TNF-alpha transcripts in steroid-refractory Crohn's disease patients receiving intensive immunosuppressive therapy. Inflamm Bowel Dis. Jan. 2007;13(1):65-70.
Schreiber et al., Maintenance therapy with certolizumab pegol for Crohn's disease. N Engl J Med. Jul. 19, 2007;357(3):239-50.
Sievanen. Exploitation of Bile Acid Transport Systems in Prodrug Design. Molecules, 2007, 12, 1859-1889.
Sipka et al., The immunomodulatory role of bile acids. Int Arch Allergy Immunol. 2014;165(1):1-8.
Slusher et al, Glutamate Carboxypeptidase II. Handbook of Proteolytic Enzymes vol. 2, 2013, pp. 1620-1627.
Strober et al., The fundamental basis of inflammatory bowel disease. J Clin Invest. Mar. 2007;117(3):514-21.
Tang et al., Prostate targeting ligands based on N-acetylated alpha-linked acidic dipeptidase. Biochem Biophys Res Commun. Jul. 18, 2003;307(1):8-14.
Van Assche et al., Progressive multifocal leukoencephalopathy after natalizumab therapy for Crohn's disease. N Engl J Med. Jul. 28, 2005;353(4):362-8.
Vitharana et al., Synthesis and biological evaluation of (R)- and (S)-2-(phosphonomethyl)pentanedioic acids as inhibitors of glutamate carboxypeptidase II., Tetrahedron: Asymmetry., 2002; vol. 13(15), pp. 1609-1614.
Xavier et al., Unravelling the pathogenesis of inflammatory bowel disease. Nature. Jul. 26, 2007;448(7152):427-34.
Yadav et al., Inflammatory bowel disease: exploring gut pathophysiology for novel therapeutic targets. Transl Res. Oct. 2016;176:38-68.

* cited by examiner

| Test compound | Dosage (mg/kg) | $C_{max}$ (nmol/mL) | $T_{max}$ (h) | $AUC_{last}$ (h*nmol/mL) | $C_0$ (nmol/ml) | Bioavailability |
|---|---|---|---|---|---|---|
| LTP-592 | 13.75 (5 mg eqv); IV | 31.67 | 0.08 | 9.93 | 91.75 | -- |
| LTP-592 | 45.83 (16.67 mg eqv); PO | 0.40 | 0.08 | 0.12 | -- | ~1% |

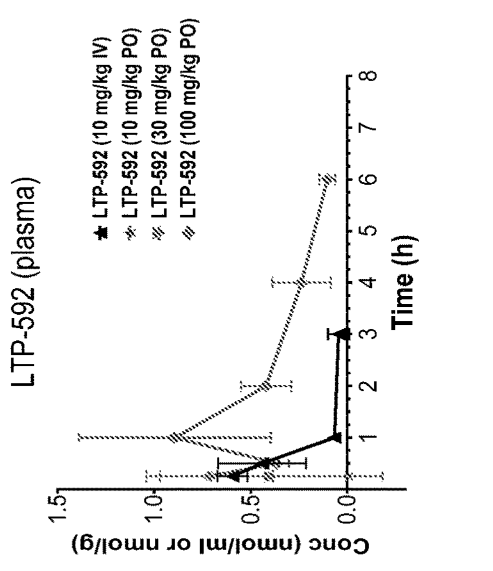
*Fig. 7A*
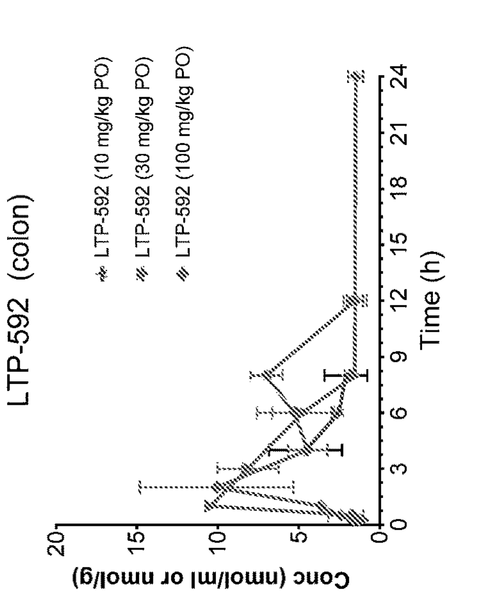
*Fig. 7B*
| Test compound | Dosage (mg/kg) | $C_{max}$ (nmol/mL or nmol/g) | $T_{max}$ (h) | $AUC_{last}$ (h*nmol/mL) |
|---|---|---|---|---|
| PLASMA PHARMACOKINETICS | | | | |
| LTP-592 | 10; IV | 0.59 ± 0.04 | 0.25 | 0.53 |
| LTP-592 | 100; PO | 0.89 ± 0.15 | 1 | 3.15 |
| COLON PHARMACOKINETICS | | | | |
| LTP-592 | 10; PO | 4.58 ± 2.26 | 4 | 20.5 |
| LTP-592 | 30; PO | 10.44 ± 0.23 | 1 | 53.66 |
| LTP-592 | 100; PO | 10.58 ± 4.74 | 2 | 80.57 |
*Fig. 7C*

BILE ACID-GCPII INHIBITOR CONJUGATES TO TREAT INFLAMMATORY DISEASES, INCLUDING INFLAMMATORY BOWEL DISEASE (IBD)

BACKGROUND

The folate hydrolase (FOLH1) gene encodes Glutamate Carboxypeptidase II (GCPII), an enzyme that is highly overexpressed in human inflammatory diseases, including inflammatory bowel disease (IBD). It has previously been shown that GCPII enzymatic function is elevated between about 300% to about 3000% in human IBD and that inhibiting GCPII activity using small molecule drugs in IBD mouse models causes significant disease improvement. Rais et al., 2016.

IBD is an idiopathic, chronic and frequently disabling inflammatory disorder of the intestine, which has two subtypes: Crohn's disease (CD) and ulcerative colitis (UC), each accounting for approximately 50% of IBD patients (Xavier and Podolsky, 2007; Srober et al, 2007; Sartor, 2006). IBD is a widespread G1 disease, with a prevalence of approximately 0.2% in the Western population. In the United States alone, 1.4 million patients are diagnosed IBD patients, resulting in enormous suffering and health-care costs.

IBD is a complex multifactorial disease with both genetic and environmental contributions, the interaction of which leads to IBD (Xavier and Podolsky; Strober et al, 2007; Sartor, 2006; Kaser et al., 2010). Unfortunately, the etiology of this mucosal dysregulation in UC and CD remain elusive (Kaser et al., 2010). Despite increasing therapeutic options available for the management of IBD, approximately one-third of IBD patients do not respond to any given therapy, and there is no cure for IBD (Hamilton et al, 2012). Anti-tumor necrosis factor (TNF)-based therapies, such as infliximab (IFX), adalimumab and certolizumab pegol, are currently the most effective therapies for severe UC and CD (Hanauer et al, 2002; Kozuch and Hanauer, 2008; Colombel et al, 2007; Schreiber et al, 2007). One-third of patients with CD, however, do not respond to anti-TNF therapies and another third lose responsiveness within six months of initiating therapy (Regueiro et al., 2007; Lawrance, 2014). These non-responders have more aggressive mucosal immune responses and additional treatments are indicated (Schmidt et al, 2007). Patients with extensive disease or who are at risk for short gut syndrome due to prior resections are usually poor surgical candidates. Currently, the only approved medication for patients who have failed an anti-TNF agent is natalizumab. Natalizumab, however, has been associated with several cases of progressive and often fatal multifocal leukoencephalopathy (PML) (Van et al, 2005). These shortcomings and complications associated with current treatment regimens emphasize the significance of exploring and identifying new and more effective therapies in patients with IBD.

SUMMARY

The presently disclosed subject matter provides a conjugate of 2-(phosphonomethyl) pentanedioic acid (2-PMPA), or a derivative thereof, and a bile acid, or derivative thereof.

In some aspects, the conjugate comprises a compound of formula (I):

(I)

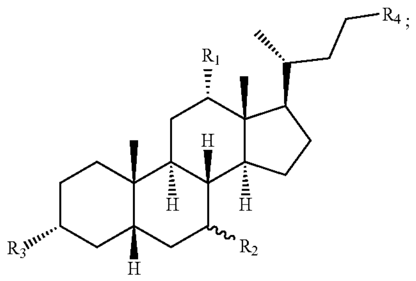

wherein $R_1$ and $R_2$ are each independently H or —OH; and wherein $R_3$ is OH and $R_4$ is selected from the group consisting of —NH—$X_1$, —COO—$X_1$, —C(═O)—NH—$CH_2$—C(═O)—O—$X_1$, and —C(═O)—NH—$CH_2$—$CH_2$—S(═O)$_2$—O—$X_1$, wherein $X_1$ is selected from the group consisting of —(C═O)—$(CH_2)_m$—P(═O)(OH)—$X_2$, —(C═O)—$(CH_2)_m$—CH(COOH)—$CH_2$—P(═O)(OH)—$X_2$, —$CH_2$—O—(C═O)—$(CH_2)_m$—P(═O)(OH)—$X_2$, —$CH_2$—O—C(═O)—$(CH_2)_m$—CH(COOH)—$CH_2$—P(═O)(OH)—$X_2$, —$CH_2$—O—C(═O)—$(CH_2)_m$—CH(COOH)—NH—(C═O)—NH—CH(COOH)—$CH_2$—CH$(CH_3)_2$, —$CH_2$—O—C(═O)—Ar—$CH_2$—CH(COOH)—$(CH_2)_m$—C(═O)—NH—OH, —$CH_2$—O—C(═O)—$(CH_2)_m$—$X_3$, —$CH_2$—O—C(═O)—Ar—$CH_2$—$X_3$, and a protecting group, wherein $X_2$ is selected from the group consisting of —OH, —$CH_2$—CH(COOH)—$(CH_2)_p$—C(═O)—OH, and a protecting group, Ar is arylene, and $X_3$ is 2-oxotetrahydro-2H-thiopyran-3-yl, and each m and p is independently selected from the group consisting of 1, 2, 3, and 4; or $R_3$ is selected from the group consisting of —O—C(═O)—O—$CH_2$—O—C(═O)—$(CH_2)_n$—CH(COOH)—$CH_2$—P(═O)(OH)$_2$, and —O—C(═O)—$CH_2$—$CH_2$—P(═O)(OH)—$CH_2$—CH(COOH)—$(CH_2)_n$—C(═O)—OH, wherein each n is independently an integer selected from the group consisting of 1, 2, 3, and 4; and $R_4$ is selected from the group consisting of —$NH_2$, —COOH, —C(═O)—NH—$CH_2$—C(═O)—OH, and —C(═O)—NH—$CH_2$—$CH_2$—S(═O)$_2$—OH; and pharmaceutically acceptable salts thereof.

In some aspects of the compound of formula (I), (a) $R_1$ and $R_2$ are both H; (b) $R_1$ is H and $R_2$ is OH; (c) $R_1$ is OH and $R_2$ is H; or (d) $R_1$ and $R_2$ are both OH.

In some aspects, $R_3$ is OH and $R_4$ is selected from the group consisting of —NH—$X_1$, —COO—$X_1$, —C(═O)—NH—$CH_2$—C(═O)—O—$X_1$, and —C(═O)—NH—$CH_2$—$CH_2$—S(═O)$_2$—O—$X_1$, wherein $X_1$ is selected from the group consisting of —(C═O)—$CH_2$—$CH_2$—P(═O)(OH)—$X_2$, —(C═O)—$CH_2$—$CH_2$—CH(COOH)—$CH_2$—P(═O)(OH)—$X_2$, —$CH_2$—O—(C═O)—$CH_2$—$CH_2$—P(═O)(OH)—$X_2$, —$CH_2$—O—C(═O)—$CH_2$—$CH_2$—CH(COOH)—$CH_2$—P(═O)(OH)—$X_2$, —$CH_2$—O—C(═O)—$CH_2$—$CH_2$—CH(COOH)—NH—(C═O)—NH—CH(COOH)—$CH_2$—CH$(CH_3)_2$, —$CH_2$—O—C(═O)—Ar—$CH_2$—CH(COOH)—$CH_2CH_2$—C(═O)—NH—OH, —$CH_2$—O—C(═O)—$CH_2$—$CH_2$—$X_3$, —$CH_2$—O—C(═O)—Ar—$CH_2$—$X_3$, and a protecting group, wherein $X_2$ is selected from the group consisting of —OH, —$CH_2$—CH(COOH)—$CH_2$—$CH_2$—CH(═O)—

OH, and a protecting group, Ar is phenyl, and $X_3$ is 2-oxo-tetrahydro-2H-thiopyran-3-yl.
In such aspects, the compound of formula (I) is selected from the group consisting of:
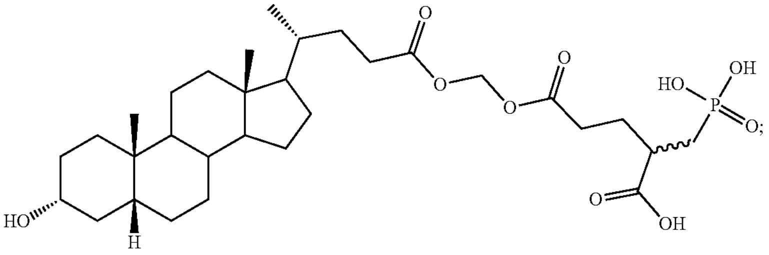
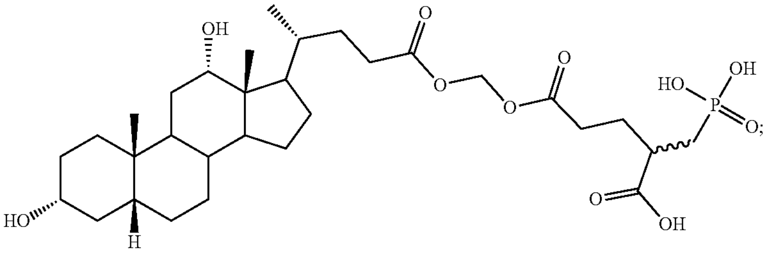
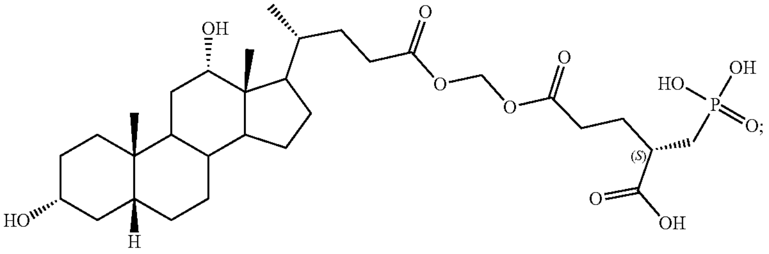
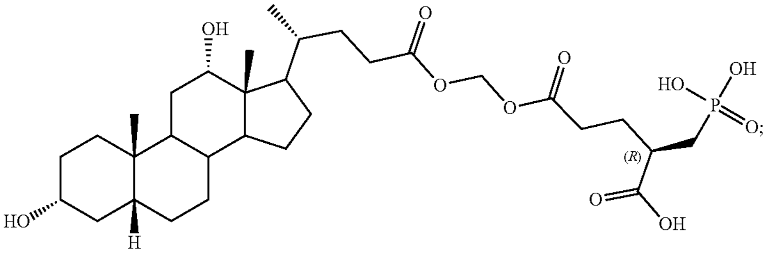
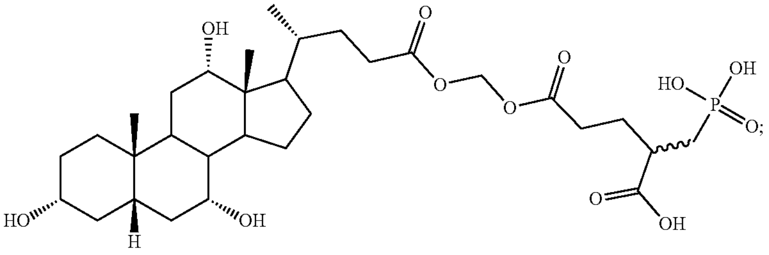
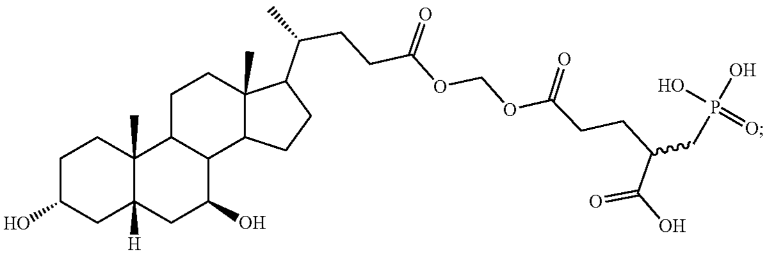

-continued
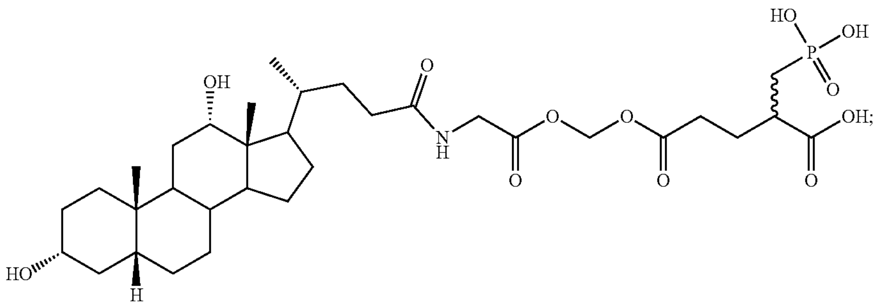
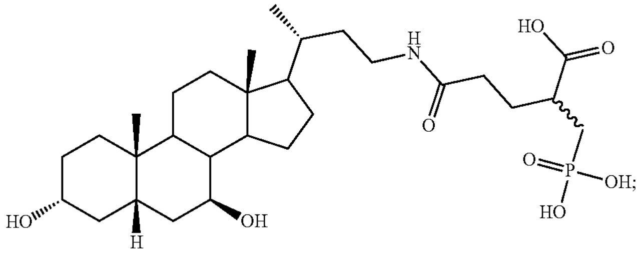
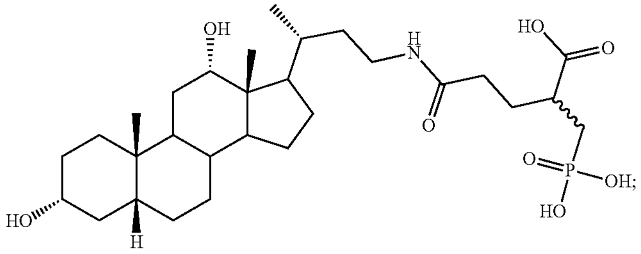
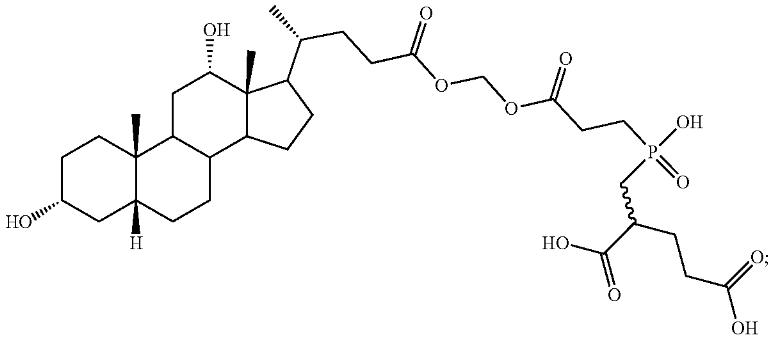
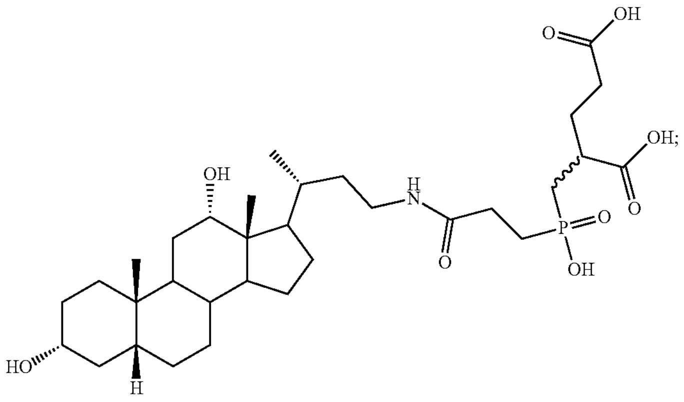

-continued
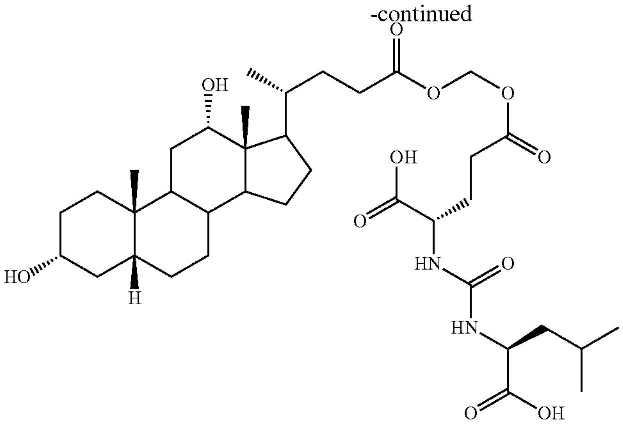
;
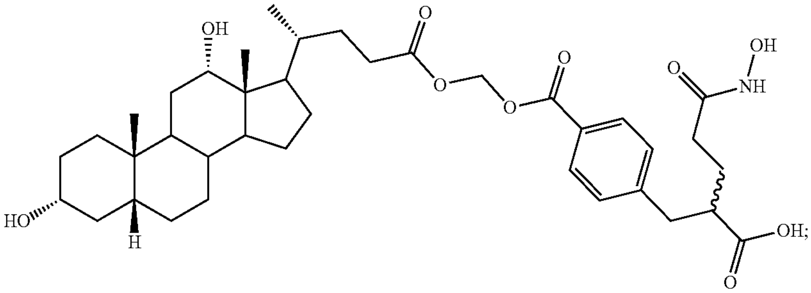
;
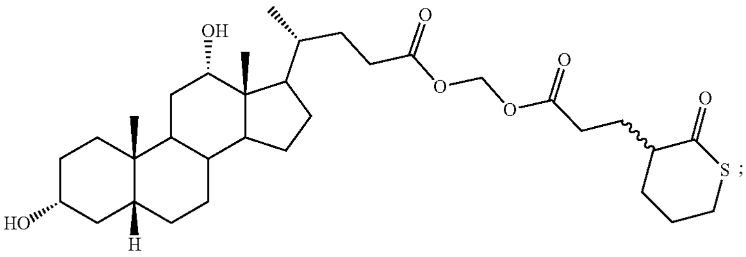
; and
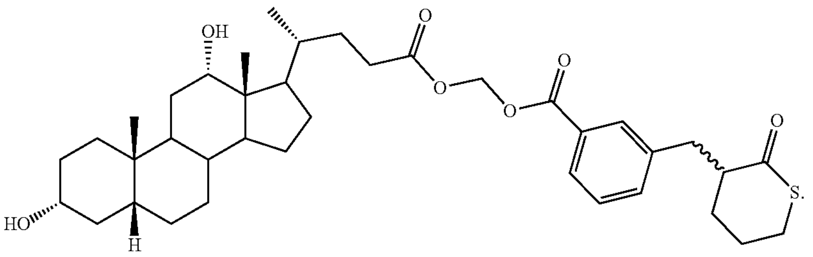
.
In some aspects, $R_3$ is selected from the group consisting of —O—C(═O)—O—$CH_2$—O—C(═O)—$CH_2$—$CH_2$—CH(COOH)—$CH_2$—P(═O)$(OH)_2$, and —O—C(═O)—$CH_2$—$CH_2$—P(═O)(OH)—$CH_2$—CH(COOH)—$CH_2$—$CH_2$—C(═O)—OH, and $R_4$ is selected from the group consisting of —$NH_2$, —COOH, —C(═O)—NH—$CH_2$—C(═O)—OH, and —C(═O)—NH—$CH_2$—$CH_2$—S(═O)$_2$—OH.
In such aspects, the compound of formula (I) is selected from the group consisting of:

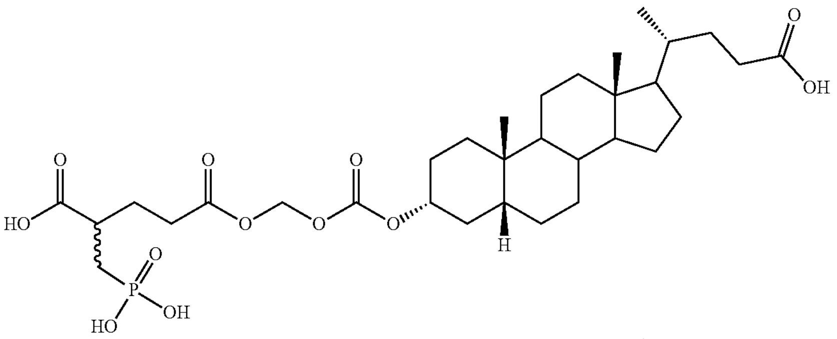
;

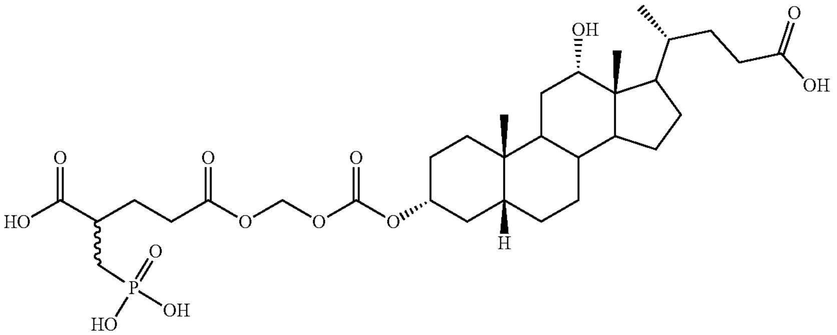
;

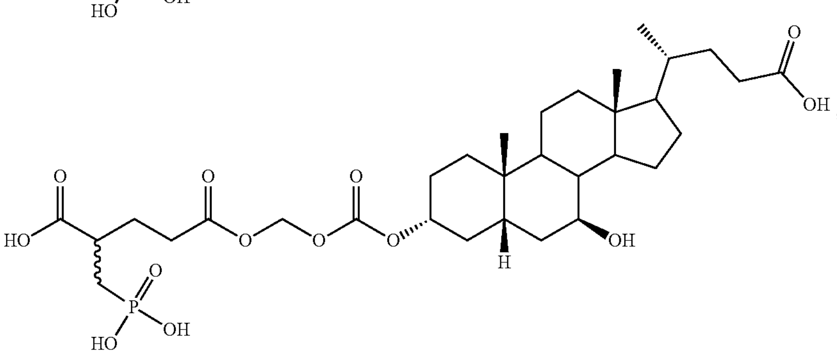
; and

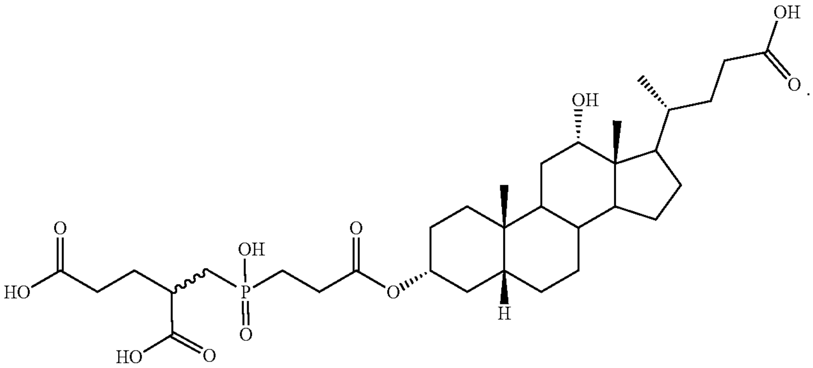
.

In other aspects, the presently disclosed subject matter provides a method for treating a disease or condition associated with an elevated GCPII activity in a subject in need of treatment thereof, the method comprising administering to the subject a therapeutically effective amount of a conjugate of formula (I) or a pharmaceutically acceptable salt thereof.

Further, an object of the presently disclosed subject matter is the conjugate of general formula (I) for use in medicine, preferably in the treatment of disease or condition associated with an elevated GCPII activity.

In certain aspects, the disease or condition associated with an elevated GCPII activity comprises an inflammatory bowel disease. In more certain aspects, the inflammatory bowel disease is selected from the group consisting of Crohn's disease (CD) and ulcerative colitis (UC). In particular aspects, the method for treating a disease or condition associated with an elevated GCPII activity inhibits GCPII activity in the subject.

In other aspects, the presently disclosed subject matter provides a pharmaceutical composition comprising at least one compound of general formula (I) alone or in combination with one or more additional therapeutic agents in admixture with a pharmaceutically acceptable excipient.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 2A:
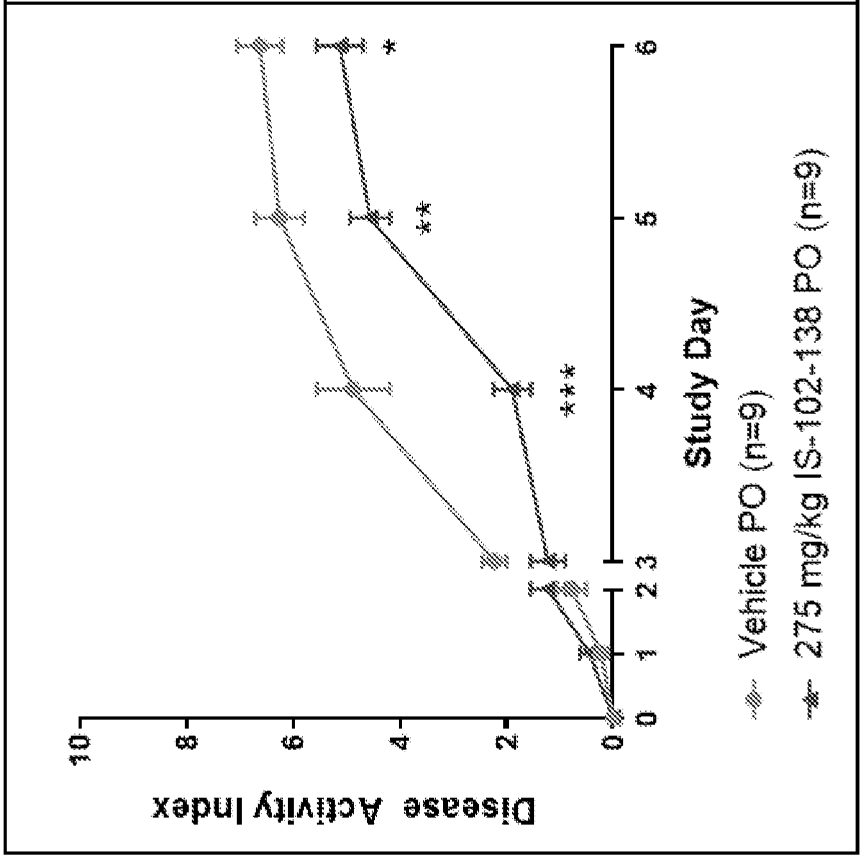
Figure 2B:
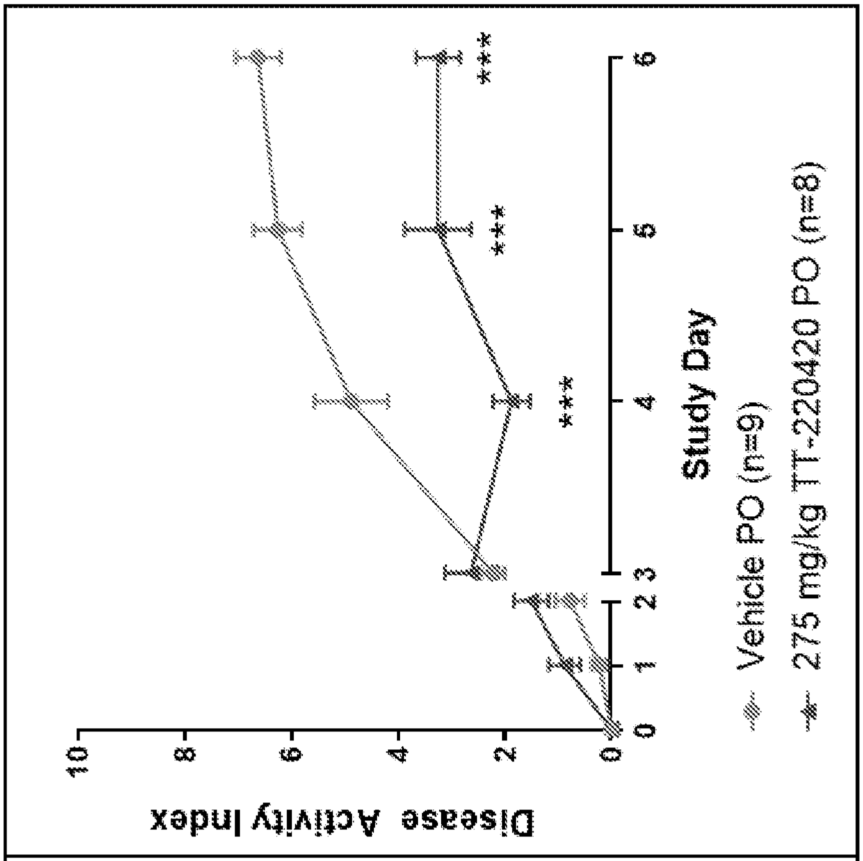
Figures 3A, 3B, 3C, 3D:
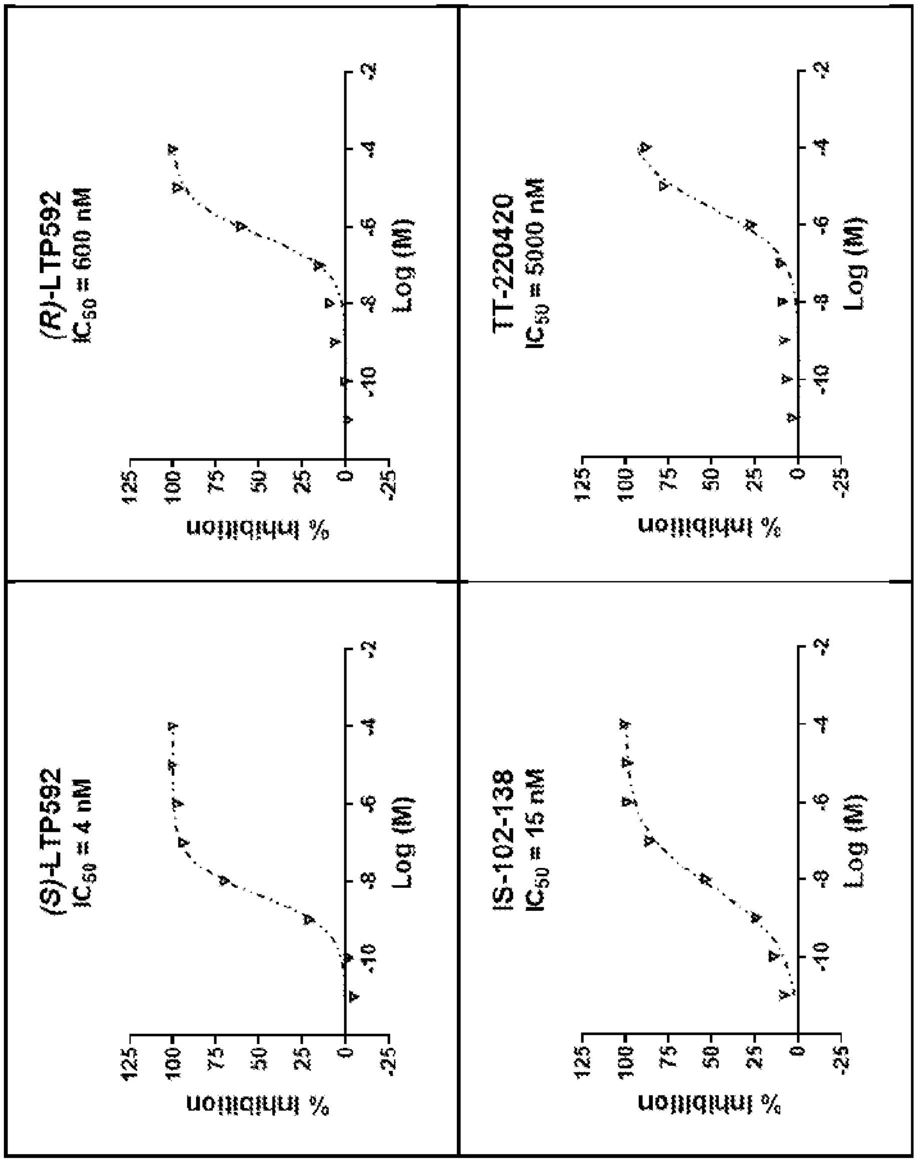
Figures 4A, 4B, 4C, 4D, 4E, 4F:
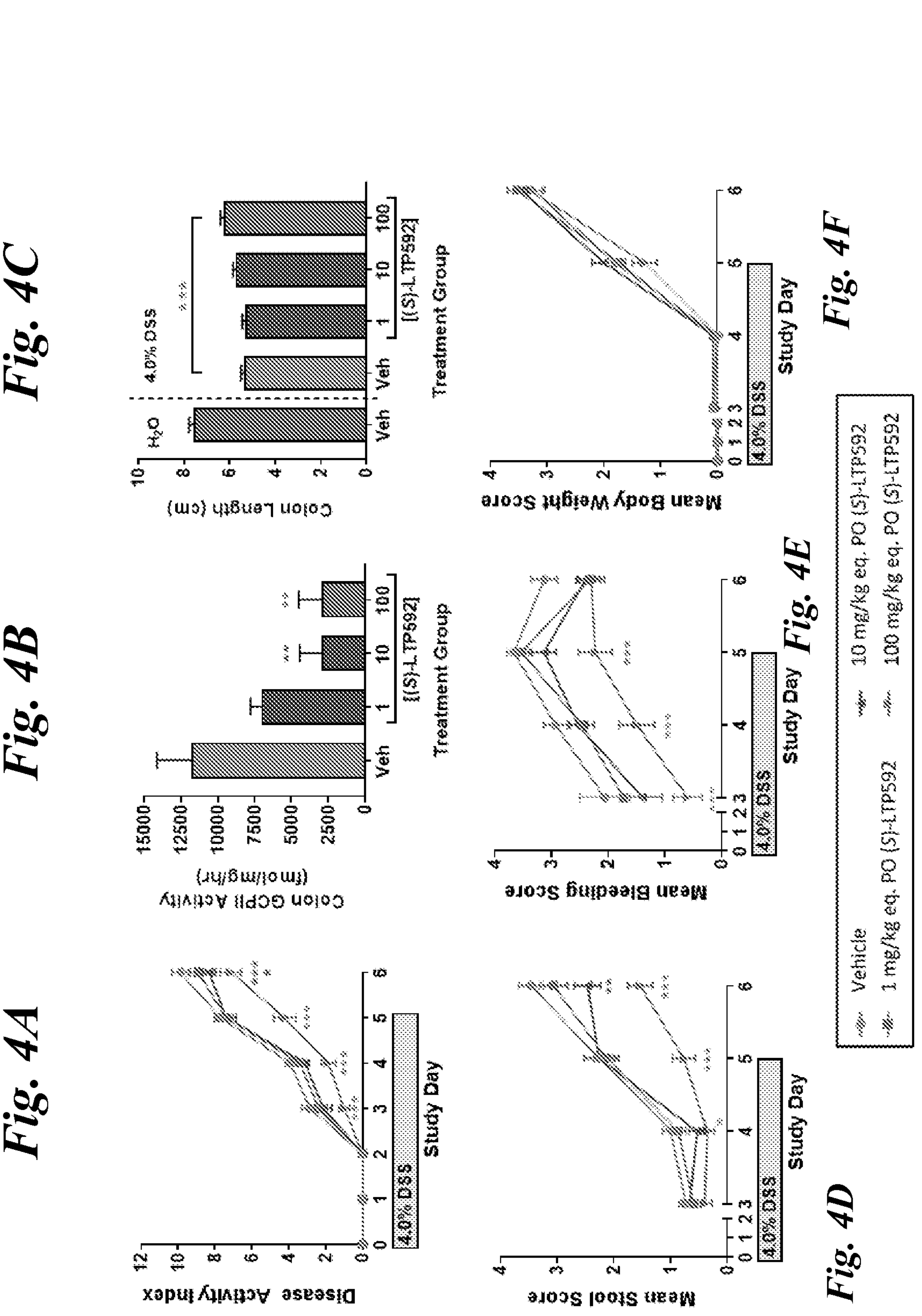
Figures 5A, 5B, 5C:
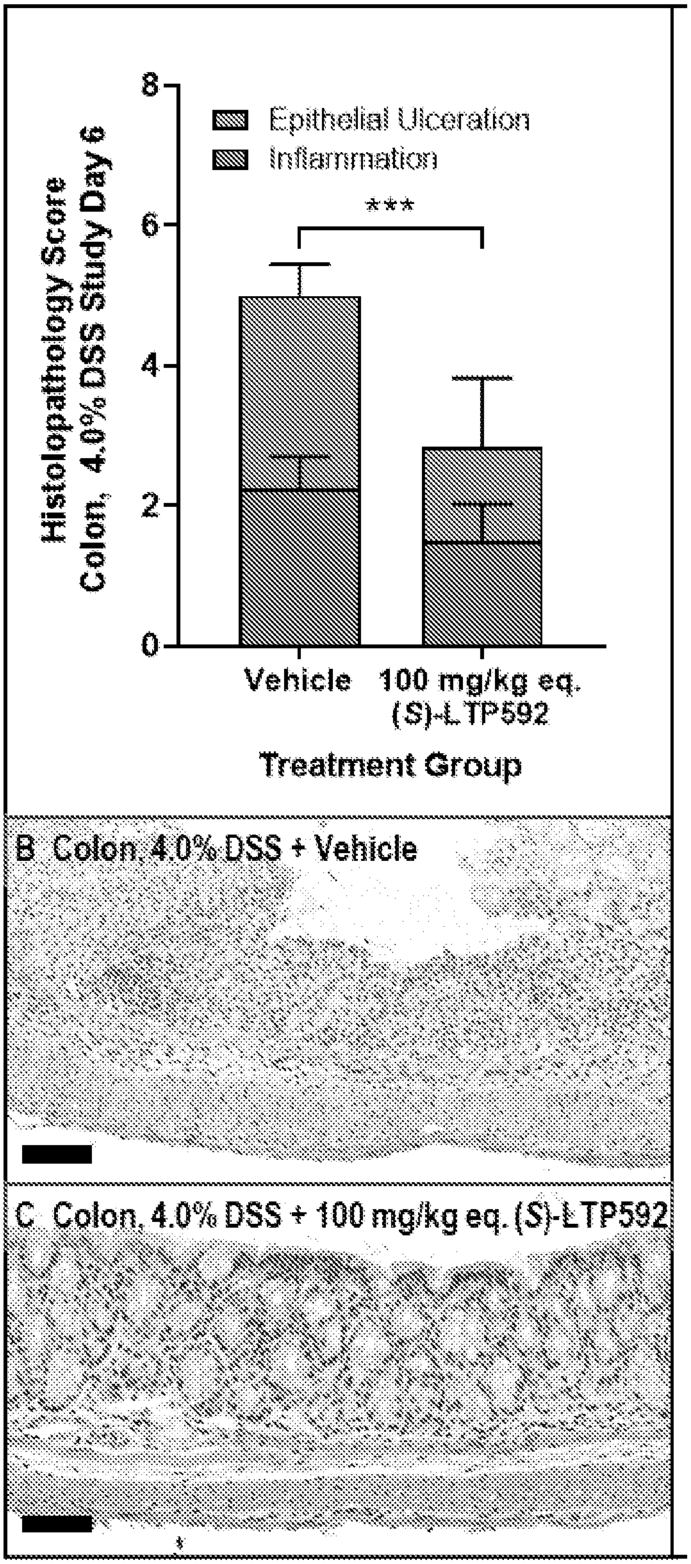
Figures 5D, 5E, 5F:
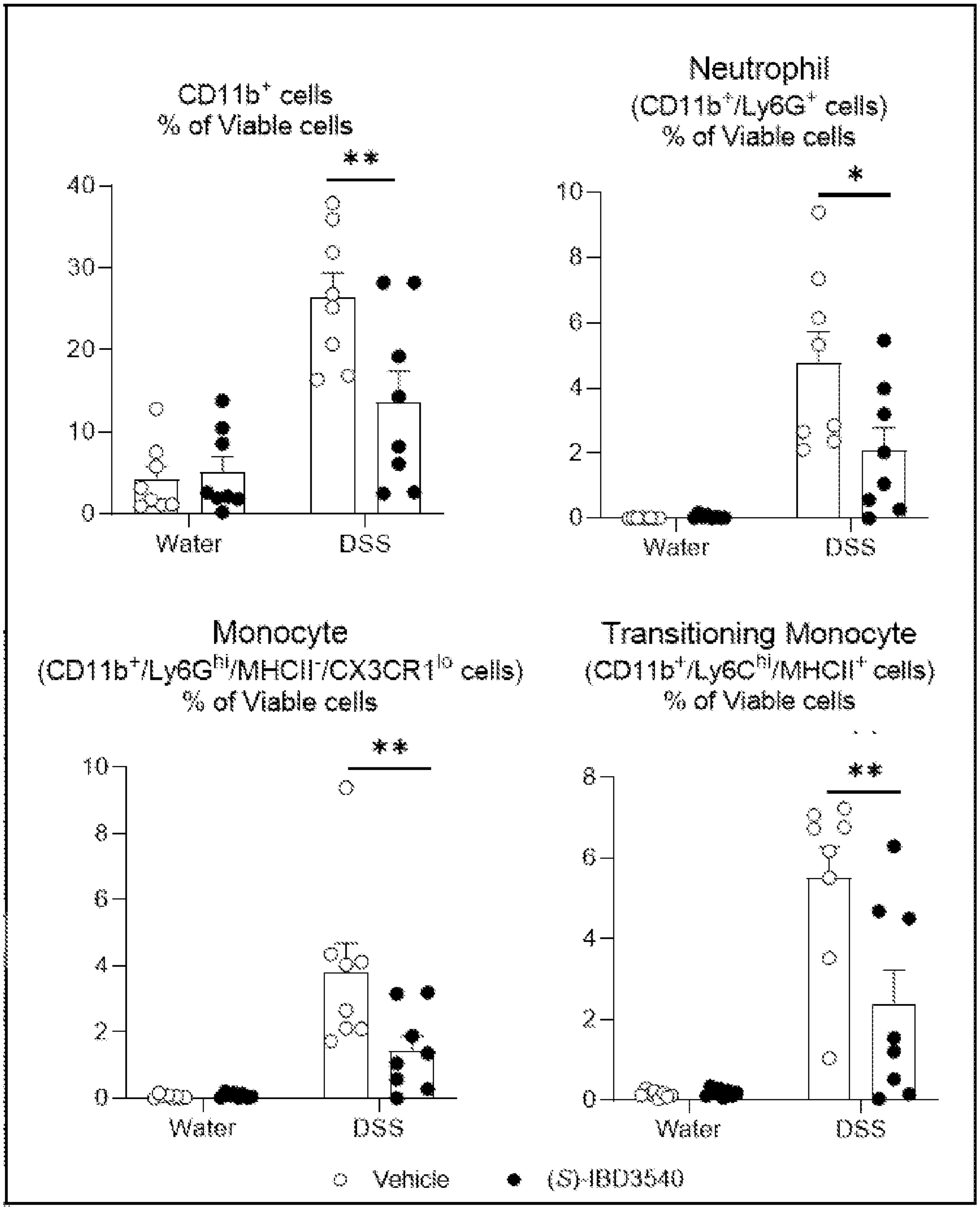

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, FIG. 1F, FIG. 1G, and FIG. 1H demonstrate that select bile acid 2-PMPA conjugates have measurable anti-colitis effects in the dextran-sodium sulfate (DSS) colitis model of inflammatory bowel diseases (IBD). Colitis was induced using either 2.5% DSS (FIG. 1A, FIG. 1B, and FIG. 1C) or 4.0% DSS (FIG. 1D, FIG. 1E, FIG. 1F, FIG. 1G, and FIG. 1H) resulting in the characteristic development of diarrhea, rectal bleeding and body weight loss. These parameters were evaluated daily, scored and summated to compute a disease activity index (DAI). Mice received once daily oral treatment with test article or vehicle beginning on Study Day 0 and continuing through Study Day 7. Test articles LTP592 (FIG. 1B, FIG. 1D), IS-101-020 (FIG. 1G) and IS-101-077 (FIG. 1H) displayed anti-IBD activity evidenced by significant reductions in DAI on Study Days 6 and 7 for drug treated mice. Test articles LTP582 (FIG. 1A), LTP588 (FIG. 1C), LTP1054 (FIG. 1E) and IS-101-010 (FIG. 1F) were inactive. All data depicted as mean+/−SEM. 2-way ANOVA, *p<0.05, p<0.01, *p<0.001;

FIG. 2A and FIG. 2B demonstrate that conjugates of deoxycholic acid with urea- and hydroxymate-based GCPII inhibitors are protective in the dextran-sodium sulfate (DSS) colitis model of inflammatory bowel diseases (IBD). Colitis was induced using 4.0% DSS resulting in the characteristic development of diarrhea, rectal bleeding and body weight loss. These parameters were evaluated daily, scored and summated to compute a disease activity index (DAI). Mice received once daily oral treatment with test article or vehicle beginning on Study Day 0 and continuing through Study Day 6. Test articles IS-102-138 (FIG. 2A) and TT-220420 (FIG. 2B) displayed anti-IBD activity evidenced by significant reductions in DAI on Study Days 4 through 6 for drug treated mice. All data depicted as mean+/−SEM. 2-way ANOVA, *p<0.05, p<0.01, *p<0.001;

FIG. 3A, FIG. 3B, FIG. 3C, and FIG. 3D show IC50 values for selected bile acid GCPII inhibitor conjugates. IC50s were determined for selected inhibitors using a previously described radiosubstrate based assay employing recombinant human GCPII. Rojas et al., 2002. All were found to inhibit GCPII at concentrations ranging from low nanomolar to low micromolar values. Additionally, it was determined that (S)-LTP592 (FIG. 3A) is the active enantiomer of (R/S)-LTP592, as it displays 150-fold greater potency than (R)-LTP592 (FIG. 3B);

FIG. 4A, FIG. 4B, FIG. 4C, FIG. 4D, and FIG. 4F demonstrate that orally administered (S)-LTP592 protects against dextran sodium sulfate (DSS)-induced colitis in a dose-dependent manner. Six-week old male C57Bl/6NHsd mice were challenged with 4.0% DSS in drinking water from Study Day 0-5 followed by exposure to freshwater, inducing severe acute colitis. Oral (S)-LTP592 was administered once daily beginning on study day 0 at 1 mg/kg, 10 mg/kg and 100 mg/kg 2-PMPA molar equivalent doses. (FIG. 4A) 100 mg/kg eq. (S)-LTP592 significantly decreased colitis severity as early as study day 3, with a trend towards dose-dependent protection emerging on study day 6 (n=15/group; ***p<0.001, *p<0.05 2-way ANOVA). (FIG. 4B) Correspondingly, colon tissues collected 4-hour post dose on study day 6 displayed >75% inhibition of GCPII enzymatic activity for effective doses of 10 mg/kg eq. and 100 mg/kg eq. (S)-LTP592, while GCPII was only 40% inhibited at the non-efficacious dose of 1 mg/kg eq. (n=8/group; p<0.01 2-tailed t-test). (FIG. 4C) Strikingly, 100 mg/kg eq. (S)-JHU3540 treatment also resulted in normalization of colon length on study day 6 (n=15/group, *p<0.001 2-tailed t-test). (FIG. 4D, FIG. 4E, and FIG. 4F) Efficacy of 100 mg/kg eq. (S)-LTP592 in the DSS-colitis model was driven by improvements in (FIG. 4C) stool score and (FIG. 4D) bleeding score (n=15/group; ***p<0.001, *p<0.05 2-way ANOVA);

FIG. 5A, FIG. 5B, FIG. 5C, FIG. 5D, FIG. 5E, FIG. 5F, and FIG. 5G show that orally administered (S)-LTP592 is anti-inflammatory in the DSS-colitis model. Six-week old male C57Bl/6NHsd mice were challenged with 4.0% DSS in drinking water from study day 0-6 followed by exposure to freshwater. Oral (S)-LTP592 was administered once daily beginning on study day 0 at 100 mg/kg 2-PMPA molar equivalent doses. (FIG. 5A, FIG. 5B, and FIG. 5C) 100 mg/kg eq. (S)-LTP592 significantly improved colon histology on study day 6 and reduced the number and depth of ulcerations and the degree of inflammatory infiltration, as (FIG. 5A) scored by a blinded pathologist and (FIG. 5B-FIG. 5C) depicted in representative images (n=10/group; *p<0.001, 2-tailed t-test). (FIG. 5D, FIG. 5E, FIG. 5F, and FIG. 5G) A subset of mice (n=8/group) were euthanized on study day 5, prior to fulminant colitis. Their colons were harvested and processed for flow cytometry. As expected, 4.0% DSS resulted in significant colon inflammation including increases in all myeloid populations examined, including (FIG. 5D) total CD11b+ white blood cells and (FIG. 5E) neutrophils, (FIG. 5F) circulating monocytes and (FIG. 5G) transitioning monocytes. All DSS-induced changes in myeloid inflammatory cell populations were attenuated by (S)-IBD3540 treatment (n=8-9/group, p<0.01, *p<0.05, 2-tailed t-test).

Figure 6:
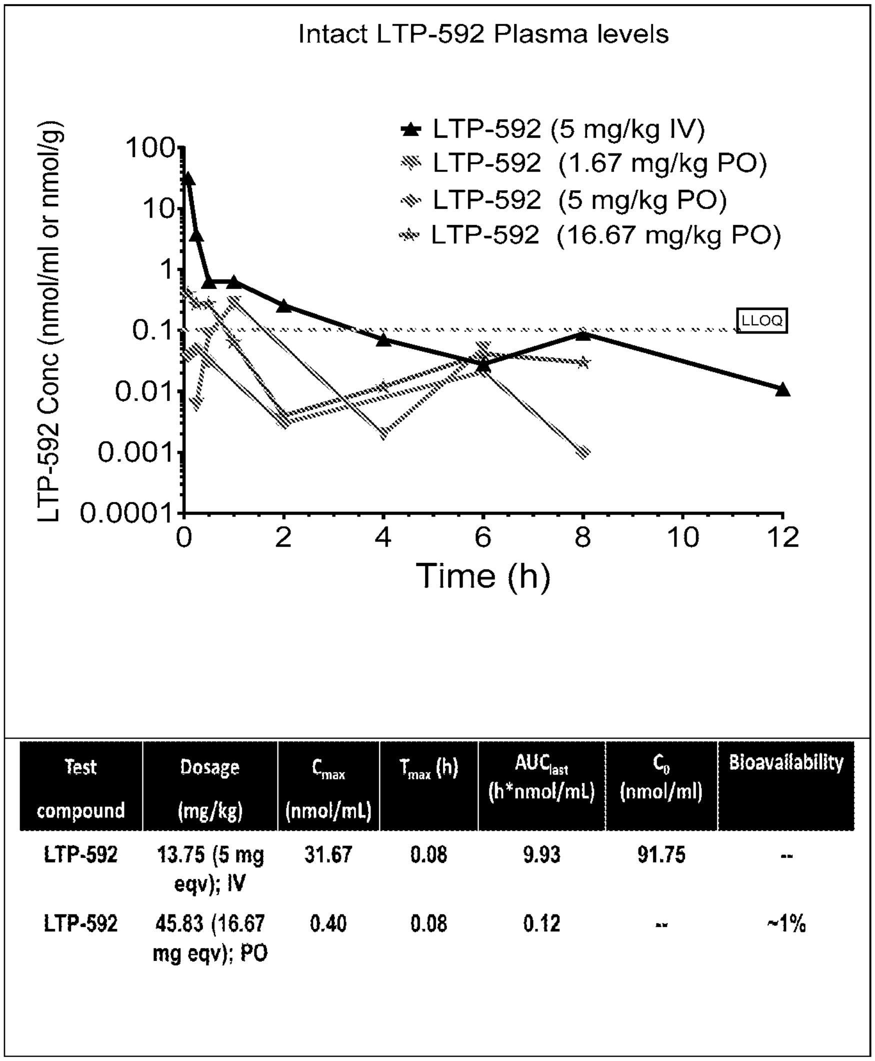

FIG. 6 shows the in vivo pharmacokinetics of LTP-592 in dogs. Shown are concentration-time profiles and pharmacokinetic parameters of LTP-592 following IV and oral administration of LTP-592 in dogs; and FIG. 7A, FIG. 7B, and FIG. 7C show the in vivo pharmacokinetics of LTP-592 in mice. Shown are the concentration-time profiles of LTP-592 following IV and oral administration in (FIG. 7A), plasma (FIG. 7B), and colon (FIG. 7C) pharmacokinetic parameters.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figure.

Therefore, it is to be understood that the presently disclosed subject matter is not to be limited to the specific embodiments disclosed and that modifications and other embodiments are intended to be included within the scope of the appended claims.

I. Bile Acid-GCPII Inhibitor Conjugates to Treat Inflammatory Diseases, Including Inflammatory Bowel Disease (IBD)

Immune-mediated gastrointestinal disorders encompass a wide range of debilitating gastrointestinal diseases of various etiologies. One such immune-mediated gastrointestinal disorder, inflammatory bowel disease (IBD), is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. The onset of IBD typically occurs during young adulthood, with the most common symptoms being diarrhea, abdominal pain, and fever. The diarrhea may range from mild to severe and in ulcerative colitis often is accompanied by bleeding. Anemia and weight loss are additional common signs of IBD. Ten percent to fifteen percent of all patients with IBD will require surgery over a ten-year period. In addition, patients with IBD are at increased risk for the development of intestinal cancer. Increased occurrence of psychological problems, including anxiety and depression, are perhaps not surprising symptoms of what is often a debilitating disease that strikes people in the prime of life.

A. GCPII Inhibitors Comprising 2-(Phosphonomethyl) Pentanedioic Acid (2-PMPA) Conjugated to a Bile Acid In some embodiments, the presently disclosed subject matter provides GCPII inhibitors, which have anti-IBD efficacy. The presently disclosed GCPII inhibitors were formed by conjugating the potent GCPII inhibitor 2-(phosphonomethyl) pentanedioic acid (2-PMPA) to a bile acid. The chemical formula of 2-PMPA is provided immediately herein below:

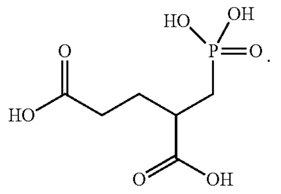 [SMILES: O=C(O)CCC(CP(=O)(O)O)C(=O)O]

Bile acids, which are abundant endogenously, were selected as the conjugate as they also are reported to have direct immunomodulatory effects in a variety of inflammatory models, Sipka and Bruckner, 2014; Calmus and Poupon, 2014; Ho and Steinman, 2016, including protection in IBD models. Laukens, et al., 2014. The presently disclosed subject matter further provides the use of such novel GCPII inhibitor/bile acid conjugates in treating inflammatory bowel disease and other inflammatory diseases.

Bile acids have the following general chemical structure:

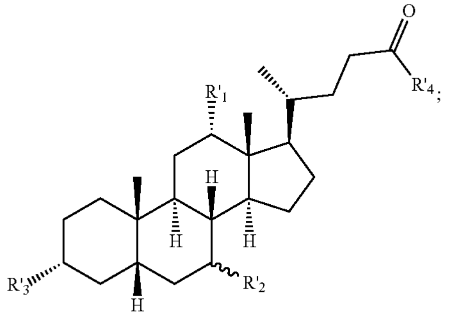

wherein:

$R'_1$ and $R'_2$ are each independently H or —OH;

$R'_3$ is —OH;

$R'_4$ is selected from the group consisting of —OH, —$NHCH_2COOH$, and —$NHCH_2CH_2SO_3H$; and salts thereof.

Representative bile acids include, but are not limited to, cholic acid, glycocholic acid, deoxycholic acid, lithocholic acid, glycodeoxycholic acid, chenodeoxycholic acid (also referred to as chenocholic acid), glycochenodeoxycholic acid, ursodeoxycholic acid, taurocholic acid, taurodeoxycholic acid, taurochenodeoxycholic acid, and derivatives thereof, the structures of which are provided immediately herein below in Table 1.

TABLE 1

| Representative Bile Acids | |
|---|---|
| Bile Acid | Structure |
| cholic acid | 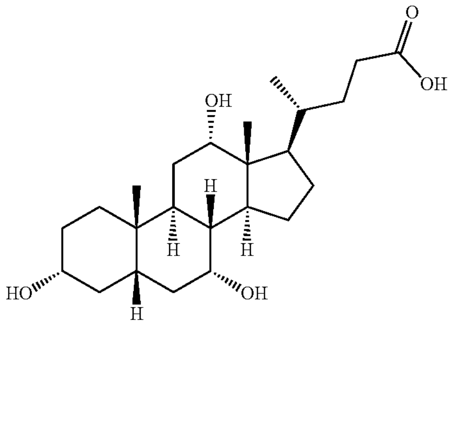 |

TABLE 1-continued
| Representative Bile Acids | |
|---|---|
| Bile Acid | Structure |
| glycocholic acid | 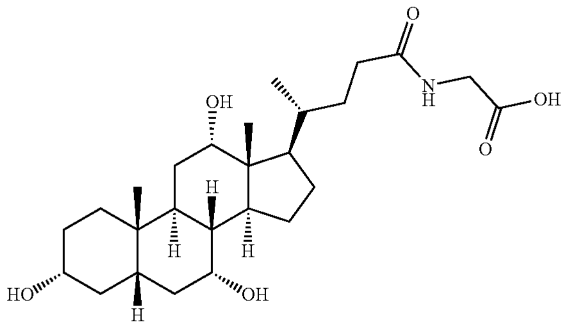 |
| taurocholic acid | 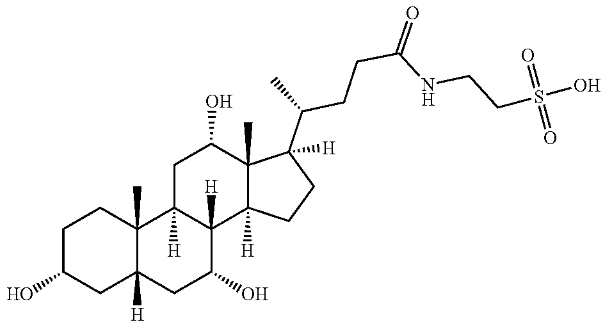 |
| deoxycholic acid | 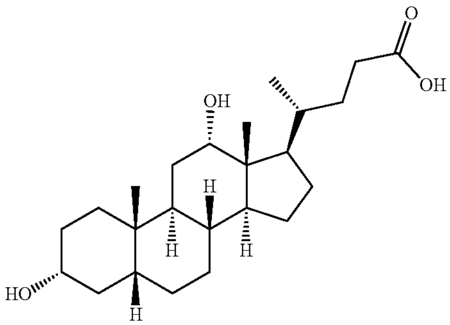 |
| chenodeoxycholic acid | 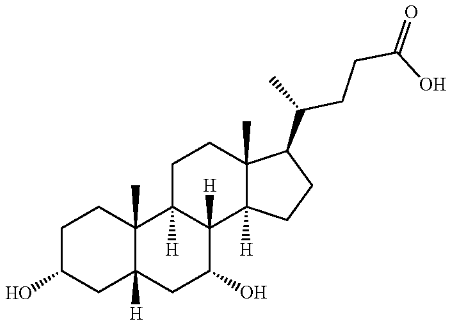 |

TABLE 1-continued
| Representative Bile Acids | |
|---|---|
| Bile Acid | Structure |
| glycochenodeoxycholic acid | 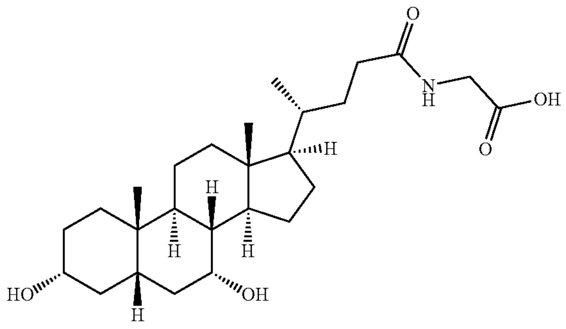 |
| taurochenodeoxycholic acid | 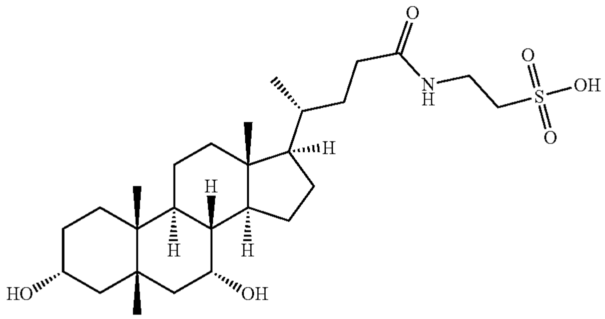 |
| lithocholic acid | 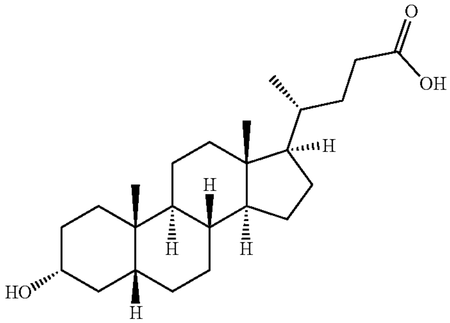 |
| glycodeoxycholic acid | 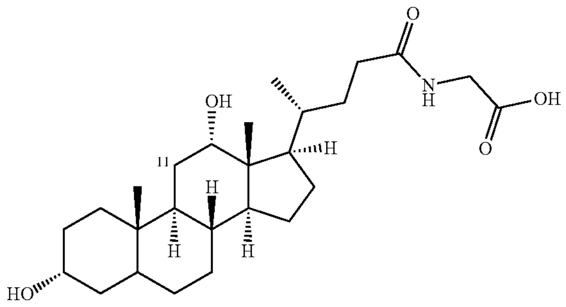 |

TABLE 1-continued

| Representative Bile Acids | |
|---|---|
| Bile Acid | Structure |
| ursodeoxycholic acid | 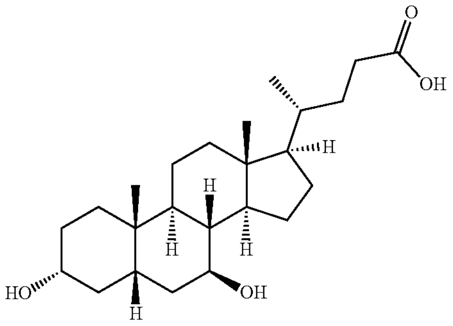 |
| taurodeoxycholic acid | 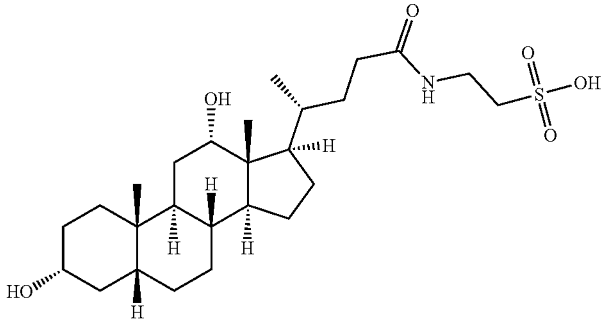 |

Accordingly, in some embodiments, the presently disclosed subject matter provides a conjugate of 2-(phosphonomethyl) pentanedioic acid (2-PMPA), or a derivative thereof, and a bile acid, or derivative thereof.

In some embodiments, the conjugate comprises a compound of formula (I):

(I)

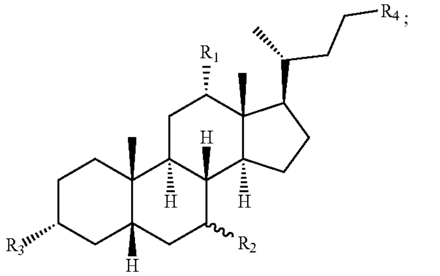

wherein $R_1$ and $R_2$ are each independently H or —OH; and wherein $R_3$ is OH and $R_4$ is selected from the group consisting of —NH—$X_1$, —COO—$X_1$, —C(═O)—NH—$CH_2$—C(═O)—O—$X_1$, and —C(═O)—NH—$CH_2$—$CH_2$—S(═O)$_2$—O—$X_1$, wherein $X_1$ is selected from the group consisting of —(C═O)—$(CH_2)_m$—P(═O)(OH)—$X_2$, —(C═O)—$(CH_2)_m$—CH(COOH)—$CH_2$—P(═O)(OH)—$X_2$, —$CH_2$—O—(C═O)$(CH_2)_m$—P(═O)(OH)—$X_2$, —$CH_2$—O—C(═O)—$(CH_2)_m$—CH(COOH)—$CH_2$—P(═O)(OH)—$X_2$, —$CH_2$—O—C(═O)—$(CH_2)_m$—CH(COOH)—NH—(C═O)—NH—CH(COOH)—$CH_2$—CH$(CH_3)_2$, —$CH_2$—O—C(═O)—Ar—$CH_2$—CH(COOH)—$(CH_2)_m$—C(═O)—NH—OH, —$CH_2$—O—C(═O)—$(CH_2)_m$—$X_3$, —$CH_2$—O—C(═O)—Ar—$CH_2$—$X_3$, and a protecting group, wherein $X_2$ is selected from the group consisting of —OH, —$CH_2$—CH(COOH)—$(CH_2)_p$—C(═O)—OH, and a protecting group, Ar is arylene, and $X_3$ is 2-oxotetrahydro-2H-thiopyran-3-yl, and each m and p is independently selected from the group consisting of 1, 2, 3, and 4; or $R_3$ is selected from the group consisting of —O—C(═O)—O—$CH_2$—O—C(═O)—$(CH_2)_n$—CH(COOH)—$CH_2$—P(═O)(OH)$_2$, and —O—C(═O)—$CH_2$—$CH_2$—P(═O)(OH)—$CH_2$—CH(COOH)—$(CH_2)_n$—C(═O)—OH, wherein each n is independently an integer selected from the group consisting of 1, 2, 3, and 4; and $R_4$ is selected from the group consisting of —$NH_2$, —COOH, —C(═O)—NH—$CH_2$—C(═O)—OH, and —C(═O)—NH—$CH_2$—$CH_2$—S(═O)$_2$—OH; and pharmaceutically acceptable salts thereof.

In some embodiments, $R_1$ and $R_2$ are both H. In some embodiments, $R_1$ is H and $R_2$ is OH. In some embodiments, $R_1$ is OH and $R_2$ is H. In some embodiments, $R_1$ and $R_2$ are both OH.

In some embodiments, $R_3$ is OH and $R_4$ is selected from the group consisting of —NH—$X_1$, —COO—$X_1$, —C(═O)—NH—$CH_2$—C(═O)—O—$X_1$, and —C(═O)—NH—$CH_2$—$CH_2$—S(═O)$_2$—O—$X_1$, wherein $X_1$ is selected from the group consisting of —(C═O)—$CH_2$—$CH_2$—P(═O)(OH)—$X_2$, —(C═O)—$CH_2$—$CH_2$—CH(COOH)—$CH_2$—P(═O)(OH)—$X_2$, —$CH_2$—O—(C═O)—$CH_2$—$CH_2$—P(═O)(OH)—$X_2$, —$CH_2$—O—C(═O)—$CH_2$—$CH_2$—CH(COOH)—$CH_2$—P(═O)(OH)—$X_2$, —$CH_2$—O—C(═O)—$CH_2$—$CH_2$—CH(COOH)—NH—(C═O)—NH—CH(COOH)—$CH_2$—CH$(CH_3)_2$, —$CH_2$—O—C(═O)—Ar—$CH_2$—CH(COOH)—$CH_2CH_2$—C(═O)—NH—OH, —$CH_2$—O—C(═O)—

$CH_2$—$CH_2$—$X_3$, —$CH_2$—O—C(═O)—Ar—$CH_2$—$X_3$, and a protecting group, wherein $X_2$ is selected from the group consisting of —OH, —$CH_2$—CH(COOH)—$CH_2$—$CH_2$—CH(═O)—OH, and a protecting group, Ar is phenyl, and $X_3$ is 2-oxotetrahydro-2H-thiopyran-3-yl.

In some embodiments, $R_1$ is OH, $R_2$ is H, $R_3$ is OH, and $R_4$ is COO—$X_1$, wherein $X_1$ is —$CH_2$—O—C(═O)—$(CH_2)_m$—CH(COOH)—$CH_2$—P(═O)(OH)—$X_2$.

In some embodiments, $R_1$ is H and $R_2$ is OH or $R_1$ is OH and $R_2$ is H, $R_3$ is OH, and $R_4$ is —NH—$X_1$, wherein $X_1$ is —(C═O)—$CH_2$—$CH_2$—CH(COOH)—$CH_2$—P(═O)(OH)—$X_2$.

In some embodiments, the compound of formula (I) is selected from the group consisting of:

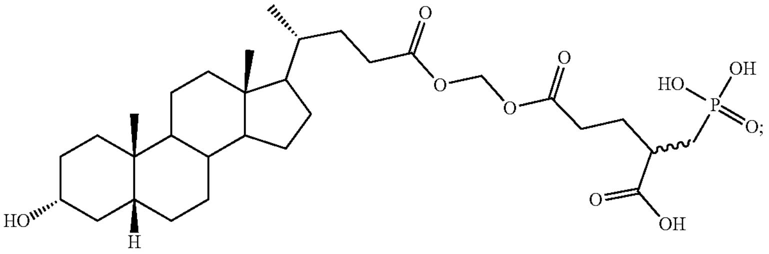

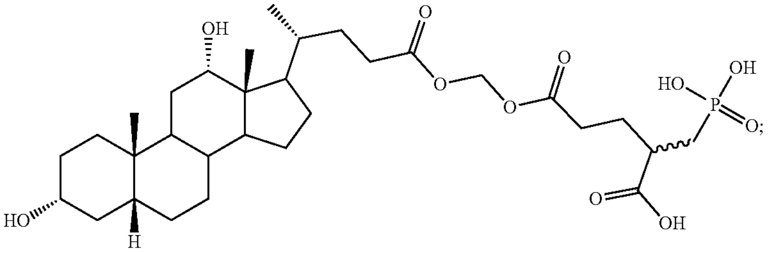

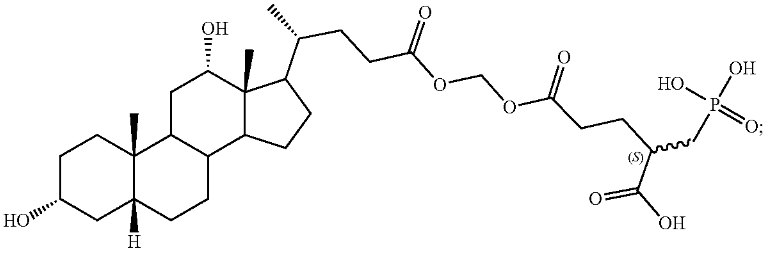

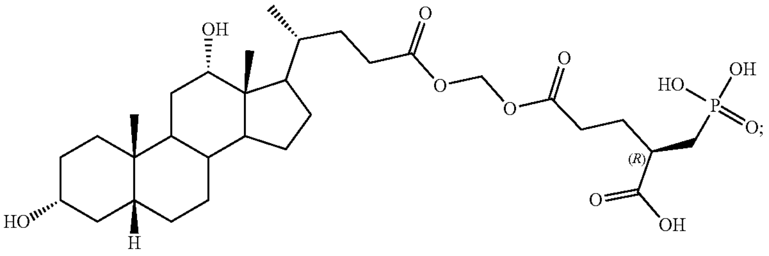

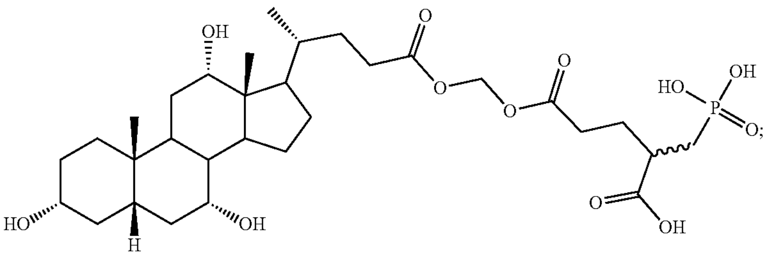

-continued
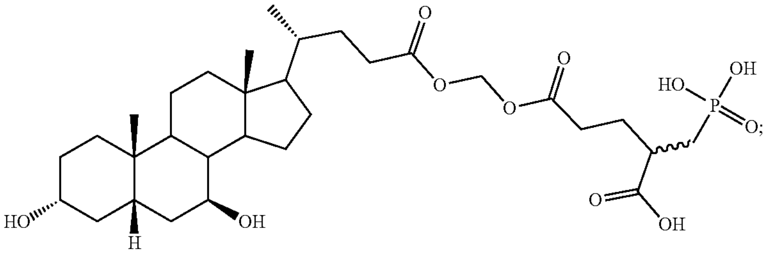
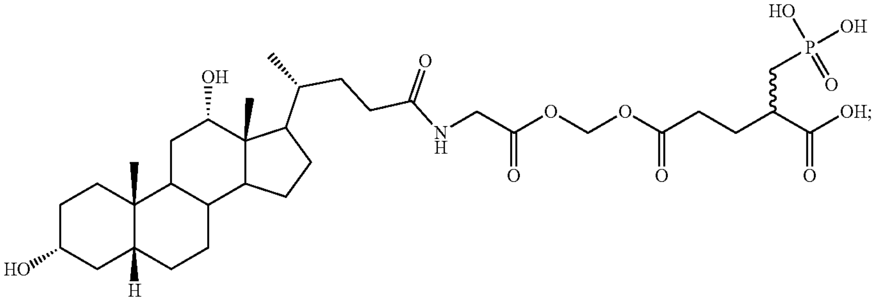
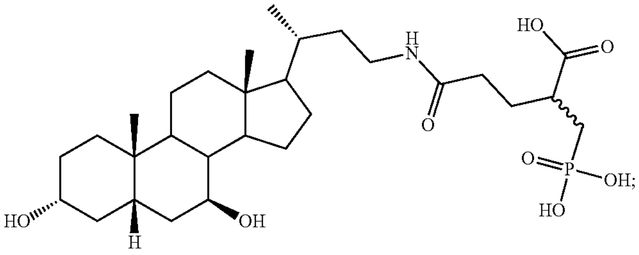
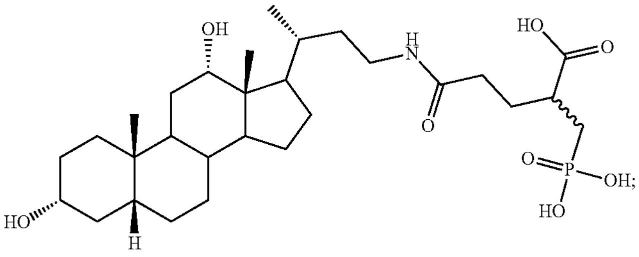
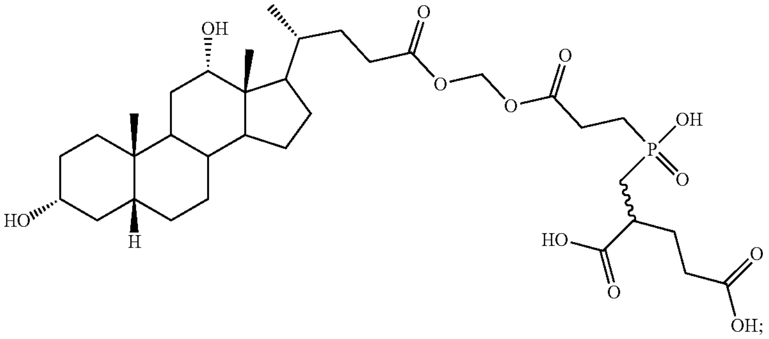

-continued
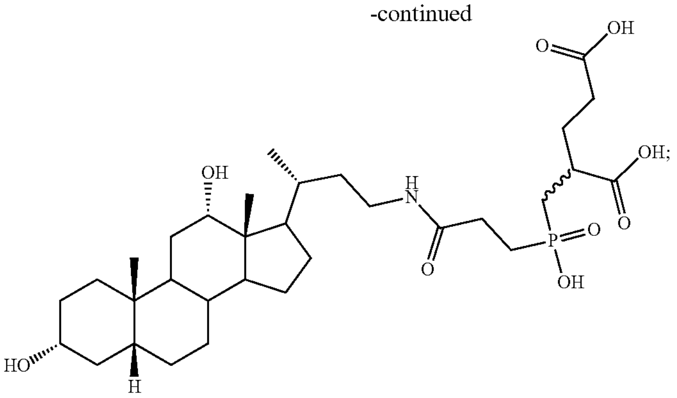
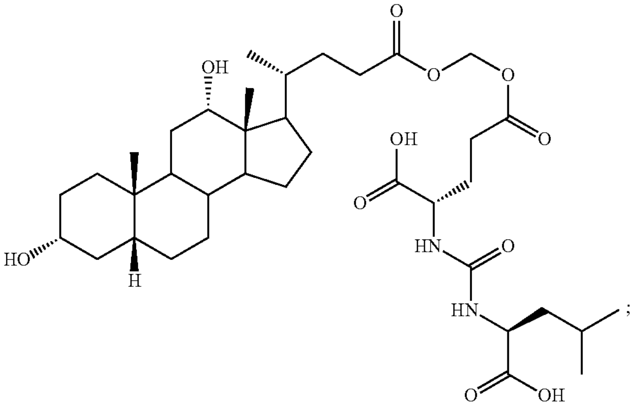
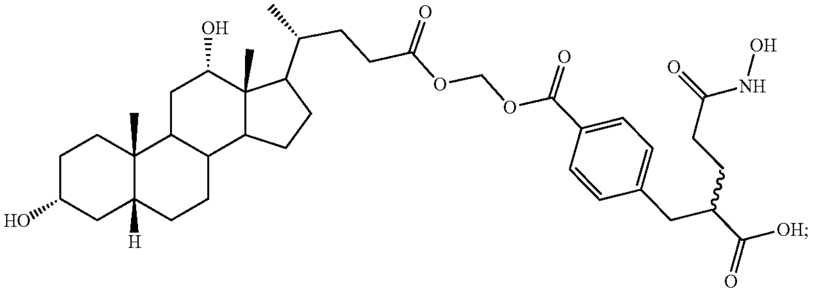
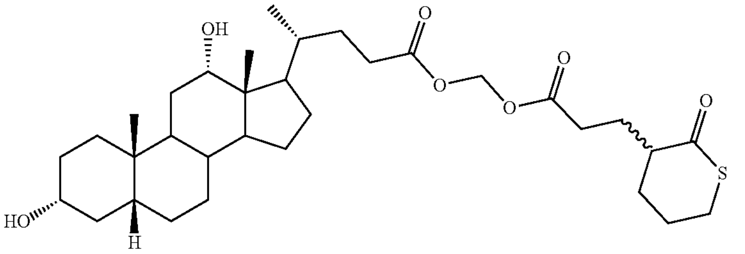
; and
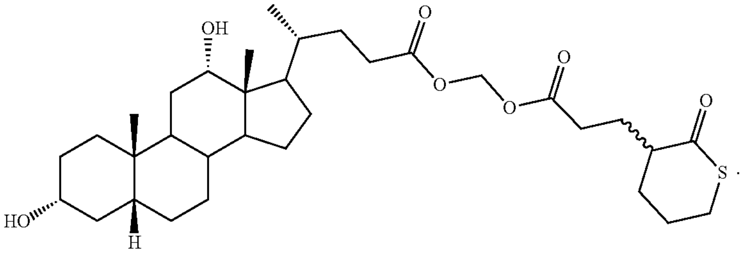
In some embodiments, $R_3$ is selected from the group consisting of —O—C(═O)—O—$CH_2$—O—C(═O)—$CH_2$—$CH_2$—CH(COOH)—$CH_2$—P(═O)$(OH)_2$, and —O—C(═O)—$CH_2$—$CH_2$—P(═O)(OH)—$CH_2$—CH(COOH)—$CH_2$—$CH_2$—C(═O)—OH, and $R_4$ is selected from the group consisting of —$NH_2$, —COOH, —C(═O)—NH—$CH_2$—C(═O)—OH, and —C(═O)—NH—$CH_2$—$CH_2$—S(═O)$_2$—OH.

In such embodiments, the compound of formula (I) is selected from the group consisting of:
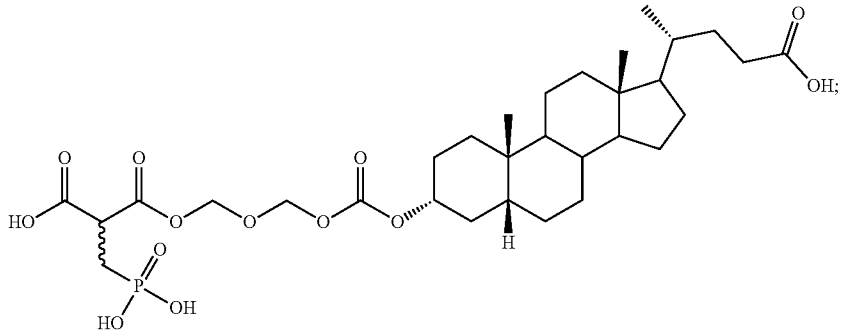
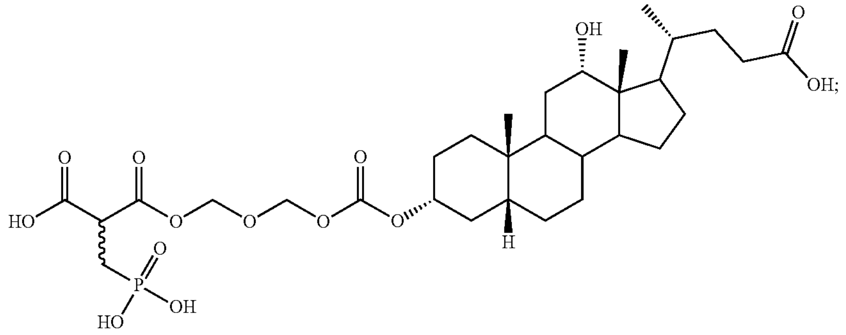
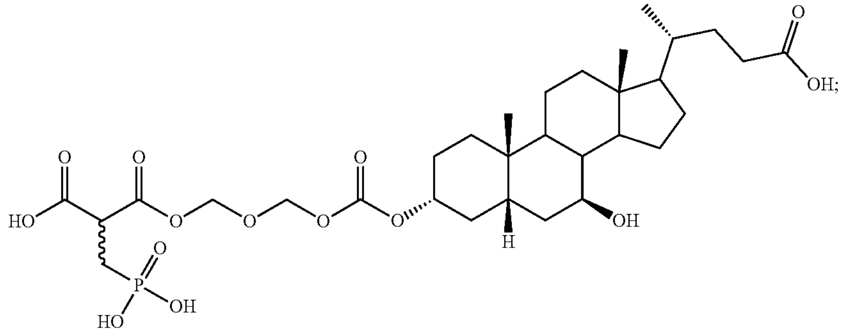
and
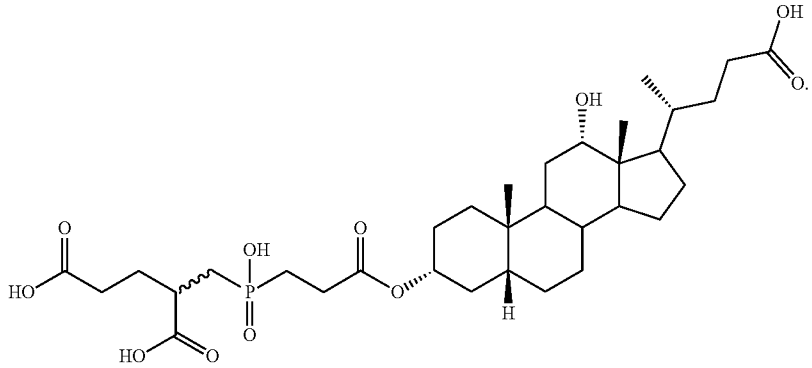
Representative compounds of formula (I) are provided immediately herein below in Table 2.

TABLE 2
| Representative Compounds of Formula (I). | | |
|---|---|---|
| Cmpd | Structure | MW |
| 1 (LTP582) | 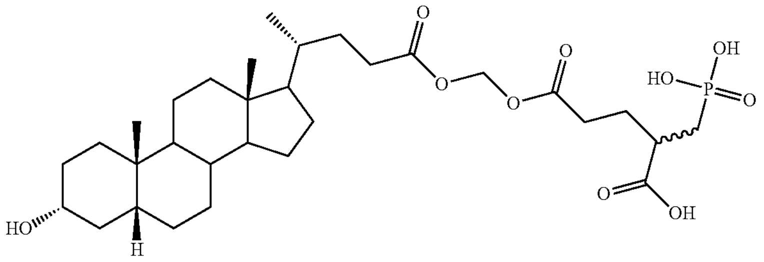 [SMILES: C[C@H](CCC(=O)OCOC(=O)CCC(CP(=O)(O)O)C(=O)O)C1CCC2C3CC[C@@H]4C[C@H](O)CC[C@]4(C)C3CC[C@@]21C] | 614.71 |
| 2 (LTP592) | 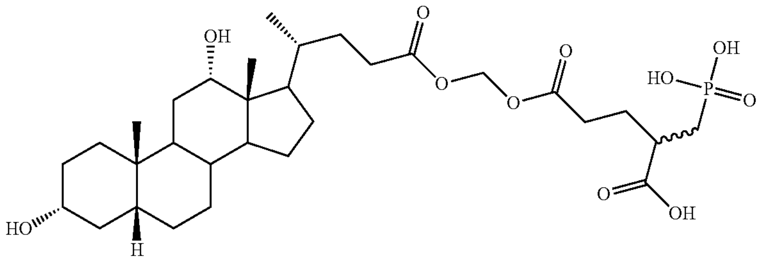 [SMILES: C[C@H](CCC(=O)OCOC(=O)CCC(CP(=O)(O)O)C(=O)O)C1CCC2C3CC[C@@H]4C[C@H](O)CC[C@]4(C)C3C[C@H](O)[C@@]21C] | 630.71 |
| 2a S-isomer | 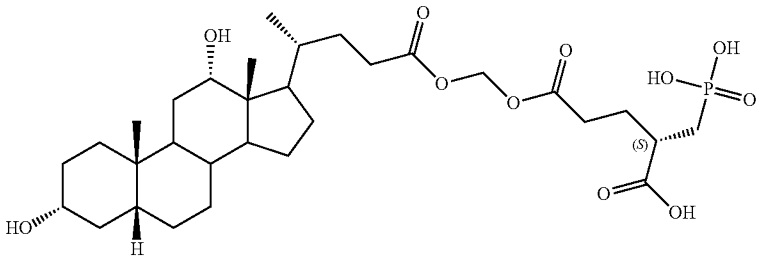 | 630.71 |
| 2b R-isomer | 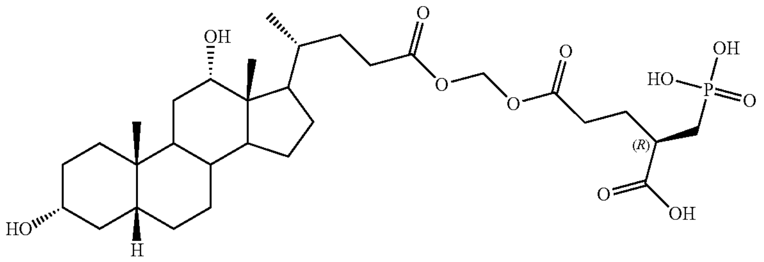 | 630.71 |
| 3 (LTP588) | 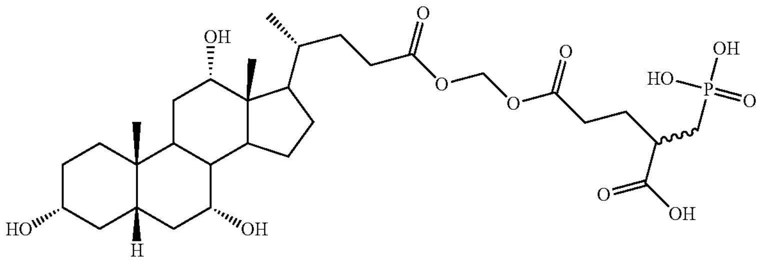 [SMILES: C[C@H](CCC(=O)OCOC(=O)CCC(CP(=O)(O)O)C(=O)O)C1CCC2C3C(C[C@H](O)[C@@]21C)[C@@]1(C)CC[C@@H](O)C[C@H]1C[C@H]3O] | 646.71 |

TABLE 2-continued
| Representative Compounds of Formula (I). | | |
|---|---|---|
| Cmpd | Structure | MW |
| 4 (LTP1054) | 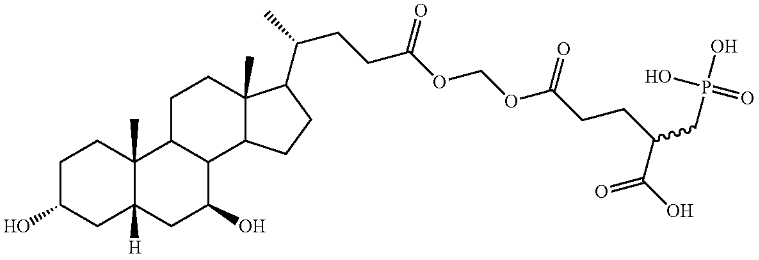 [SMILES: C[C@H](CCC(=O)OCOC(=O)CCC(CP(=O)(O)O)C(=O)O)C1CCC2C3C(CC[C@@]21C)[C@@]1(C)CC[C@@H](O)C[C@H]1C[C@@H]3O] | 630.71 |
| 5 (LTP791) | 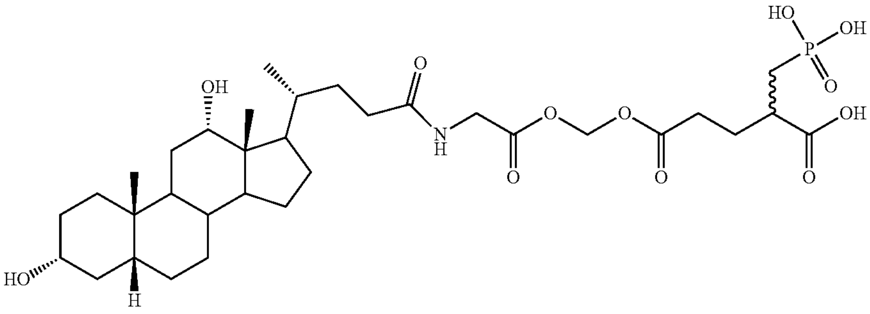 [SMILES: C[C@H](CCC(=O)NCC(=O)OCOC(=O)CCC(CP(=O)(O)O)C(=O)O)C1CCC2C3CC[C@@H]4C[C@H](O)CC[C@]4(C)C3C[C@H](O)[C@@]21C] | 687.34 |
| 6 (LTP798) | 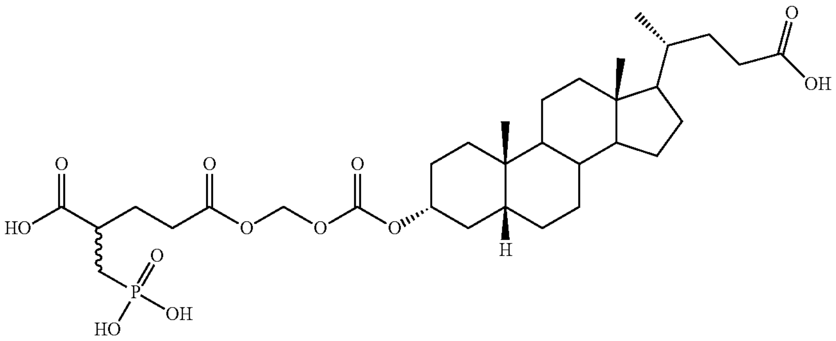 [SMILES: C[C@H](CCC(=O)O)C1CCC2C3CC[C@@H]4C[C@H](OC(=O)OCOC(=O)CCC(CP(=O)(O)O)C(=O)O)CC[C@]4(C)C3CC[C@@]21C] | 658.72 |
| 7 (LTP808) | 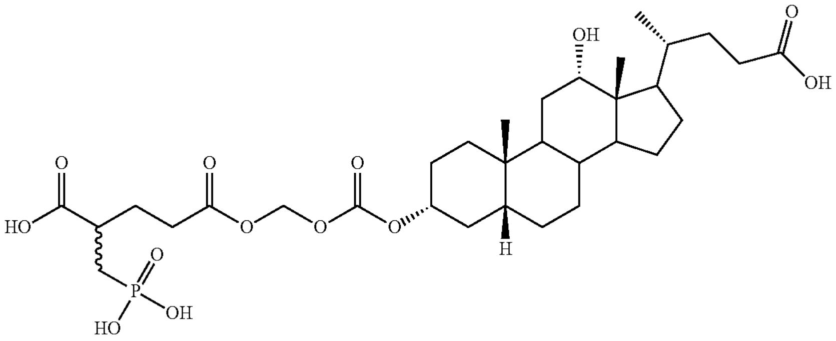 [SMILES: C[C@H](CCC(=O)O)C1CCC2C3CC[C@@H]4C[C@H](OC(=O)OCOC(=O)CCC(CP(=O)(O)O)C(=O)O)CC[C@]4(C)C3C[C@H](O)[C@@]21C] | 674.72 |

TABLE 2-continued
| Representative Compounds of Formula (I). | | |
| --- | --- | --- |
| Cmpd | Structure | MW |
| 8 (IS-101-010) | 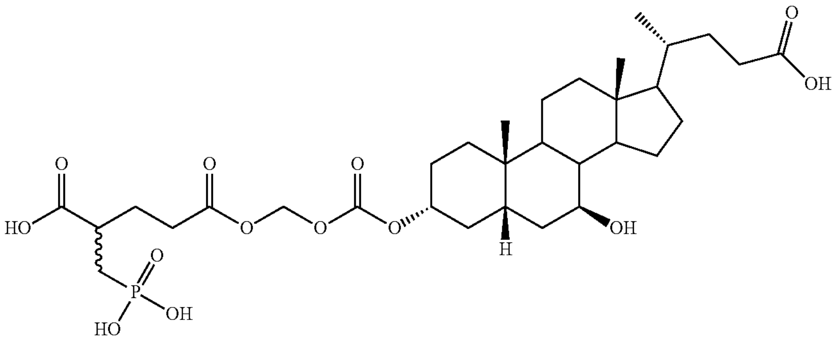 [SMILES: C[C@H](CCC(=O)O)C1CCC2C3C(CC[C@@]21C)[C@@]1(C)CC[C@@H](OC(=O)OCOC(=O)CCC(CP(=O)(O)O)C(=O)O)C[C@H]1C[C@@H]3O] | 674.72 |
| 9 (IS-101-020) | 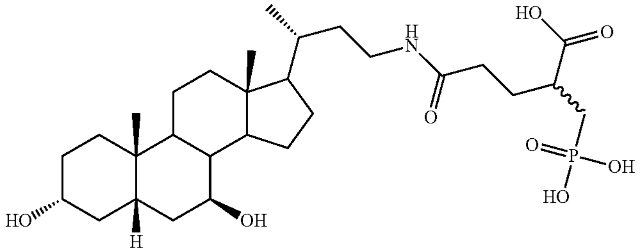 [SMILES: C[C@H](CCNC(=O)CCC(CP(=O)(O)O)C(=O)O)C1CCC2C3C(CC[C@@]21C)[C@@]1(C)CC[C@@H](O)C[C@H]1C[C@@H]3O] | 571.69 |
| 10 (IS-101-077) | 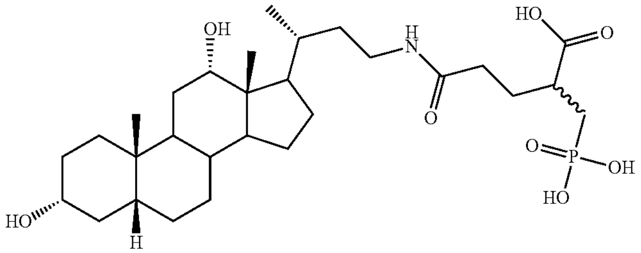 [SMILES: C[C@H](CCNC(=O)CCC(CP(=O)(O)O)C(=O)O)C1CCC2C3CC[C@@H]4C[C@H](O)CC[C@]4(C)C3C[C@H](O)[C@@]21C] | 571.69 |
| 11 (IS-100-026) | 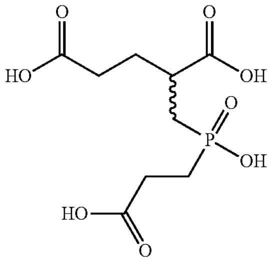 [SMILES: O=C(O)CCC(CP(=O)(O)CCC(=O)O)C(=O)O] | 282.18 |
| 12 (IS-100-058) | 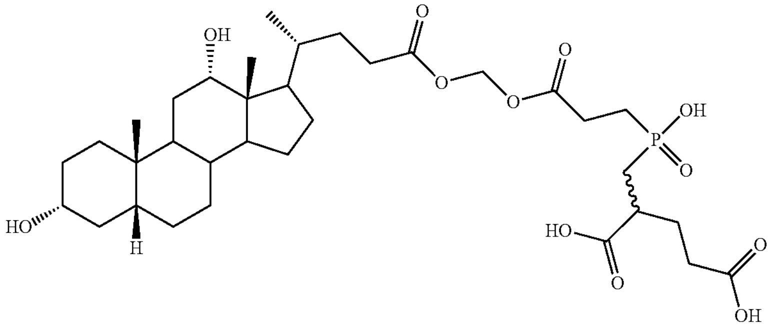 [SMILES: C[C@H](CCC(=O)OCOC(=O)CCP(=O)(O)CC(CCC(=O)O)C(=O)O)C1CCC2C3CC[C@@H]4C[C@H](O)CC[C@]4(C)C3C[C@H](O)[C@@]21C] | 686.78 |

TABLE 2-continued
| Representative Compounds of Formula (I). | | |
|---|---|---|
| Cmpd | Structure | MW |
| 13 (IS-100-032) | 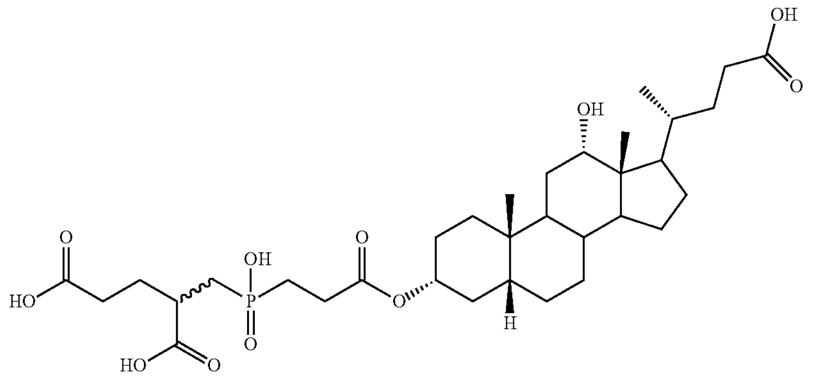 [SMILES: C[C@H](CCC(=O)O)C1CCC2C3CC[C@@H]4C[C@H](OC(=O)CCP(=O)(O)CC(CCC(=O)O)C(=O)O)CC[C@]4(C)C3C[C@H](O)[C@@]21C] | 656.75 |
| 14 (IS-100-085) | 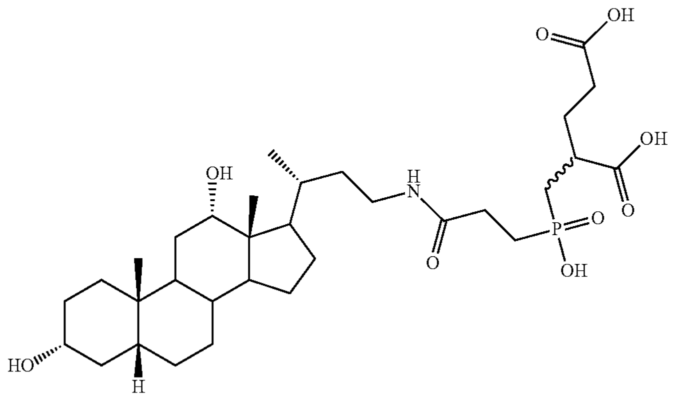 [SMILES: C[C@H](CCNC(=O)CCP(=O)(O)CC(CCC(=O)O)C(=O)O)C1CCC2C3CC[C@@H]4C[C@H](O)CC[C@]4(C)C3C[C@H](O)[C@@]21C] | 627.76 |
| 15 (IS-102-138) | 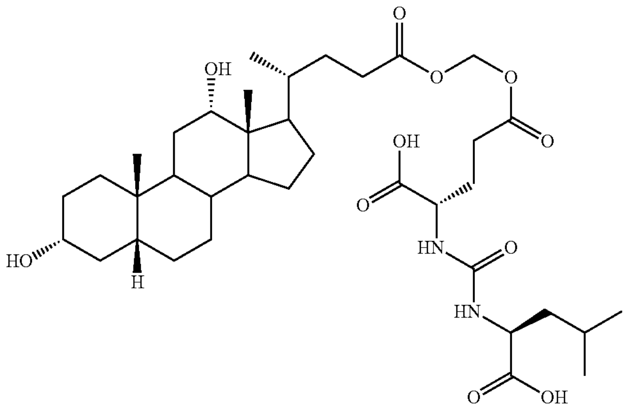 [SMILES: CC(C)C[C@H](NC(=O)N[C@@H](CCC(=O)OCOC(=O)CC[C@@H](C)C1CCC2C3CC[C@@H]4C[C@H](O)CC[C@]4(C)C3C[C@H](O)[C@@]21C)C(=O)O)C(=O)O] | 708.89 |
| 16 (TT-220420) | 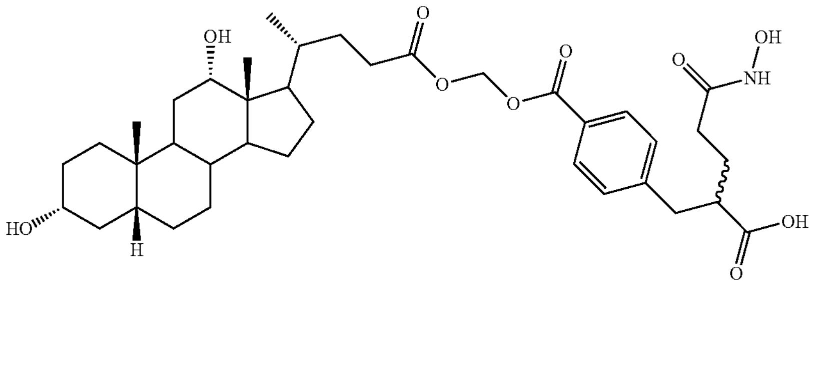 [SMILES: C[C@H](CCC(=O)OCOC(=O)c1ccc(CC(CCC(=O)NO)C(=O)O)cc1)C1CCC2C3CC[C@@H]4C[C@H](O)CC[C@]4(C)C3C[C@H](O)[C@@]21C] | 685.86 |

TABLE 2-continued

Representative Compounds of Formula (I).

| Cmpd | Structure | MW |
|---|---|---|
| A | 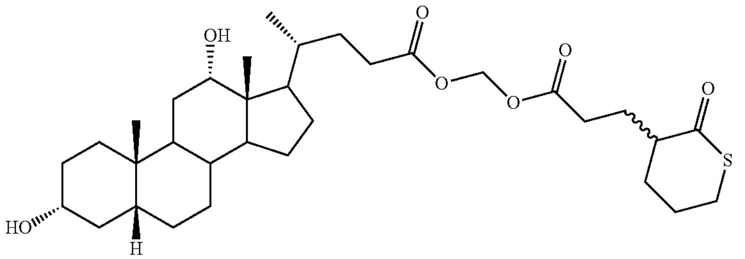 [SMILES: C[C@H](CCC(=O)OCOC(=O)CCC1CCCSC1=O)C1CCC2C3CC[C@@H]4C[C@H](O)CC[C@]4(C)C3C[C@H](O)[C@@]21C] | 592.83 |
| B | 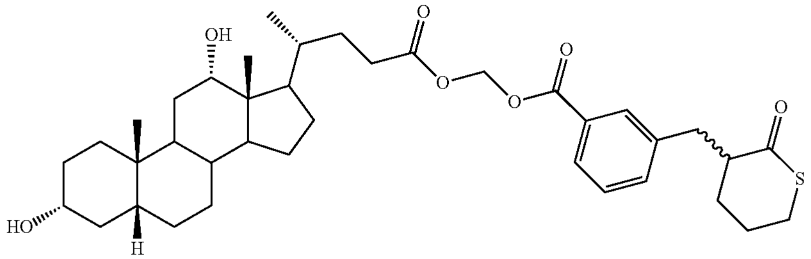 [SMILES: C[C@H](CCC(=O)OCOC(=O)c1cccc(CC2CCCSC2=O)c1)C1CCC2C3CC[C@@H]4C[C@H](O)CC[C@]4(C)C3C[C@H](O)[C@@]21C] | 654.90 |

B. Methods of Treating Diseases or Conditions Associated with Elevated GCPII Activity In some embodiments, the presently disclosed subject matter provides a method for treating a disease or condition associated with elevated GCPII activity. In certain embodiments, the disease or condition is inflammatory bowel disease (IBD).

Glutamate Carboxypeptidase II (GCPII) is a metallopeptidase that catalyzes the hydrolysis of N-acetylated aspartate-glutamate (NAAG) to N-acetyl aspartate (NAA) and glutamate and cleaves terminal glutamate moieties sequentially from folate polyglutamate (Ristau et al., 2013; Mesters et al, 2006; Slusher et al, 2013). In certain embodiments, the presently disclosed compounds of formula (I) are GCPII inhibitors. As used herein, a GCPII inhibitor is a molecule that decreases or inhibits the activity of GCPII. The modulation of the activity of GCPII may be detected by use of an assay for the intrinsic N-acetylated alpha-linked acidic dipeptidase (AALADase) activity of GCPII (Tang et al, 2003; Robinson et al 1987: Lupoid et al., 2002; U.S. Patent App. Pub. No. 20110064657). Inhibition curves may be determined using semi-log plots and $IC_{50}$ values determined at the concentration at which enzyme activity was inhibited by 50%.

The GCPII inhibitor may interact with GCPII directly (e.g., via interaction with the binding site of GCPII) or may interact with another molecule that results in a decrease in the activity of GCPII. The binding site of GCPII contains a binuclear zinc ion and two substrate binding pockets, i.e., an S1 (nonpharmacophore) pocket and an S1' (pharmacophore) pocket. The active site also contains a chloride ion in the S1 pocket. In the vicinity of the S1 pocket resides a funnel-shaped tunnel with a depth of approximately 20 Å and a width of 8-9 Å. Similarly, a narrow cavity is present near the S1' pocket.

GCPII activity is markedly elevated in the diseased intestinal mucosa of subjects with IBD. As used herein, the term "elevated GCPII activity" means an increase of GCPII activity in a subject with IBD as compared to the GCPII activity in a subject without IBD, such as an increase of approximately 100%, 200%, 300%, 400%, 500%, 600%, 700%, 800%, 900%, 1000%, or more.

In some embodiments, the presently disclosed subject matter provides methods for inhibiting GCPII activity. In some embodiments, the presently disclosed subject matter provides methods for inhibiting GCPII activity in a subject afflicted with IBD. As used herein, the term "inhibit" means to decrease or diminish GCPII activity in a subject in need thereof. The term "inhibit" also may mean to decrease, suppress, attenuate, diminish, arrest, or stabilize the development or progression of a disease or condition, such as IBD. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder.

In general, using the presently disclosed methods to treat the IBD in a subject results in a decrease in the severity of the IBD. As used herein, the terms "treat," "treating," "treatment," and the like refer to reducing or ameliorating a disease or condition, such as IBD, and/or symptoms associated therewith. It will be appreciated that, although not precluded, treating a disease or condition, such as IBD, does not require that the disorder, condition or symptoms associated therewith be completely eliminated. The term "decrease" is meant to inhibit, suppress, attenuate, diminish, arrest, or stabilize at least one symptom of IBD (e.g., rectal prolapse, gut inflammation, colonic hypertrophy, stool inconsistency, and the like).

IBD has been classified into the broad categories of Crohn's disease and ulcerative colitis. Accordingly, as used herein, "a subject having inflammatory bowel disease" is synonymous with the term "a subject diagnosed with having an inflammatory bowel disease," and means a patient having Crohn's disease or ulcerative colitis. Crohn's disease (regional enteritis) is a disease of chronic inflammation that can involve any part of the gastrointestinal tract. Commonly, the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease: kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine.

Furthermore, linear ulcerations, edema, and inflammation of the intervening tissue lead to a "cobblestone" appearance of the intestinal mucosa, which is distinctive of CD. A hallmark of Crohn's disease is the presence of discrete aggregations of inflammatory cells, known as granulomas, which are generally found in the submucosa. Some Crohn's disease cases display the typical discrete granulomas, while others show nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of Crohn's disease (Rubin and Farber, 1994).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%/6), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In some embodiments, the presently disclosed subject matter is a pharmaceutical composition, comprising at least one compound of general formula (I) alone or in combination with one or more additional therapeutic agents in admixture with a pharmaceutically acceptable excipient.

The one or more additional therapeutic agents can include other agents useful for treating inflammatory bowel disease, including, but not limited to, an anti-inflammatory drug, including, but not limited to, corticosteroids and aminosalicylates, such as mesalamine (Asacol HD, Delzicol, and others), balsalazide (Colazal) and olsalazine (Dipentum); immune system suppressors, including, but not limited to, azathioprine (Azasan, Imuran), mercaptopurine (Purinethol, Purixan), cyclosporine (Gengraf, Neoral, Sandimmune) and methotrexate (Trexall); tumor necrosis factor (TNF)-alpha inhibitors, including, but not limited to, infliximab (Remicade), adalimumab (Humira) and golimumab (Simponi), or other biologics, including, but not limited to, natalizumab (Tysabri), vedolizumab (Entyvio) and ustekinumab (Stelara); an antibiotic, including, but not limited to, ciprofloxacin (Cipro) and metronidazole (Flagyl); an anti-diarrheal medications, such as loperamide (Imodium A-D); a fiber supplement, such as psyllium powder (Metamucil) or methylcellulose (Citrucel); a pain reliever, such as, acetaminophen; and a supplement, including, but not limited to, an iron supplement, a calcium supplement, and a vitamin D supplement.

The term "combination" is used in its broadest sense and means that a subject is administered at least two agents, more particularly a compound of formula (I) and at least one beta-lactam antibiotic and, optionally, one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A+Q_b/Q_B=\text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

C. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

D. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., $-CH_2O-$ is equivalent to $-OCH_2-$; $-C(=O)O-$ is equivalent to $-OC(=O)-$; $-OC(=O)NR-$ is equivalent to $-NRC(=O)O-$, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The symbol  or  denotes the point of attachment of a moiety to the remainder of the molecule.

When a named atom of an aromatic ring or a heterocyclic aromatic ring is defined as being "absent," the named atom is replaced by a direct bond.

The term "hydroxyl" refers to the —OH group.

The term "aryl" means, unless otherwise stated, an aromatic hydrocarbon substituent that can be a single ring or multiple rings (such as from 1 to 3 rings), which are fused together or linked covalently. Non-limiting examples of aryl and heteroaryl groups include phenyl, 1-naphthyl, 2-naphthyl, 4-biphenyl, and the like. The term "arylene" refers to the divalent form of aryl and heteroaryl.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups, such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

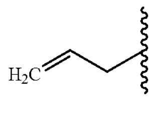

allyl

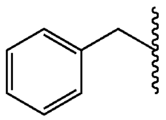

Bn

-continued

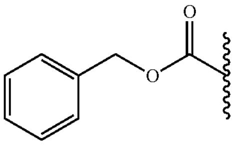

Cbz

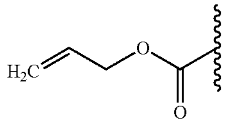

Alloc

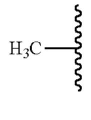

Me

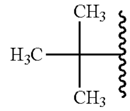

t-butyl

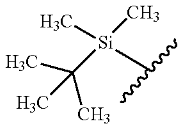

TBDMS

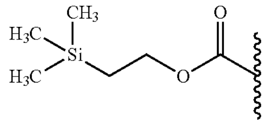

Teoc

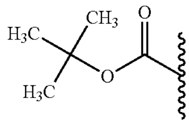

Boc

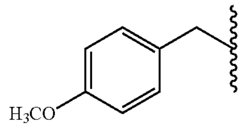

pMB

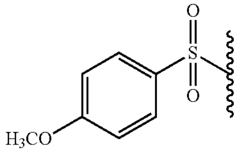

tosyl

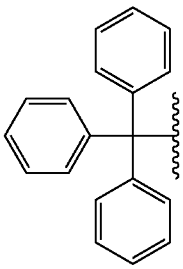

trityl

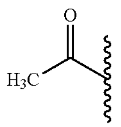

acetyl

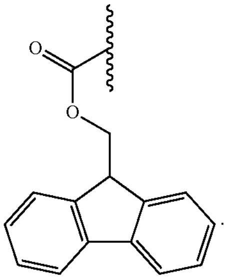

Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Bile Acid-GCPII Inhibitor Conjugates

1.1 Experimental Section

Scheme 1

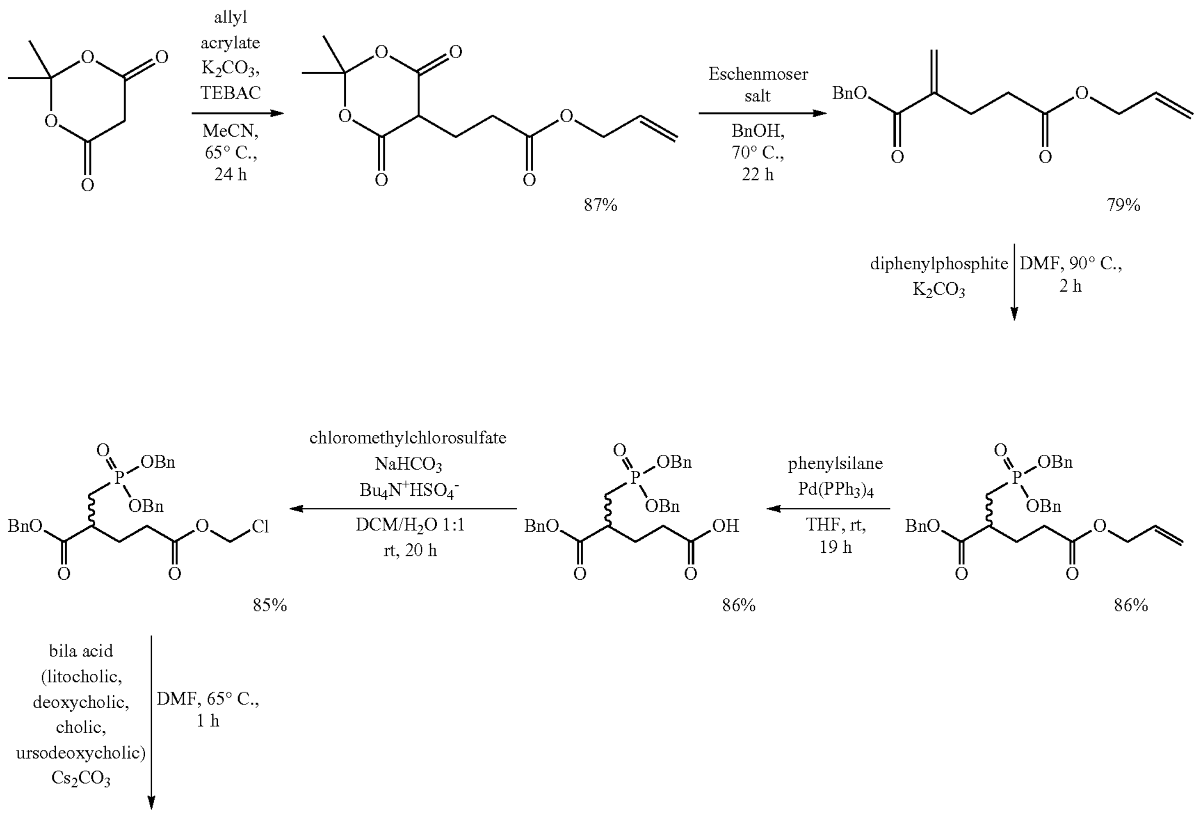

-continued

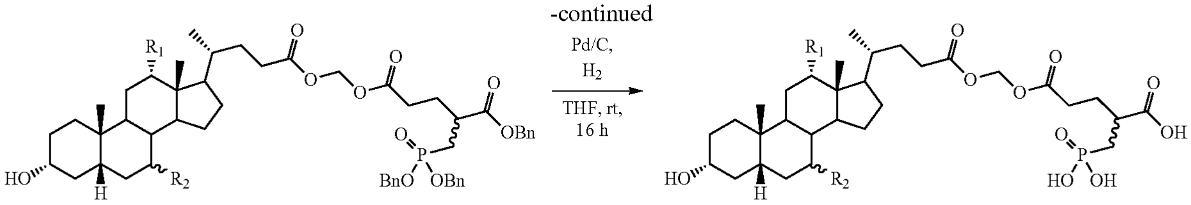

| | | |
|---|---|---|
| litocholic | $R_1$, $R_2$ = H | 73% |
| deoxycholic | $R_1$ = OH, $R_2$ = H | 70% |
| cholic | $R_1$, $R_2$ = OH | 57% |
| ursodeodycholic | $R_1$ = H, $R_2$ = OH | 73% |

| | | |
|---|---|---|
| 1 litocholic | $R_1$, $R_2$ = H | 87% |
| 2 deoxycholic | $R_1$ = OH, $R_2$ = H | 88% |
| 3 cholic | $R_1$, $R_2$ = OH | 97% |
| 4 ursodeodycholic | $R_1$ = H, $R_2$ = OH | 92% |

Allyl-3-(2,2-dimethyl-4,6-dioxo-1,3-dioxan-5-yl) propanoate (LTP487)

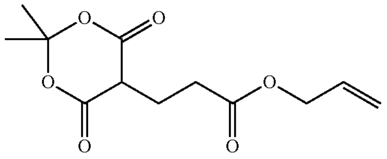 [SMILES: C=CCOC(=O)CCC1C(=O)OC(C)(C)OC1=O]

Compound was prepared according to the published procedure. $^1$H and $^{13}$C NMR spectra were in agreement with published data (WO2016/22827 A1, 2016).

5-Allyl-1-benzyl-2-methylenepentanedioate (LTP491)

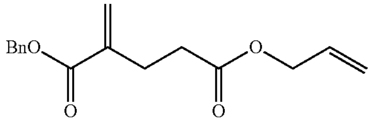 [SMILES: C=CCOC(=O)CCC(=C)C(=O)OCc1ccccc1]

Compound was prepared according to the published procedure. $^1$H and $^{13}$C NMR spectra were in agreement with published data (*Mol. Pharm.* 2017, 14, 3248).

5-Allyl-1-benzyl-2-((diethoxyphosphoryl)methyl) pentanedioate (LTP544)

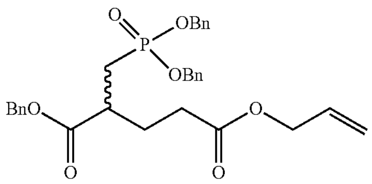 [SMILES: C=CCOC(=O)CCC(CP(=O)(OCc1ccccc1)OCc1ccccc1)C(=O)OCc1ccccc1]

Starting material LTP491 (2.54 g, 9.26 mmol, 1 equiv.) was dissolved in anhydrous DMF (40 mL). Freshly ground $K_2CO_3$ (1.92 g, 13.9 mmol, 1.5 equiv) and solution of dibenzylphosphite (2.55 g, 9.72 mmol, 1.05 equiv.) in anhydrous DMF (5 mL) were added and the resulting mixture was heated to 90° C. for 2 h under inert. DMF was evaporated, EtOAc (100 mL) was added and the organic phase was washed with distilled $H_2O$ (2×50 mL) and brine (50 mL), dried over $MgSO_4$ and solvent was evaporated. The crude product was purified by LC (EtOAc/cyclohexane, 1:1; Rf=0.33; 1% $KMnO_4$ detection) and compound LTP544 was isolated in 86% yield (4.30 g) as a colorless oil.

$^1$H NMR (400 MHz, $CDCl_3$): $\delta_H$ 1.80-2.01 (m, 3H), 2.20-2.40 (m, 3H), 2.84 (dddd, J=19.7, 8.5, 6.9, 5.0 Hz, 1H), 4.52 (dt, J=5.7, 1.4 Hz, 2H), 4.88-5.04 (m, 6H), 5.21 (dq, J=10.4, 1.3 Hz, 1H), 5.27 (dq, J=17.2, 1.5 Hz, 1H), 5.86 (ddt, J=17.2, 10.4, 5.7 Hz, 1H), 7.23-7.38 (m, 15H).

$^{13}$C NMR (101 MHz, $CDCl_3$): $\delta_C$ 28.25 (d, $J_{C,P}$=142.2 Hz), 28.46 (d, $J_{C,P}$=13.3 Hz), 31.30, 39.25 (d, $J_{C,P}$=3.7 Hz), 65.24, 66.79, 67.40 (d, $J_{C,P}$=6.4 Hz), 67.42 (d, $J_{C,P}$=6.3 Hz), 118.34, 128.09-128.66 (15C), 132.11, 135.60, 136.18 (d, $J_{C,P}$=1.8 Hz), 136.24 (d, $J_{C,P}$=1.4 Hz), 172.03, 173.66 (d, $J_{C,P}$=7.9 Hz). $^{31}$P NMR (162 MHz, $CDCl_3$): $\delta_P$ 31.94.

ESI MS: 559.2 ([M+Na]$^+$).

HR ESI MS: calcd for $C_{30}H_{33}O_7PNa$: 559.18561; found: 559.18558.

5-(Benzyloxy)-4-((bis(benzyloxy)phosphoryl) methyl)-5-oxopentanoic acid (LTP560)

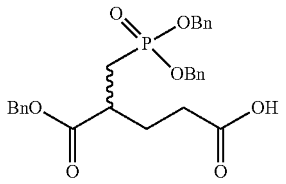 [SMILES: O=C(O)CCC(CP(=O)(OCc1ccccc1)OCc1ccccc1)C(=O)OCc1ccccc1]

Starting material LTP544 (3.60 g, 6.71 mmol, 1 equiv.) was dissolved in anhydrous THF (40 mL). Phenylsilane (1.45 g, 1.65 mL, 13.4 mmol, 2 equiv.) followed by $Pd(PPh_3)_4$ were added (155 mg, 0.134 mmol, 2 mol %) and the reaction mixture was stirred at rt under inert for 19 h. THF was evaporated and the residue was purified by LC ($CHCl_3$/MeOH, 20:1). Compound LTP560 was isolated as a light brown oily compound (2.85 g) in 86% yield.

$^1$H NMR (400 MHz, $CDCl_3$): $\delta_H$ 1.82-1.99 (m, 3H), 2.20-2.37 (m, 3H), 2.84 (dp, J=13.5, 6.8 Hz, 1H), 4.87-5.03 (m, 6H), 7.23-7.36 (m, 15H).

$^{13}$C NMR (101 MHz, $CDCl_3$): $\delta_C$ 28.12 (d, $J_{C,P}$=142.4 Hz), 28.25 (d, $J_{C,P}$=13.0 Hz), 31.13, 39.16 (d, $J_{C,P}$=3.6 Hz), 66.89, 67.68 (d, $J_{C,P}$=2.0 Hz), 67.74 (d, $J_{C,P}$=1.8 Hz), 128.20-128.73 (15C), 135.61, 136.07 (d, $J_{C,P}$=1.6 Hz), 136.13 (d, $J_{C,P}$=1.2 Hz), 173.69 (d, $J_{C,P}$=8.5 Hz), 176.61.

$^{31}$P NMR (162 MHz, $CDCl_3$): $\delta_P$ 32.21.

ESI MS: 519.2 ([M+Na]$^+$).

HR ESI MS: calcd for $C_{27}H_{29}O_7PNa$: 519.15424; found: 519.15431.

1-Benzyl 5-(chloromethyl) 2-((bis(benzyloxy)phosphoryl)methyl)pentanedioate (LTP576)

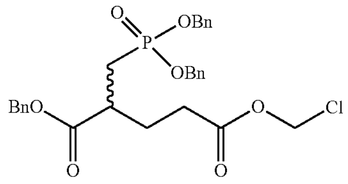 [SMILES: O=C(CCC(CP(=O)(OCc1ccccc1)OCc1ccccc1)C(=O)OCc1ccccc1)OCCl]

Compound LTP560 (1.96 g, 3.95 mmol, 1 equiv.) was dissolved in DCM (30 mL; p.a.), distilled water (30 mL) followed by $NaHCO_3$ (1.26 g, 15.0 mmol, 2.8 equiv.) and $Bu_4N^+HSO_4^-$ (134 mg, 0.395 mmol, 0.1 equiv.) were added. The reaction mixture was vigorously stirred for 5 minutes at rt and finally chloromethyl chlorosulphate (782 mg, 479 μL, 4.74 mmol, 1.2 equiv) in DCM (5 mL) was added during 1 minute. The resulting mixture was stirred for 20 h at rt. Further DCM (20 mL) was added and phases were separated. Water phase was extracted with DCM (50 mL) and combined organic phases were washed with sat. NaCl (50 mL), dried over $MgSO_4$ and DCM was evaporated. The crude product was purified by LC (EtOAc/cyclohexane, 1:1) to afforded the desired product (1.83 g, 85% yield) as a colourless oil.

$^1$H NMR (400 MHz, $CDCl_3$): $\delta_H$ 1.77-2.02 (m, 3H), 2.21-2.38 (m, 3H), 2.82 (dtt, J=13.8, 8.2, 5.6 Hz, 1H), 4.88-5.04 (m, 6H), 5.61 (d, J=0.8 Hz, 2H), 7.22-7.38 (m, 15H).

$^{13}$C NMR (101 MHz, $CDCl_3$): $\delta_C$ 27.87 (d, $J_{C,P}$=12.5 Hz), 28.28 (d, $J_{C,P}$=142.4 Hz), 31.15, 39.10 (d, $J_{C,P}$=3.7 Hz), 66.97, 67.55 (2C, d, $J_{C,P}$=6.4 Hz), 68.73, 128.21-128.76 (15C), 135.58, 136.19 (d, $J_{C,P}$=2.2 Hz), 136.25 (d, $J_{C,P}$=1.9 Hz), 170.60, 173.53 (d, $J_{C,P}$=8.9 Hz).

$^{31}$P NMR (162 MHz, $CDCl_3$): $\delta_P$ 31.95.

ESI MS: 567.1 ([M+Na]$^+$).

HR ESI MS: calcd for $C_{28}H_{30}O_7ClPNa$: 567.13099; found: 567.13081.

1-Benzyl 5-((((4R)-4-((3R,10S,13R)-3-hydroxy-10,13-dimethylhexadecahydro-1H-cyclopenta[a]phenanthren-17-yl)pentanoyl)oxy)methyl) 2-((bis(benzyloxy)phosphoryl) methyl)pentanedioate (LTP578)

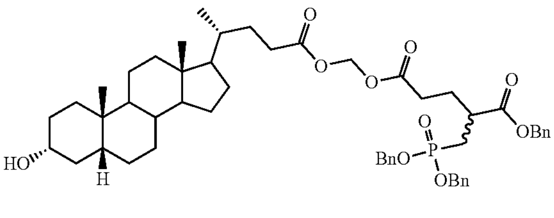 [SMILES: C[C@H](CCC(=O)OCOC(=O)CCC(CP(=O)(OCc1ccccc1)OCc1ccccc1)C(=O)OCc1ccccc1)C1CCC2C3CC[C@@H]4C[C@H](O)CC[C@]4(C)C3CC[C@@]21C]

Compound LTP 576 (500 mg, 0.917 mmol, 1 equiv.), lithocholic acid (690 mg, 1.83 mmol, 2 equiv.) and $Cs_2CO_3$ (330 mg, 1.01 mmol, 1.1 equiv.) were dissolved/suspended in anhydrous DMF (30 mL). The resulting mixture was heated to 65° C. (block) under inert atmosphere for 1 h. DMF was evaporated, the residue was dissolved in EtOAc (100 mL) and washed with dist. $H_2O$ (50 mL), sat. $NaHCO_3$ (50 mL), dist. $H_2O$ (50 mL) and sat. NaCl (50 mL), dried over $MgSO_4$ and solvent was evaporated. The crude product was purified by LC (EtOAc/cyclohexane, 2:1) and compound LTP578 was obtained as a colorless amorphous foam (592 mg, 73% yield).

$^1$H NMR (400 MHz, $CDCl_3$): $\delta_H$ 0.63 (s, 3H), 0.89 (d, J=6.4 Hz, 3H), 0.91 (s, 3H), 0.94-1.18 (m, 6H), 1.18-1.45 (m, 15H), 1.44-1.69 (m, 2H), 1.70-1.87 (m, 5H), 1.87-1.98 (m, 3H), 2.17-2.44 (m, 4H), 2.75-2.87 (m, 1H), 3.61 (tt, J=10.9, 4.6 Hz, 1H), 4.85-5.04 (m, 6H), 5.64-5.70 (m, 2H), 7.21-7.39 (m, 15H).

$^{13}$C NMR (101 MHz, $CDCl_3$): $\delta_C$ 12.13, 18.33, 20.89, 23.47, 24.27, 26.50, 27.28, 28.00 (d, $J_{C,P}$=13.0 Hz), 28.24 (d, $J_{C,P}$=142.3 Hz), 28.26, 29.78, 30.63 (d, $J_{C,P}$=3.4 Hz), 30.96, 31.06, 34.65, 35.34, 35.44, 35.91, 36.52, 39.13 (d, $J_{C,P}$=3.7 Hz), 40.23, 40.49, 42.16, 42.81, 55.95, 56.55, 66.88, 67.46 (d, $J_{C,P}$=1.1 Hz), 67.52 (d, $J_{C,P}$=1.1 Hz), 71.85, 79.23, 128.14-128.69 (15C), 135.56, 136.15 (d, $J_{C,P}$=2.0 Hz), 136.21 (d, $J_{C,P}$=1.6 Hz), 171.23, 172.95, 173.53 (d, $J_{C,P}$=8.3 Hz).

$^{31}$P NMR (162 MHz, $CDCl_3$): $\delta_P$ 31.82.

ESI MS: 907.4 ([M+Na]$^+$).

HR ESI MS: calcd for $C_{52}H_{70}O_{10}P$: 885.47011; found: 885.47038.

1-Benzyl 5-((((4R)-4-((3R,10S,12S,13R)-3,12-dihydroxy-10,13-dimethylhexadecahydro-1H-cyclopenta[a]phenanthren-17 -yl)pentanoyl)oxy)methyl) 2-((bis(benzyloxy) phosphoryl)methyl)pentanedioate (LTP589)

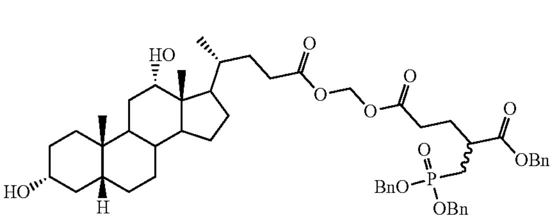 [SMILES: C[C@H](CCC(=O)OCOC(=O)CCC(CP(=O)(OCc1ccccc1)OCc1ccccc1)C(=O)OCc1ccccc1)C1CCC2C3CC[C@@H]4C[C@H](O)CC[C@]4(C)C3C[C@H](O)[C@@]21C]

Compound LTP 576 (500 mg, 0.917 mmol, 1 equiv.), deoxycholic acid (720 mg, 1.83 mmol, 2 equiv.) and $Cs_2CO_3$ (330 mg, 1.01 mmol, 1.1 equiv.) were dissolved/suspended in anhydrous DMF (40 mL). The resulting mixture was heated to 60° C. (block) under inert atmosphere for 1 h. DMF was evaporated, the residue was dissolved in EtOAc (150 mL) and washed with sat. $NaHCO_3$ (100 mL), dist. $H_2O$ (100 mL) and sat. NaCl (100 mL), water phases were reextracted with EtOAc (100 mL), combined and dried over $MgSO_4$. EtOAc was evaporated. The crude product was purified by LC (gradient: EtOAc/cyclohexane, 2:1 to EtOAc) and compound LTP589 was obtained as a colorless amorphous foam (579 mg, 70% yield).

$^1$H NMR (400 MHz, $CDCl_3$): $\delta_H$ 0.66 (s, 3H), 0.90 (s, 3H), 0.95 (d, J=6.2 Hz, 3H), 0.98-1.18 (m, 2H), 1.19-1.46 (m, 11H), 1.46-2.00 (m, 14H), 2.18-2.45 (m, 5H), 2.81 (dddd, J=13.1, 11.3, 10.0, 6.0 Hz, 1H), 3.59 (tt, J=11.0, 4.6 Hz, 1H), 3.95 (t, J=3.0 Hz, 1H), 4.86-5.03 (m, 6H), 5.64-5.72 (m, 2H), 7.19-7.38 (m, 15H).

$^{13}$C NMR (101 MHz, $CDCl_3$): $\delta_C$ 12.84, 17.37, 23.26, 23.74, 26.23, 27.22, 27.54, 28.02 (d, $J_{C,P}$=13.0 Hz), 28.25 (d, $J_{C,P}$=143.0 Hz), 28.82, 29.80, 30.57, 31.02, 31.09, 33.74, 34.21, 35.15, 35.33, 36.12, 36.52, 39.16 (d, $J_{C,P}$=3.7 Hz), 42.17, 46.59, 47.26, 48.33, 66.91, 67.48 (d, $J_{C,P}$=2.0 Hz), 67.55 (d, $J_{C,P}$=1.9 Hz), 71.85, 73.14, 79.26, 135.57, 136.17

(d, $J_{C,P}$=1.9 Hz), 136.23 (d, $J_{C,P}$=1.5 Hz), 128.16-128.72 (15C), 171.27, 172.94, 173.58 (d, $J_{C,P}$=8.4 Hz).

$^{31}$P NMR (162 MHz, $CDCl_3$): $\delta_P$ 32.04.

ESI MS: 923.4 ([M+Na]$^+$).

HR ESI MS: calcd for $C_{52}H_{69}O_{11}PNa$: 923.44697; found: 923.44706.

1-Benzyl 5-((((4R)-4-((3R,7R,10S,12S,13R)-3,7,12-trihydroxy-10,13-dimethylhexadecahydro-1H-cyclopenta[a]phenanthren-17-yl)pentanoyl)oxy)methyl) 2-((bis(benzyloxy)phosphoryl)methyl)pentanedioate (LTP584)

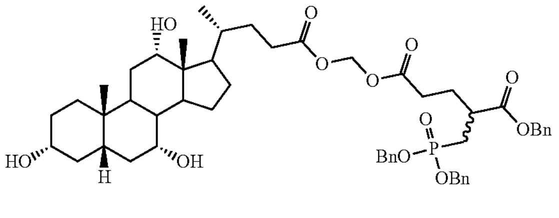 [SMILES: C[C@H](CCC(=O)OCOC(=O)CCC(CP(=O)(OCc1ccccc1)OCc1ccccc1)C(=O)OCc1ccccc1)C1CCC2C3C(C[C@H](O)[C@@]21C)[C@@]1(C)CC[C@@H](O)C[C@H]1C[C@H]3O]

Compound LTP 576 (500 mg, 0.917 mmol, 1 equiv.), cholic acid (750 mg, 1.83 mmol, 2 equiv.) and $Cs_2CO_3$ (330 mg, 1.01 mmol, 1.1 equiv.) were dissolved/suspended in anhydrous DMF (40 mL). The resulting mixture was heated to 65° C. (block) under inert atmosphere for 1 h. DMF was evaporated, the residue was suspended in the mixture of solvents EtOAc (150 mL) and MeOH (20 mL), stirred for 10 minutes, filtrated and solvents were evaporated. The crude product was purified by LC (EtOAc/MeOH, 10:1) and compound LTP584 was obtained as a colorless amorphous foam (479 mg, 57% yield).

$^1$H NMR (400 MHz, $CDCl_3$): $\delta_H$ 0.67 (s, 3H), 0.88 (s, 3H), 0.96 (d, J=6.0 Hz, 3H), 0.92-1.02 (m, 1H), 1.11 (qd, J=12.0, 5.8 Hz, 1H), 1.19-2.08 (m, 22H), 2.12-2.48 (m, 6H), 2.74-2.86 (m, 1H), 3.39-3.47 (m, 1H), 3.83 (q, J=3.1 Hz, 1H), 3.91-4.02 (m, 1H), 4.85-5.05 (m, 6H), 5.65-5.71 (m, 2H), 7.19-7.38 (m, 15H).

$^{13}$C NMR (101 MHz, $CDCl_3$): $\delta_C$ 12.62, 17.41, 22.61, 23.32, 26.59, 27.58, 28.07 (d, $J_{C,P}$=13.1 Hz), 28.26 (d, $J_{C,P}$=141.7 Hz), 28.38, 29.82, 30.59, 31.02, 31.11, 34.77, 34.85, 35.27, 35.37, 39.18 (d, $J_{C,P}$=3.9 Hz), 39.65, 39.74, 41.58, 41.89, 46.58, 47.05, 66.94, 67.52 (d, $J_{C,P}$=2.8 Hz), 67.58 (d, $J_{C,P}$=2.6 Hz), 68.52, 72.03, 73.07, 79.27, 128.18-128.74 (15C), 135.58, 136.18 (d, $J_{C,P}$=1.8 Hz), 136.24 (d, $J_{C,P}$=1.6 Hz), 171.31, 173.01, 173.60 (d, $J_{C,P}$=8.4 Hz).

$^{31}$P NMR (162 MHz, $CDCl_3$): $\delta_P$ 32.04.

ESI MS: 939.4 ([M+Na]$^+$).

HR ESI MS: calcd for $C_{52}H_{69}O_{12}PNa$: 939.44189; found: 939.44177.

1-Benzyl 5-((((4R)-4-((3R,7S,10S,13R)-3,7-dihydroxy-10,13-dimethylhexadecahydro-1H-cyclopenta[a]phenanthren-17-yl)pentanoyl)oxy)methyl) 2-((bis(benzyloxy)phosphoryl) methyl)pentanedioate

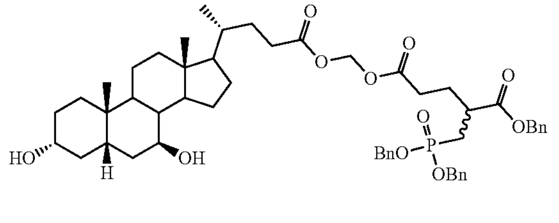 [SMILES: C[C@H](CCC(=O)OCOC(=O)CCC(CP(=O)(OCc1ccccc1)OCc1ccccc1)C(=O)OCc1ccccc1)C1CCC2C3C(CC[C@@]21C)[C@@]1(C)CC[C@@H](O)C[C@H]1C[C@@H]3O]

Compound LTP 576 (500 mg, 0.917 mmol, 1 equiv.), ursodeoxycholic acid (720 mg, 1.83 mmol, 2 equiv.) and $Cs_2CO_3$ (330 mg, 1.01 mmol, 1.1 equiv.) were dissolved/suspended in anhydrous DMF (30 mL). The resulting mixture was heated to 65° C. (block) under inert atmosphere for 1 h. DMF was evaporated, the residue was dissolved in EtOAc (150 mL), washed with sat. $NaHCO_3$ (100 mL), dist. $H_2O$ (100 mL) and sat. NaCl (100 mL), water phases were reextracted with EtOAc (100 mL), organic phases were combined and dried over $MgSO_4$. EtOAc was evaporated. The crude product was purified by LC (EtOAc/cyclohexane, 2:1) and compound LTP1049 was obtained as a colorless amorphous foam (605 mg, 73% yield).

$^1$H NMR (400 MHz, $CDCl_3$): $\delta_H$ 0.69 (s, 3H), 0.94 (d, J=6.3 Hz, 3H), 0.97 (s, 3H), 0.98-1.23 (m, 4H), 1.22-1.74 (m, 14H), 1.76-2.05 (m, 8H), 2.19-2.50 (m, 6H), 2.84 (dddd, J=13.4, 11.2, 8.2, 5.6 Hz, 1H), 3.55-3.67 (m, 2H), 4.89-5.06 (m, 6H), 5.70 (qd, J=5.6, 2.6 Hz, 2H), 7.24-7.42 (m, 15H).

$^{13}$C NMR (101 MHz, $CDCl_3$): $\delta_C$ 12.25, 18.47, 21.28, 23.50, 27.00, 28.02 (d, $J_{C,P}$=12.9 Hz), 28.26 (d, $J_{C,P}$=142.3 Hz), 28.73, 30.44, 30.72, 31.03, 31.08 (2C), 34.18, 35.05, 35.28, 37.04, 37.41, 39.16 (d, $J_{C,P}$=3.1 Hz), 39.27, 40.23, 42.56, 43.85, 54.94, 55.84, 66.91, 67.49 (d, $J_{C,P}$=1.7 Hz), 67.55 (d, $J_{C,P}$=1.6 Hz), 71.39, 71.50, 79.25, 128.16-128.72 (15C), 135.57, 136.16 (d, $J_{C,P}$=2.0 Hz), 136.22 (d, $J_{C,P}$=1.6 Hz), 171.26, 172.91, 173.56 (d, $J_{C,P}$=8.4 Hz).

$^{31}$P NMR (162 MHz, $CDCl_3$): $\delta_P$ 32.03.

ESI MS: 923.4 ([M+Na]$^+$).

HR ESI MS: calcd for $C_{52}H_{69}O_{11}PNa$: 923.44697; found: 923.44773.

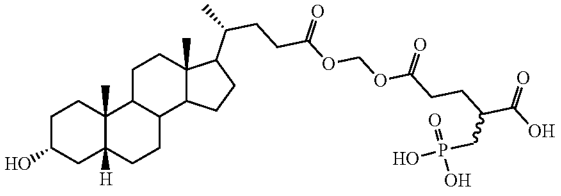 [SMILES: C[C@H](CCC(=O)OCOC(=O)CCC(CP(=O)(O)O)C(=O)O)C1CCC2C3CC[C@@H]4C[C@H](O)CC[C@]4(C)C3CC[C@@]21C]

5-((((4R)-4-((3R,10S,13R)-3-Hydroxy-10,13-dimethylhexadecahydro-1H-cyclopenta[a]phenanthren-17-yl)pentanoyl)oxy)methoxy)-5-oxo-2-(phosphonomethyl)pentanoic acid (1, LTP582)

Compound LTP578 (380 mg, 0.429 mmol, 1 equiv.) was dissolved in anhydrous THF (10 mL), 10% Pd/C (137 mg, 0.129 mmol, 0.3 equiv.) was added and the reaction mixture was saturated with $H_2$ and stirred under $H_2$ atmosphere (balloon) overnight (20 h). Pd/C was removed by filtration and washed with further THF (2×10 mL). Solvent was evaporated and the residue was dissolved in $MeCN/H_2O$ 2:1 (60 mL), cooled to −78° C. and lyophilized overnight. Desired product 1 was afforded as a colourless foam (230 mg, 87% yield).

$^1$H NMR (400 MHz, $d_6$-DMSO): $\delta_H$ 0.60 (s, 3H), 0.86 (d, J=6.2 Hz, 3H), 0.87 (s, 3H), 0.82-0.93 (m, 1H), 0.96-1.41 (m, 18H), 1.44-1.99 (m, 8H), 2.05-2.10 (m, 1H), 2.17-2.44 (m, 4H), 2.51-2.63 (m, 2H), 3.36 (tt, J=10.4, 4.5 Hz, 1H), 5.63-5.69 (m, 2H), 4.17-6.97 (bs, 4H).

$^{13}$C NMR (101 MHz, $d_6$-DMSO): $\delta_C$ 11.87, 18.06, 20.43, 23.31, 23.87, 26.92, 26.94 (d, $J_{C,P}$=154.3 Hz), 27.17 (d, $J_{C,P}$=9.5 Hz), 27.71, 28.93, 30.25, 30.30, 30.40, 30.44, 30.89, 34.23, 34.72, 35.18, 35.39, 36.31, 39.02 (d, $J_{C,P}$=2.9

Hz), 39.99, 41.56, 42.30, 55.46, 56.07, 69.89, 78.94, 171.37, 172.25, 175.54 (d, $J_{C,P}$=10.0 Hz).

$^{31}$P NMR (162 MHz, $d_6$-DMSO): $\delta_P$ 25.84.

ESI MS: 613.4 ([M−H]$^+$).

HR ESI MS: calcd for $C_{31}H_{50}O_{10}P$: 613.31471; found: 613.31474.

5-((((4R)-4-((3R,10S,12S,13R)-3,12-Dihydroxy-10, 13-dimethylhexadecahydro-1H-cyclopenta[a] phenanthren-7-yl)pentanoyl)oxy)methoxy)-5-oxo-2-(phosphonomethyl) pentanoic acid (2, LTP592)

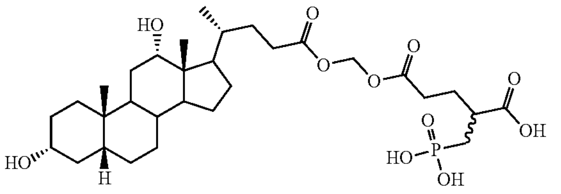 [SMILES: C[C@H](CCC(=O)OCOC(=O)CCC(CP(=O)(O)O)C(=O)O)C1CCC2C3CC[C@@H]4C[C@H](O)CC[C@]4(C)C3C[C@H](O)[C@@]21C]

Compound LTP589 (437 mg, 0.485 mmol, 1 equiv.) was dissolved in anhydrous THF (12 mL), 10% Pd/C (155 mg, 0.145 mmol, 0.3 equiv.) was added and the reaction mixture was saturated with $H_2$ and stirred under $H_2$ atmosphere (balloon) overnight (16 h). Pd/C was removed by filtration and washed with further THF (2×10 mL). Solvent was evaporated and the residue was dissolved in MeCN/$H_2O$ 2:1 (60 mL), cooled to −78° C. and lyophilized overnight. Desired product 2 was afforded as a colourless foam (270 mg, 88% yield).

$^1$H NMR (400 MHz, $CD_3OD$): $\delta_H$ 0.71 (s, 3H), 0.93 (s, 3H), 1.00 (d, J=6.4, 3H), 1.07-1.23 (m, 2H), 1.24-1.55 (m, 12H), 1.56-1.64 (m, 2H), 1.74-2.10 (m, 11H), 2.11-2.23 (m, 1H), 2.30 (ddd, J=15.7, 8.7, 7.1, 1H), 2.37-2.53 (m, 3H), 2.76 (ddt, J=13.5, 11.3, 6.7, 1H), 3.47-3.57 (m, 1H), 3.95 (t, J=2.7, 1H), 5.72 (d, J=5.7, 1H), 5.74 (d, J=5.7, 1H).

$^{13}$C NMR (101 MHz, $CD_3OD$): $\delta_C$ 13.22, 17.50, 23.72, 24.85, 27.44, 28.61, 28.88 (d, $J_{C,P}$=10.4 Hz), 29.13 (d, $J_{C,P}$=149.7 Hz), 29.49, 30.90, 31.04, 31.76, 31.85, 32.12, 34.79, 35.29, 36.43, 36.57, 37.17, 37.41, 40.62 (d, $J_{C,P}$=3.1 Hz), 43.60, 47.55, 48.07, 49.26, 72.53, 74.01, 80.41, 172.96, 174.26, 177.70 (d, $J_{C,P}$=10.0 Hz).

$^{31}$P NMR (162 MHz, $CD_3OD$): $\delta_P$ 28.43.

ESI MS: 629.4 ([M−H]$^+$).

HR ESI MS: calcd for $C_{31}H_{50}O_{11}P$: 629.30962; found: 629.30990.

5-Oxo-2-(phosphonomethyl)-5-((((4R)-4-((3R,7R, 10S,12S,13R)-3,7,12-trihydroxy-10,13-dimethyl-hexadecahydro-1H-cyclopenta[a]phenanthren-17-yl) pentanoyl)oxy)methoxy) pentanoic acid (3, LTP588)

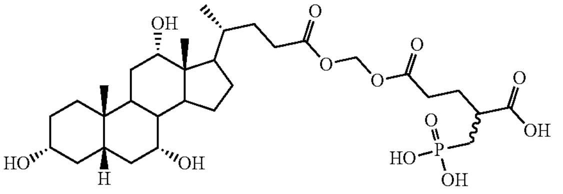 [SMILES: C[C@H](CCC(=O)OCOC(=O)CCC(CP(=O)(O)O)C(=O)O)C1CCC2C3C(C[C@H](O)[C@@]21C)[C@@]1(C)CC[C@@H](O)C[C@H]1C[C@H]3O]

Compound LTP586 (444 mg, 0.484 mmol, 1 equiv.) was dissolved in anhydrous THF (12 mL), 10% Pd/C (155 mg, 0.145 mmol, 0.3 equiv.) was added and the reaction mixture was saturated with $H_2$ and stirred under $H_2$ atmosphere (balloon) overnight (20 h). Pd/C was removed by filtration and washed with further THF (2×10 mL). Solvent was evaporated and the residue was dissolved in MeCN/$H_2O$ 2:1 (60 mL), cooled to −78° C. and lyophilized overnight. Desired product 3 was afforded as a colourless foam (305 mg, 97% yield).

$^1$H NMR (400 MHz, $CD_3OD$): $\delta_H$ 0.71 (s, 3H), 0.92 (s, 3H), 1.00 (d, J=6.4 Hz, 3H), 0.96-1.04 (m, 1H), 1.05-1.20 (m, 1H), 1.22-1.69 (m, 12H), 1.70-2.08 (m, 9H), 2.08-2.54 (m, 7H), 2.67-2.82 (m, 1H), 3.32-3.42 (m, 1H), 3.80 (q, J=3.1 Hz, 1H), 3.91-3.98 (m, 1H), 5.70-5.76 (m, 2H).

$^{13}$C NMR (101 MHz, $d_6$-DMSO): $\delta_C$ 12.34, 16.87, 22.66, 22.83, 26.23, 27.26 (d, $J_{C,P}$=5.5 Hz), 27.29, 27.84 (d, $J_{C,P}$=139.9 Hz), 28.53, 28.92, 30.27, 30.38, 30.43, 30.89, 34.41, 34.89, 34.96, 35.34, 39.02 (d, $J_{C,P}$=3.0 Hz), 39.60, 41.40, 41.55, 45.80, 46.07, 66.27, 70.47, 71.01, 78.94, 171.39, 172.34, 175.54 (d, $J_{C,P}$=9.9 Hz).

$^{31}$P NMR (162 MHz, $CD_3OD$): $\delta_P$ 25.64.

ESI MS: 669.4 ([M+Na]$^+$).

HR ESI MS: calcd for $C_{31}H_{51}O_{12}PNa$: 669.30103; found: 669.30121.

5-((((4R)-4-((3R,7S,12S,13R)-3,12-Dihydroxy-10, 13-dimethylhexadecahydro-1H-cyclopenta[a] phenanthren-17-yl)pentanoyl)oxy)methoxy)-5-oxo-2-(phosphonomethyl) pentanoic acid (4, LTP1054)

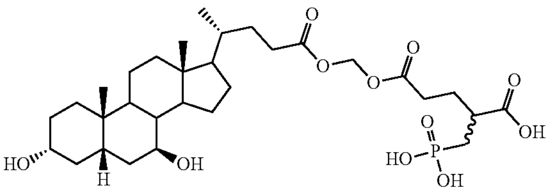 [SMILES: C[C@H](CCC(=O)OCOC(=O)CCC(CP(=O)(O)O)C(=O)O)C1CCC2C3C(CC[C@@]21C)[C@@]1(C)CC[C@@H](O)C[C@H]1C[C@@H]3O]

Compound LTP1048 (960 mg, 1.07 mmol, 1 equiv.) was dissolved in anhydrous THF (25 mL), 10% Pd/C (113 mg, 0.107 mmol, 0.1 equiv.) was added and the reaction mixture was saturated with $H_2$ and stirred under $H_2$ atmosphere (balloon) overnight (24 h). Pd/C was removed by filtration and washed with further THF (2×20 mL). Solvent was evaporated and the residue was dissolved in MeCN/$H_2O$ 2:1 (120 mL), cooled to −78° C. and lyophilized overnight. Desired product 4 was afforded as a colourless foam (618 mg, 92% yield).

$^1$H NMR (400 MHz, $CD_3OD$): $\delta_H$ 0.71 (s, 3H), 0.95 (d, J=6.9 Hz, 3H), 0.97 (s, 3H), 0.98-1.68 (m, 19H), 1.75-2.11 (m, 7H), 2.11-2.54 (m, 5H), 2.69-2.83 (m, 1H), 3.40-3.55 (m, 2H), 5.73 (q, J=5.7 Hz, 2H).

$^{13}$C NMR (101 MHz, $CD_3OD$): $\delta_C$ 12.68, 18.87, 22.39, 23.95, 27.94, 28.90 (d, $J_{C,P}$=10.5 Hz), 29.63, 30.18 (d, $J_{C,P}$=139.8 Hz), 31.02, 31.80, 31.94, 32.12, 35.17, 36.09, 36.55, 37.98, 38.59, 40.62 (d, $J_{C,P}$=3.0 Hz), 40.70, 41.54, 44.02, 44.45, 44.79, 56.48, 57.47, 71.95, 72.12, 80.41, 172.93, 174.19, 177.65 (d, $J_{C,P}$=10.1 Hz).

$^{31}$P NMR (162 MHz, $CD_3OD$): $\delta_P$ 28.43.

ESI MS: 629.4 ([M−H]$^+$).

HR ESI MS: calcd for $C_{31}H_{50}O_{11}P$: 629.30962; found: 629.30990.

Scheme 2

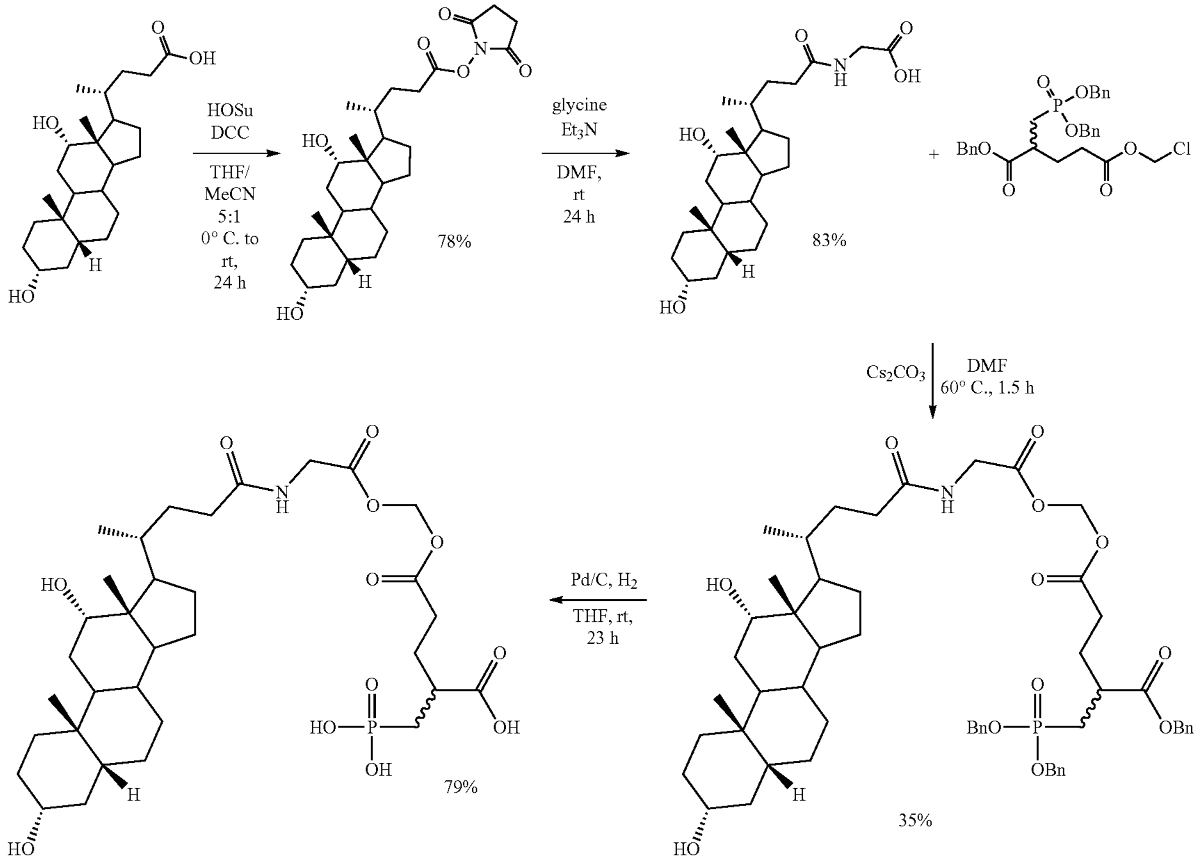

5

2,5-Dioxopyrrolidin-1-yl (4R)-4-((3R,10S,12S,13R)-3,12-dihydroxy-10,13-dimethylhexadecahydro-1H-cyclopenta[a]phenanthren-17-yl)pentanoate (LTP765)

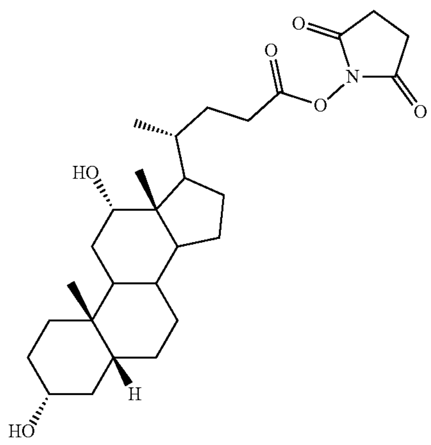 [SMILES: C[C@H](CCC(=O)ON1C(=O)CCC1=O)C1CCC2C3CC[C@@H]4C[C@H](O)CC[C@]4(C)C3C[C@H](O)[C@@]21C]

Compound was prepared according to the published procedure. $^{1}H$ and $^{13}C$ NMR spectra were in agreement with published data (*Bioorg. Med. Chem. Lett.* 2004, 14, 773).

((4R)-4-((3R,1S,12S,13R)-3,12-Dihydroxy-10,13-dimethylhexadecahydro-1H-cyclopenta[a]phenanthren-17-yl)pentanoyl)glycine (LTP773)

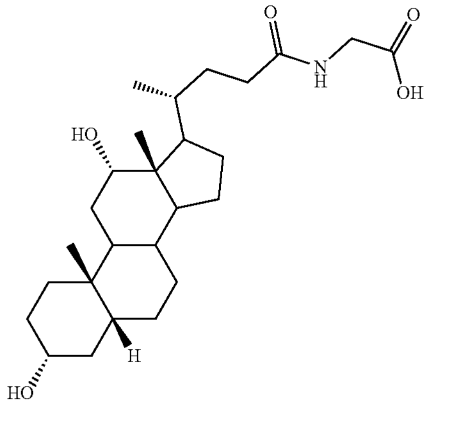 [SMILES: C[C@H](CCC(=O)NCC(=O)O)C1CCC2C3CC[C@@H]4C[C@H](O)CC[C@]4(C)C3C[C@H](O)[C@@]21C]

Compound was prepared according to the published procedure. $^{1}H$ and $^{13}C$ NMR spectra were in agreement with published data (*Lett. Drug Des. Discov.* 2012, 9, 573).

1-Benzyl 5-(((((4R)-4-((3R,10S,12S,13R)-3,12-dihydroxy-10,13-dimethylhexadecahydro-1H-cyclopenta[a]phenanthren-17-yl)pentanoyl)glycyl)oxy)methyl) 2-((bis(benzyloxy) phosphoryl)methyl) pentanedioate (LTP781)

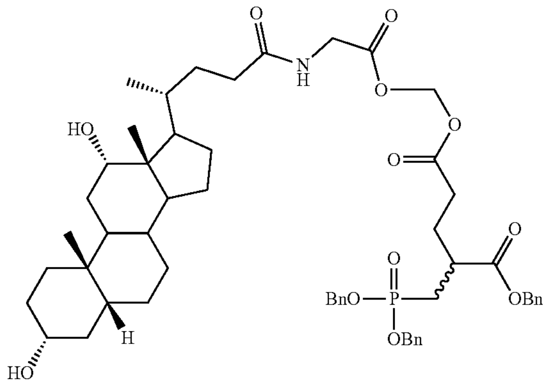 [SMILES: C[C@H](CCC(=O)NCC(=O)OCOC(=O)CCC(CP(=O)(OCc1ccccc1)OCc1ccccc1)C(=O)OCc1ccccc1)C1CCC2C3CC[C@@H]4C[C@H](O)CC[C@]4(C)C3C[C@H](O)[C@@]21C]

Compound LTP773 (300 mg, 0.667 mmol, 1.5 equiv.), compound LTP576 (242 mg, 0.445 mmol, 1 equiv.) and $Cs_2CO_3$ (159 mg, 0.489 mmol, 1.1 equiv) were dissolved in anhydrous DMF (12 mL) and the resulting mixture was heated to 60° C. for 1.5 h. The inorganic precipitate was filtered off and washed with EtOAc (20 mL). Organic solvents were evaporated. The crude product was purified by LC (EtOAc/MeOH, 20:1) to afforded compound LTP781 as a colorless amorphous solid in 35% yield (150 mg).

$^1$H NMR (400 MHz, $CDCl_3$): $\delta_H$ 0.68 (s, 3H), 0.91 (s, 3H), 0.99 (d, J=5.9 Hz, 3H), 0.94-1.18 (m, 2H), 1.21-1.34 (m, 2H), 1.34-2.04 (m, 20H), 2.17 (ddd, J=14.9, 9.1, 6.3 Hz, 1H), 2.23-2.42 (m, 4H), 2.72-2.88 (m, 4H), 3.62 (tt, J=10.5, 4.6 Hz, 1H), 3.97 (d, J=3.2 Hz, 1H), 4.06 (t, J=6.3 Hz, 2H), 4.96 (dt, J=20.3, 12.0 Hz, 6H), 5.74 (s, 2H), 6.39 (t, J=5.5 Hz, 1H), 7.22-7.40 (m, 15H).

$^{13}$C NMR (101 MHz, $CDCl_3$): $\delta_C$ 12.86, 17.51, 23.27, 23.77, 26.26, 27.24, 27.59, 28.13 (d, J=13.4 Hz), 28.19 (d, J=142.4 Hz), 28.76, 30.54, 31.11, 31.51, 33.07, 33.76, 34.23, 35.29, 35.34, 36.12, 36.49, 39.06 (d, J=3.5 Hz), 41.14, 42.18, 46.61, 47.19, 48.36, 66.99, 67.65 (d, J=3.5 Hz), 67.71 (d, J=3.3 Hz), 71.92, 73.25, 79.47, 128.17-128.76 (15C), 135.52, 136.04 (d, J=1.1 Hz), 136.10 (d, J=1.2 Hz), 169.22, 171.07, 173.55 (d, J=7.0 Hz), 174.20.

$^{31}$P NMR (162 MHz, $CDCl_3$): $\delta_P$ 32.03.

ESI MS: 980.6 ($[M+Na]^+$).

HR ESI MS: calcd for $Cs_4H_{72}O_{12}NPNa$: 980.46843; found: 980.46883.

5-(((((4R)-4-((3R,10S,12S,13R)-3,12-Dihydroxy-10,13-dimethylhexadecahydro-1H-cyclopenta[a]phenanthren-17-yl)pentanoyl)glycyl)oxy)methoxy)-5-oxo-2-(phosphonomethyl)pentanoic acid (5, LTP791)

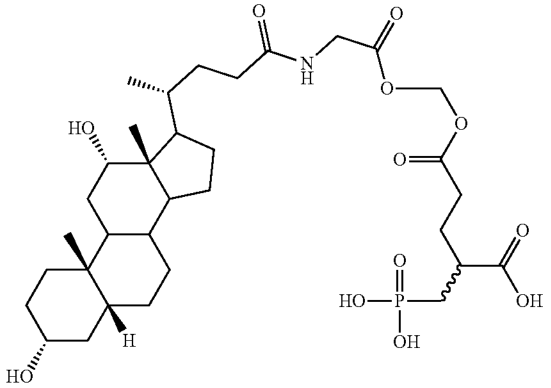 [SMILES: C[C@H](CCC(=O)NCC(=O)OCOC(=O)CCC(CP(=O)(O)O)C(=O)O)C1CCC2C3CC[C@@H]4C[C@H](O)CC[C@]4(C)C3C[C@H](O)[C@@]21C]

Compound LTP781 (128 mg, 0.134 mmol, 1 equiv.) was dissolved in anhydrous THF (4 mL), 10% Pd/C (43 mg, 0.040 mmol, 0.3 equiv.) was added and the mixture was saturated with $H_2$ and stirred under $H_2$ atmosphere (balloon) at room temperature overnight. The precipitate was filtered off and washed with further THF (2×10 mL). The organic solvent was evaporated and the product was dissolved in $MeCN/H_2O$ mixture (1:1, 50 mL) and lyophilized for 3 days. The desired product 5 was obtained as a colorless foam (73 mg) in 79% yield.

$^1$H NMR (400 MHz, $CD_3OD$): $\delta_H$ 0.71 (s, 3H), 0.93 (s, 3H), 1.03 (d, J=6.4 Hz, 3H), 1.22-1.69 (m, 2H), 1.22-1.69 (m, 15H), 1.69-2.24 (m, 11H), 2.26-2.38 (m, 1H), 2.38-2.56 (m, 2H), 2.75 (dq, J=13.4, 7.0 Hz, 1H), 3.53 (tt, J=11.0, 4.4 Hz, 1H), 3.92-4.01 (m, 3H), 5.77 (s, 2H).

$^{13}$C NMR (101 MHz, $CD_3OD$): $\delta_C$ 13.24, 17.67, 23.74, 24.86, 27.43, 28.38, 28.60, 28.81 (d, J=10.4 Hz), 29.85, 30.30 (d, J=141.9 Hz), 30.90, 31.00, 32.07, 33.01, 33.64, 34.75, 35.26, 36.41, 36.71, 37.14, 37.39, 40.62 (d, J=3.2 Hz), 41.78, 43.56, 47.52, 48.05, 72.49, 74.01, 80.56, 170.07, 172.83, 177.35, 177.75 (d, J=10.0 Hz).

$^{31}$P NMR (162 MHz, $CD_3OD$): $\delta_P$ 28.29.

MALDI MS: 710.4 ($[M+Na]^+$).

HR MALDI MS: calcd for $C_{33}H_{53}O_{12}NPa$: 686.3311; found: 686.3298.

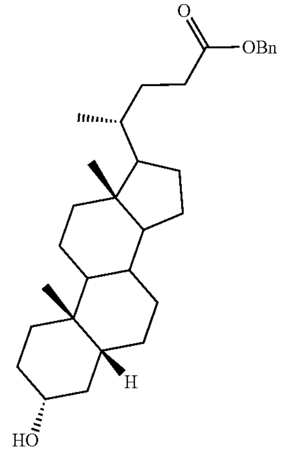 [SMILES: C[C@H](CCC(=O)OCc1ccccc1)C1CCC2C3CC[C@@H]4C[C@H](O)CC[C@]4(C)C3CC[C@@]21C]

Benzyl (4R)-44(3R,10S,13R)-3-hydroxy-10,13-dimethylhexadecahydro-1H-cyclopenta[a]phenanthren-17-yl)pentanoate (LTP761)
Scheme 3
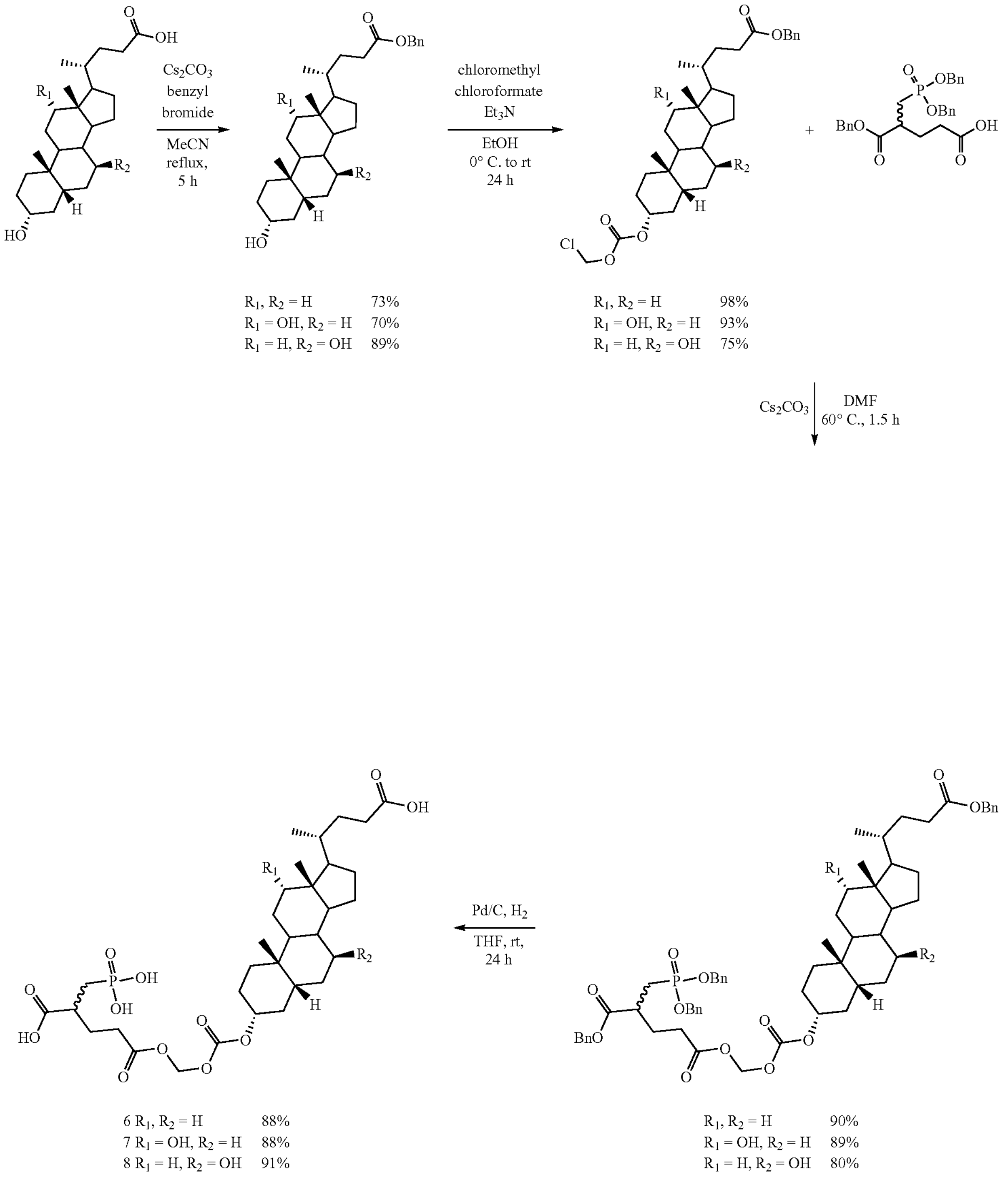

Compound was prepared according to the published procedure. $^1$H and $^{13}$C NMR spectra were in agreement with published data (*Org. Biomol. Chem.* 2014, 12, 9592).

Benzyl (4R)-4-((3R,10S,12S,13R)-3,12-dihydroxy-10,13-dimethylhexadecahydro-1H-cyclopenta[a]phenanthren-17-yl)pentanoate (LTP800)

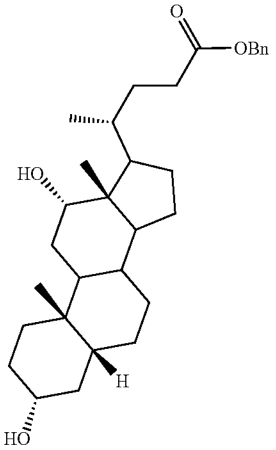 [SMILES: C[C@H](CCC(=O)OCc1ccccc1)C1CCC2C3CC[C@@H]4C[C@H](O)CC[C@]4(C)C3C[C@H](O)[C@@]21C]

Compound was prepared according to the published procedure. $^1$H and $^{13}$C NMR spectra were in agreement with published data (*Org. Biomol. Chem.* 2014, 12, 9592).

Benzyl (4R)-4-((3R,7S,10S,13R)-3,7-dihydroxy-10,13-dimethylhexadecahydro-1H-cyclopenta[a]phenanthren-17-yl)pentanoate (IS-101-001)

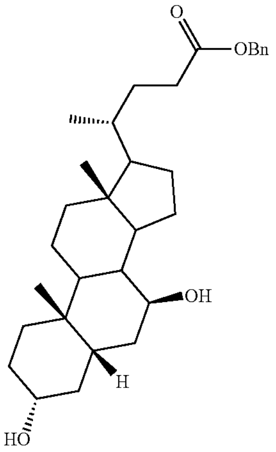 [SMILES: C[C@H](CCC(=O)OCc1ccccc1)C1CCC2C3C(CC[C@@]21C)[C@@]1(C)CC[C@@H](O)C[C@H]1C[C@@H]3O]

Compound was prepared according to the published procedure. $^1$H and $^{13}$C NMR spectra were in agreement with published data (*Org. Biomol. Chem.* 2014, 12, 9592).

Benzyl (4R)-4-((3R,10S,13R)-3-(((chloromethoxy)carbonyl)oxy)-10,13-dimethylhexadecahydro-1H-cyclopenta[a]phenanthren-17-yl)pentanoate (LTP772)

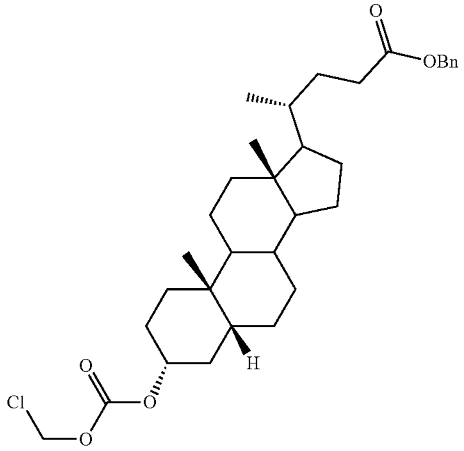 [SMILES: C[C@H](CCC(=O)OCc1ccccc1)C1CCC2C3CC[C@@H]4C[C@H](OC(=O)OCCl)CC[C@]4(C)C3CC[C@@]21C]

The starting material LTP761 (400 mg, 0.857 mmol, 1 equiv.) was suspended in anhydrous $Et_2O$ (10 mL) and the mixture was cooled to 0° C. and stirred under inert atmosphere. Triethylamine (130 mg, 179 μL, 1.29 mmol, 1.5 equiv.) followed by solution of chloromethyl chlorocarbonate (155 mg, 107 μL, 1.20 mmol, 1.4 in anhydrous $Et_2O$ (4 mL) were added dropwise. The resulting mixture was slowly heated to room temperature and stirred overnight (24 h) under inert. EtOAc (70 mL) was added and the organic phase was washed with distilled $H_2O$ (70 mL). The inorganic phase was then extracted with further EtOAc (70 mL) and combined organic phases were finally washed with sat. NaCl (50 mL), dried over $MgSO_4$ and solvent was evaporated. The crude product LTP772 was obtained in quantitative yield (479 mg) as a colorless solid and was used to the following step without further purification.

$^1$H NMR (400 MHz, $CDCl_3$): $\delta_H$ 0.62 (s, 3H), 0.90 (d, J=6.3 Hz, 3H), 0.93 (s, 3H), 0.97-1.30 (m, 9H), 1.31-1.49 (m, 8H), 1.50-1.70 (m, 2H), 1.74-2.01 (m, 7H), 2.27 (ddd, J=15.6, 9.2, 6.7 Hz, 1H), 2.40 (ddd, J=15.0, 9.9, 4.9 Hz, 1H), 4.59-4.74 (m, 1H), 5.11 (d, J=2.6 Hz, 2H), 5.72 (s, 2H), 7.29-7.46 (m, 5H). $^{13}$C NMR (101 MHz, $CDCl_3$): $\delta_C$ 12.15, 18.37, 20.94, 23.35, 24.29, 26.39, 26.49, 27.08, 28.28, 31.08, 31.39, 32.05, 34.65, 34.96, 35.43, 35.88, 40.21, 40.52, 41.98, 42.84, 56.06, 56.56, 66.21, 72.18, 80.15, 128.29, 128.35 (2C), 128.66 (2C), 136.25, 152.89, 174.21.

ESI MS: 581.4 ($[M+Na]^+$).

HR ESI MS: calcd for $C_{33}H_{47}O_5ClNa$: 581.30042; found: 581.30102.

Benzyl (4R)-4-((3R,10S,12S,13R)-3-(((chloromethoxy)carbonyl)oxy)-12-hydroxy-10,13-dimethylhexadecahydro-1H-cyclopenta[a]phenanthren-17-yl)pentanoate (LTP801)

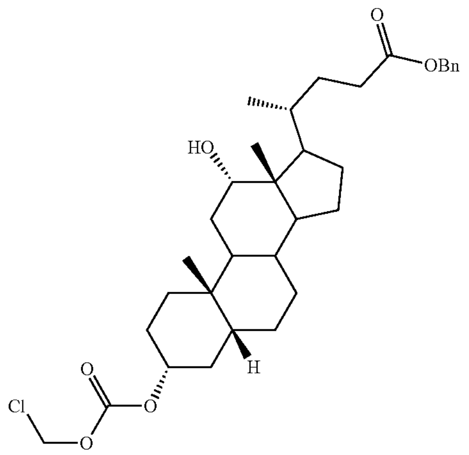 [SMILES: C[C@H](CCC(=O)OCc1ccccc1)C1CCC2C3CC[C@@H]4C[C@H](OC(=O)OCCl)CC[C@]4(C)C3C[C@H](O)[C@@]21C]

The starting material LTP800 (200 mg, 0.414 mmol, 1 equiv.) was suspended in anhydrous $Et_2O$ (6 mL) and the mixture was cooled to 0° C. and stirred under inert atmosphere. Triethylamine (50 mg, 69 μL, 0.497 mmol, 1.2 equiv.) followed by solution of chloromethyl chlorocarbonate (59 mg, 41 μL, 0.456 mmol, 1.1 equiv.) in anhydrous $Et_2O$ (3 mL) were added dropwise. The resulting mixture was slowly heated to room temperature and stirred overnight (24 h) under inert. EtOAc (50 mL) was added and the organic phase was washed with distilled $H_2O$ (50 mL). The inorganic phase was then extracted with further EtOAc (50 mL) and combined organic phases were finally washed with sat. NaCl (50 mL), dried over $MgSO_4$ and solvent was evaporated. The crude product was purified by LC (cyclohexane/EtOAc, 6:1) and desired product LTP801 was obtained as a colorless solid (220 mg) in 93% yield.

$^1$H NMR (400 MHz, $CDCl_3$): $\delta_H$ 0.65 (s, 3H), 0.93 (s, 3H), 0.96 (d, J=6.1 Hz, 3H), 1.00-1.17 (m, 2H), 1.18-1.32 (m, 2H), 1.32-1.71 (m, 14H), 1.74-1.90 (m, 5H), 1.90-2.01 (m, 1H), 2.29 (ddd, J=15.5, 8.9, 6.8 Hz, 1H), 2.42 (ddd, J=14.4, 9.6, 4.8 Hz, 1H), 3.94-3.99 (m, 1H), 4.66 (dq, J=11.3, 5.7, 4.5 Hz, 1H), 5.11 (d, J=3.1 Hz, 2H), 5.72 (s, 2H), 7.28-7.41 (m, 5H).

$^{13}$C NMR (101 MHz, $CDCl_3$): $\delta_C$ 12.84, 17.42, 23.12, 23.70, 26.09, 26.37, 27.00, 27.52, 28.75, 30.96, 31.41, 31.98, 33.70, 34.18, 34.80, 35.12, 36.06, 41.94, 46.60, 47.47, 48.28, 66.22, 72.17, 73.12, 80.01, 128.29, 128.35 (2C), 128.65 (2C), 136.21, 152.90, 174.12.

ESI MS: 597.4 ([M+Na]$^+$).

HR ESI MS: calcd for $C_{33}H_{47}O_6ClNa$: 597.29534; found: 597.29559.

Benzyl (4R)-4-((3R,7S,10S,13R)-3-(((chloromethoxy)carbonyl)oxy)-7-hydroxy-10,13-dimethylhexadecahydro-1H-cyclopenta[a]phenanthren-17-yl)pentanoate (IS-101-002)

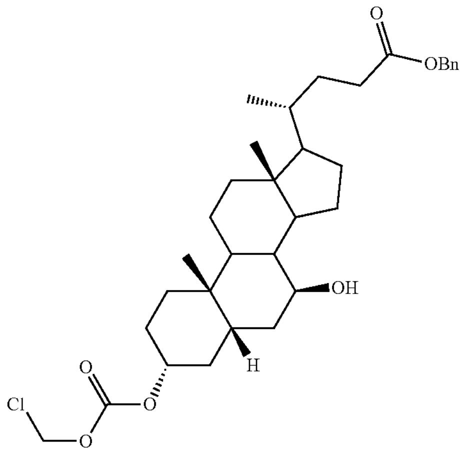 [SMILES: C[C@H](CCC(=O)OCc1ccccc1)C1CCC2C3C(CC[C@@]21C)[C@@]1(C)CC[C@@H](OC(=O)OCCl)C[C@H]1C[C@@H]3O]

Compound IS-101-001 (0.2 g, 0.41 mmol, 1 equiv.) was dissolved in diethylether (6 mL), reaction mixture was cooled down to 0° C. and $Et_3N$ (69 μL, 0.50 mmol, 1.2 equiv.) and chloromethyl chloroformate (41 μL, 0.45 mmol, 1.1 equiv.) were added. The reaction mixture was stirred for 16 h at rt. EtOAc (30 mL) was added and the mixture was washed with brine (20 mL) and dried over $Na_2SO_4$. Volatiles were evaporated under reduced pressure and the mixture was purified by column chromatography (cyclohexane/EtOAc, 4:1) to afford the desired product IS-101-002 (0.13 g, 54% yield) as a colorless solid.

$^1$H NMR (400 MHz, $CD_3OD$): $\delta_H$ 0.65 (s, 3H), 0.92 (d, J=6.2 Hz, 3H), 0.96 (s, 3H), 1.01-3.48 (m, 27H), 3.51-3.62 (m, 1H), 4.58-4.67 (m, 1H), 5.06-5.16 (m, 2H), 5.72 (s, 2H), 7.29-7.40 (m, 5H).

ESI MS: 597.3 ([M+Na]$^+$).

HR ESI MS: calcd for $C_{33}H_{47}O_6ClNa$: 597.29534; found: 597.29542.

1-Benzyl 5-((((((3R,10S,13R)-17-((R)-5-(benzyloxy)-5-oxopentan-2-yl)-10,13-dimethylhexadecahydro-1H-cyclopenta[a]phenanthren-3-yl)oxy)carbonyl)oxy)-methyl)-2-((bis(benzyloxy)phosphoryl)methyl)pentanedioate (LTP797)

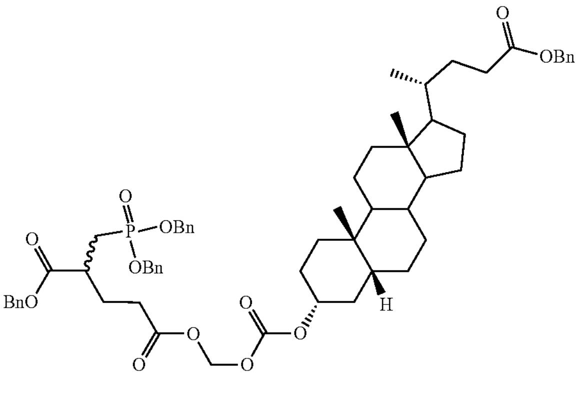

Compound LTP560 (133 mg, 0.268 mmol, 1.5 equiv.) was dissolved in anhydrous DMF (8 mL) and $Cs_2CO_3$ (64 mg, 0.197 mmol, 1.1 equiv.) was added. Finally compound LTP772 (100 mg, 0.179 mmol, 1 equiv.) was added and the reaction mixture was heated to 60° C. for 1 h under inert. DMF was evaporated, EtOAc (70 mL) was added and the organic phase was washed with sat. $NaHCO_3$ (30 mL), distilled $H_2O$ (30 mL) and sat. NaCl (30 mL) and dried over $MgSO_4$. Solvent was evaporated and the crude product was purified by LC (cyclohexane/EtOAc, 1:1) to afford the desired product LTP797 (164 mg, 90% yield) as a colorless oil.

$^1H$ NMR (400 MHz, $CDCl_3$): $\delta_H$ 0.61 (s, 3H), 0.90 (d, J=6.3 Hz, 3H), 0.92 (s, 3H), 0.95-1.16 (m, 6H), 1.18-1.68 (m, 13H), 1.73-1.99 (m, 10H), 2.20-2.46 (m, 5H), 2.82 (dddd, J=16.2, 13.4, 8.1, 5.8 Hz, 1H), 4.62 (ddt, J=16.0, 11.2, 5.8 Hz, 1H), 5.11 (d, J=2.5 Hz, 2H), 4.85-5.03 (m, 6H), 5.65-5.71 (m, 2H), 7.22-7.42 (m, 20H).

$^{13}C$ NMR (101 MHz, $CDCl_3$): $\delta_C$ 12.16, 18.39, 20.94, 23.38, 24.31, 26.41, 26.53, 27.10, 27.98 (d, J=12.9 Hz), 28.29, 28.31 (d, J=142.2 Hz), 29.85, 31.10, 31.43, 32.09, 34.66, 35.00, 35.45, 35.89, 39.19 (d, J=3.6 Hz), 40.23, 40.52, 41.99, 42.85, 56.07, 56.57, 66.23, 66.95, 67.54 (2C, d, J=6.4 Hz), 79.60, 81.82, 128.21-128.76 (20C), 135.63, 136.23 (d, J=1.9 Hz), 136.27, 136.29 (d, J=2.1 Hz), 153.48, 171.08, 173.60 (d, J=8.4 Hz), 174.24.

$^{31}P$ NMR (162 MHz, $CDCl_3$): $\delta_P$ 29.36.

ESI MS: 1014.5 ($[M+Na]^+$).

HR ESI MS: calcd for $C_{60}H_{75}O_{12}PNa$: 1041.48884; found: 1041.48927.

1-Benzyl 5-((((((3R,10S,12S,13R)-17-((R)-5-(benzyloxy)-5-oxopentan-2-yl)-12-hydroxy-10,13-dimethylhexadecahydro-1H-cyclopenta[a]phenanthren-3-yl)oxy)carbonyl)oxy) methyl)-2-((bis(benzyloxy) phosphoryl)methyl)pentanedioate (LTP806)

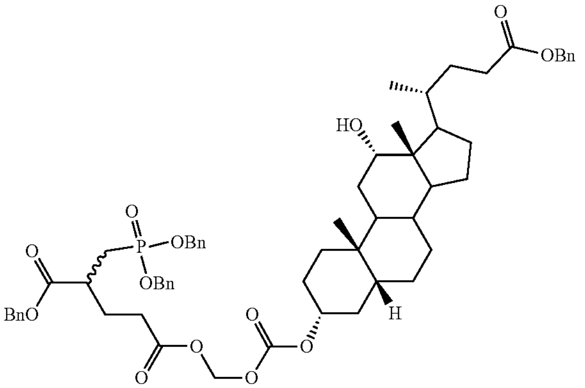 [SMILES: C[C@H](CCC(=O)OCc1ccccc1)C1CCC2C3CC[C@@H]4C[C@H](OC(=O)OCOC(=O)CCC(CP(=O)(OCc5ccccc5)OCc5ccccc5)C(=O)OCc5ccccc5)CC[C@]4(C)C3C[C@H](O)[C@@]21C]

Compound LTP560 (259 mg, 0.522 mmol, 1.5 equiv.) was dissolved in anhydrous DMF (16 mL) and $Cs_2CO_3$ (125 mg, 0.383 mmol, 1.1 equiv.) was added. Finally compound LTP801 (200 mg, 0.348 mmol, 1 equiv.) was added and the reaction mixture was heated to 60° C. for 1 h under inert. DMF was evaporated, EtOAc (70 mL) was added and the organic phase was washed with sat. $NaHCO_3$ (50 mL), distilled $H_2O$ (50 mL) and sat. NaCl (50 mL) and dried over $MgSO_4$. Solvent was evaporated and the crude product was purified by LC (cyclohexane/EtOAc, 2:1) to afford the desired product LTP806 (320 mg, 89% yield) as a colorless oil.

$^1H$ NMR (400 MHz, $CDCl_3$): $\delta_H$ 0.64 (s, 3H), 0.91 (s, 3H), 0.95 (d, J=5.9 Hz, 3H), 0.99-1.14 (m, 3H), 1.18-1.20 (m, 1H), 1.30-1.72 (m, 12H), 1.71-2.00 (m, 10H), 2.22-2.36 (m, 4H), 2.42 (ddd, J=14.4, 9.7, 4.6 Hz, 1H), 2.81 (tdd, J=13.3, 8.1, 5.8 Hz, 1H), 3.89-3.99 (m, 1H), 4.61 (tt, J=11.3, 4.4 Hz, 1H), 4.86-5.04 (m, 6H), 5.11 (d, J=3.1 Hz, 2H), 5.64-5.74 (m, 2H), 7.07-7.43 (m, 20H).

$^{13}C$ NMR (101 MHz, $CDCl_3$): $\delta_C$ 12.85, 17.42, 23.13, 23.72, 26.11, 26.37, 27.02, 27.53, 28.02 (d, J=13.0 Hz), 28.28 (d, J=142.4 Hz), 28.77, 30.99, 31.09, 31.43, 32.00, 33.68, 34.19, 34.84, 35.14, 36.07, 39.17 (d, J=3.6 Hz), 41.94, 46.61, 47.46, 48.28, 66.23, 66.94, 67.54 (2C, d, J=6.4 Hz), 73.09, 79.48, 81.82, 128.20-128.75 (20C), 135.62, 136.21 (d, J=1.9 Hz), 136.24, 136.27 (d, J=1.2 Hz), 153.46, 171.05, 173.58 (d, J=8.3 Hz), 174.13.

$^{31}P$ NMR (162 MHz, $CDCl_3$): $\delta_P$ 32.05.

ESI MS: 1057.5 ($[M+Na]^+$).

HR ESI MS: calcd for $C_{60}H_{75}O_{13}PNa$: 1057.48375; found: 1057.48410.

1-Benzyl 5-(2-(((3R,7S,10S,13R,17R)-17-((R)-5-(benzyloxy)-5-oxopentan-2-yl)-7-hydroxy-10,13-dimethylhexadecahydro-1H-cyclopenta[a]phenanthren-3-yl)oxy)-2-oxoethyl) 2-((bis(benzyloxy)phosphoryl)methyl)pentanedioate (IS-101-009)

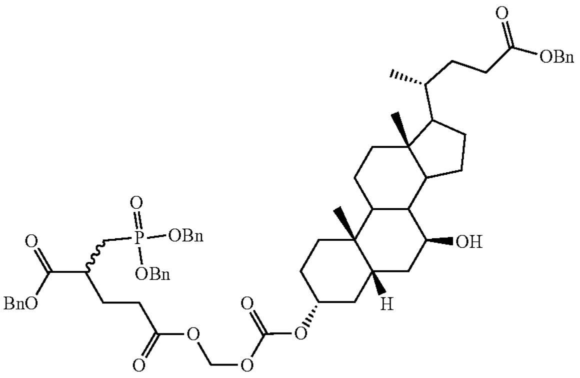 [SMILES: C[C@H](CCC(=O)OCc1ccccc1)C1CCC2C3C(CC[C@@]21C)[C@@]1(C)CC[C@@H](OC(=O)OCOC(=O)CCC(CP(=O)(OCc2ccccc2)OCc2ccccc2)C(=O)OCc2ccccc2)C[C@H]1C[C@@H]3O]

Compound IS-101-002 (0.11 g, 0.19 mmol, 1 equiv.), LTP592 (0.11 g, 0.23 mmol, 1.2 equiv.) and $Cs_2CO_3$ (68 mg, 0.21 mmol, 1.1 equiv.) were suspended in anhydrous DMF (10 mL). The resulting mixture was stirred under inert atmosphere for 1.5 hours at 60° C. DMF was evaporated, the residue was dissolved in EtOAc (50 mL), washed with brine (10 mL) and dried over $Na_2SO_4$. Volatiles were evaporated and the mixture was purified by column chromatography (DCM/MeOH, 40:1) to afford the desired compound IS-101-009 as a colorless solid (0.18 g, 84% yield).

$^1H$ NMR (400 MHz, $CDCl_3$): $\delta_H$ 0.65 (s, 3H), 0.92 (d, J=6.2 Hz, 3H), 0.95 (s, 3H), 1.00-2.02 (m, 27H), 2.20-2.46 (m, 5H), 2.75-2.87 (m, 1H), 3.54 (t, J=5.9 Hz, 1H), 4.57 (dt, J=11.2, 6.0 Hz, 1H), 4.86-5.03 (m, 6H), 5.11 (d, J=3.1 Hz, 2H), 5.68 (d, J=1.5 Hz, 2H), 7.22-7.40 (m, 20H).

$^{31}P$ NMR (162 MHz, $CDCl_3$): $\delta_P$ 32.01.

ESI MS: 1057.6 ($[M+Na]^+$).

HR ESI MS: calcd for $C_{60}H_{76}O_{13}P$: 1035.50181; found: 1035.50160.

5-((((((3R,10S,13R)-17-((R)-4-Carboxybutan-2-yl)-10,13-dimethylhexadecahydro-1H-cyclopenta[a]phenanthren-3-yl)oxy)carbonyl)oxy)methoxy)-5-oxo-2-(phosphonomethyl) pentanoic acid (6, LTP798)

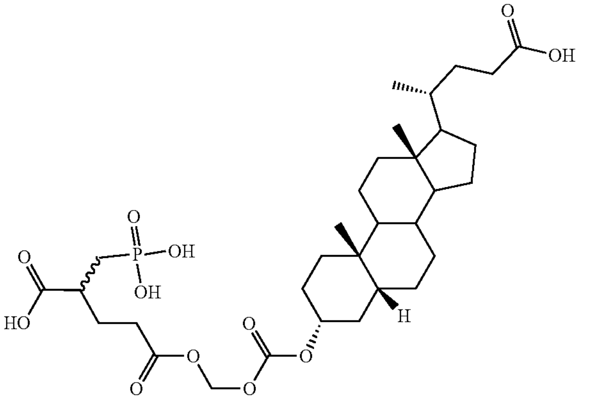 [SMILES: C[C@H](CCC(=O)O)C1CCC2C3CC[C@@H]4C[C@H](OC(=O)OCOC(=O)CCC(CP(=O)(O)O)C(=O)O)CC[C@]4(C)C3CC[C@@]21C]

Compound LTP797 (156 mg, 0.153 mmol, 1 equiv.) was dissolved in anhydrous THF (7 mL), 10% Pd/C (65 mg, 0.061 mmol, 0.4 equiv.) was added and the mixture was saturated with $H_2$ and stirred under $H_2$ atmosphere (balloon) at room temperature overnight. The precipitate was filtered off and washed with further THF (2×15 mL). The organic solvent was evaporated and the product was dissolved in $MeCN/H_2O$ mixture (1:1, 50 mL) and lyophilized for 2 days. The desired product 6 was obtained as a colorless foam (89 mg) in 88% yield.

$^1$H NMR (400 MHz, $CD_3OD$): $\delta_H$ 0.70 (s, 3H), 0.95 (d, J=6.6 Hz, 3H), 0.97 (s, 3H), 1.00-1.21 (m, 5H), 1.21-1.54 (m, 13H), 1.57-1.68 (m, 2H), 1.72-2.12 (m, 8H), 2.12-2.27 (m, 2H), 2.27-2.38 (m, 1H), 2.39-2.56 (m, 2H), 2.68-2.84 (m, 1H), 4.59 (tt, J=10.8, 4.6 Hz, 1H), 5.72 (s, 2H).

$^{13}$C NMR (101 MHz, $CD_3OD$): $\delta_C$ 12.59, 18.85, 21.95, 23.82, 25.26, 27.52, 28.12, 28.81 (d, J=10.6 Hz), 29.20, 30.08 (d, J=140.1 Hz), 31.93, 32.06, 32.26, 33.19, 35.34, 35.62, 35.91, 36.63, 37.13, 40.54 (d, J=3.3 Hz), 41.42, 41.78, 43.20, 43.88, 57.37, 57.77, 80.31, 83.04, 154.77, 172.77, 177.60 (d, J=10.0 Hz), 178.03.

$^{31}$P NMR (162 MHz, $CD_3OD$): $\delta_P$ 28.88.

MALDI MS: 657.3 ([M−H]$^+$).

HR MALDI MS: calcd for $C_{32}H_{50}O_{12}P$: 657.3045; found: 657.3028.

5-((((((3R,10S,12S,13R)-17-((R)-4-Carboxybutan-2-yl)-12-hydroxy-10,13-dimethylhexadecahydro-1H-cyclopenta[a]phenanthren-3-yl)oxy)carbonyl)oxy)methoxy)-5-oxo-2-(phosphonomethyl)pentanoic acid (7, LTP808)

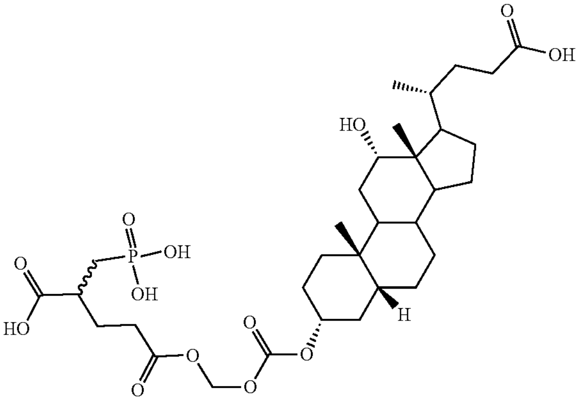 [SMILES: C[C@H](CCC(=O)O)C1CCC2C3CC[C@@H]4C[C@H](OC(=O)OCOC(=O)CCC(CP(=O)(O)O)C(=O)O)CC[C@]4(C)C3C[C@H](O)[C@@]21C]

Compound LTP806 (296 mg, 0.286 mmol, 1 equiv.) was dissolved in anhydrous THF (12 mL), 10% Pd/C (122 mg, 0.114 mmol, 0.4 equiv.) was added and the mixture was saturated with $H_2$ and stirred under $H_2$ atmosphere (balloon) at room temperature overnight. The precipitate was filtered off and washed with further THF (2×20 mL). The organic solvent was evaporated and the product was dissolved in $MeCN/H_2O$ mixture (1:1, 50 mL) and lyophilized for 2 days. The desired product 7 was obtained as a colorless foam (170 mg) in 88% yield.

$^1$H NMR (400 MHz, $CD_3OD$): $\delta_H$ 0.72 (s, 3H), 0.96 (s, 3H), 1.01 (d, J=6.4 Hz, 3H), 1.04-1.24 (m, 2H), 1.26-1.39 (m, 3H), 1.41-1.68 (m, 10H), 1.73-2.10 (m, 11H), 2.10-2.27 (m, 2H), 2.35 (ddt, J=15.0, 9.7, 5.0 Hz, 1H), 2.42-2.55 (m, 2H), 2.70-2.83 (m, 1H), 3.92-4.00 (m, 1H), 4.59 (td, J=11.1, 5.5 Hz, 1H), 5.72 (s, 2H).

$^{13}$C NMR (101 MHz, $CD_3OD$): $\delta_C$ 13.33, 17.66, 23.58, 24.78, 27.15 (d, J=4.3 Hz), 28.02, 28.54, 28.65, 28.76, 29.60, 30.09 (d, J=138.3 Hz), 31.04, 32.02, 32.05, 32.95, 34.51, 35.07, 35.27, 35.65, 36.48, 37.14, 40.50 (d, J=3.1 Hz), 42.99, 47.39, 47.84, 73.72, 80.69, 83.14, 154.69, 173.29, 178.09 (d, J=9.2 Hz), 178.50.

$^{31}$P NMR (162 MHz, $CD_3OD$): $\delta_P$ 28.27.

MALDI MS: 673.3 ([M−H]$^+$).

HR MALDI MS: calcd for $C_{32}H_{50}O_{13}P$: 673.2995; found: 673.3013.

5-(2-(((3R,7S,10S,13R,17R)-17-((R)-4-Carboxybutan-2-yl)-7-hydroxy-10,13-dimethylhexadecahydro-1H-cyclopenta[a]phenanthren-3-yl)oxy)-2-oxoethoxy)-5-oxo-2-(phosphonomethyl)pentanoic acid (8, IS-101-010)

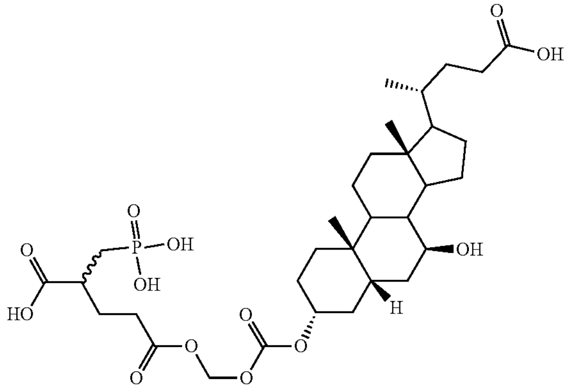 [SMILES: C[C@H](CCC(=O)O)C1CCC2C3C(CC[C@@]21C)[C@@]1(C)CC[C@@H](OC(=O)OCOC(=O)CCC(CP(=O)(O)O)C(=O)O)C[C@H]1C[C@@H]3O]

Compound IS-101-009 (3.70 g, 3.57 mmol) was dissolved in anhydrous THF (50 mL) and 10% palladium on carbon (1.52 g, 1.43 mmol, 0.4 equiv.) was added. Reaction flask was evacuated and filled with hydrogen and stirred at rt for 16 h. Palladium on carbon was removed by filtration through Celite™ and volatiles were evaporated under reduced pressure to afford the desired product 8 (2.2 g, 91% yield) as a colorless solid.

$^1$H NMR (400 MHz, $CD_3OD$): $\delta_H$ 0.72 (s, 3H), 0.92-1.02 (m, 6H), 1.04-1.62 (m, 16H), 1.67-2.55 (m, 16H), 2.75 (d, J=7.0 Hz, 1H), 3.47 (d, J=2.2 Hz, 1H), 4.50-4.62 (m, 1H), 5.72 (s, 2H).

$^{31}$P NMR (162 MHz, $CD_3OD$): $\delta_P$ 28.85.

ESI MS: 673.3 ([M−H]$^+$).

HR ESI MS: calcd for $C_{32}H_{50}O_{13}P$: 673.29945; found: 673.29917.

Scheme 4

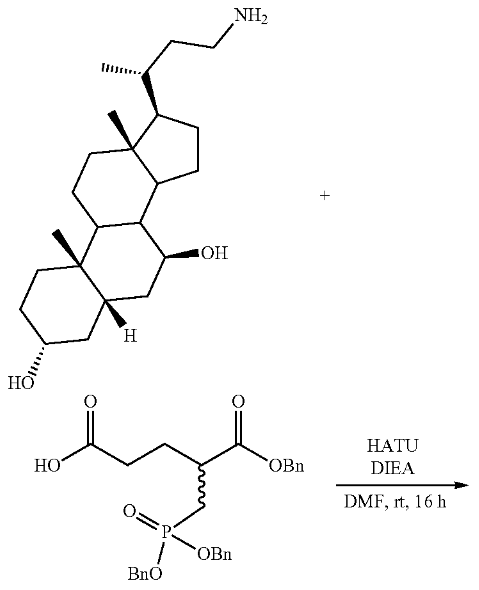

-continued

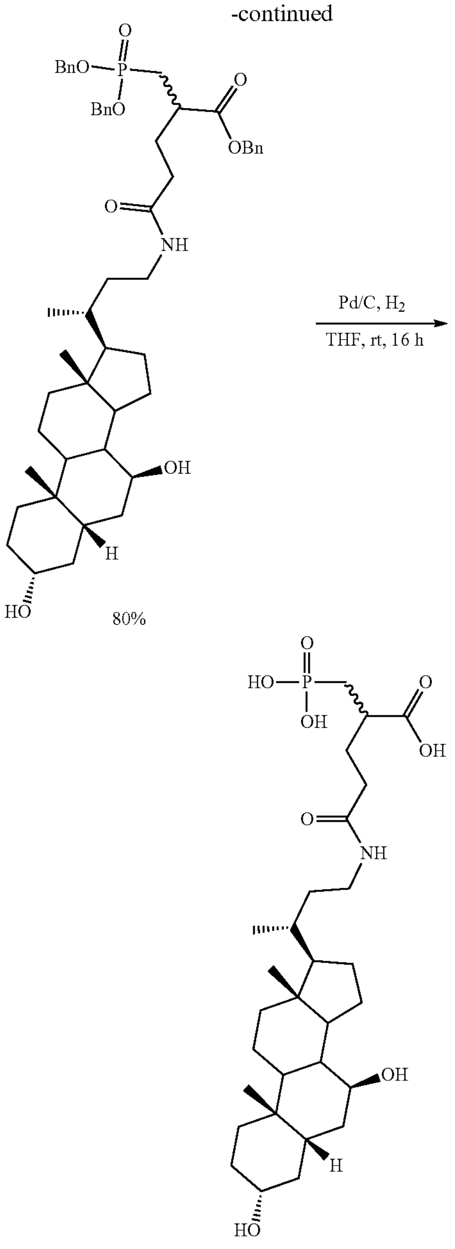

9 IS-101-020 91%

(3R,7S,10S,13R,17R)-17-((R)-4-Aminobutan-2-yl)-10,13-dimethylhexadecahydro-1H-cyclopenta[a]phenanthrene-3,7-diol (TT220219)

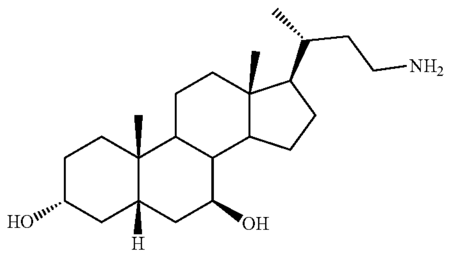 [SMILES: C[C@H](CCN)[C@H]1CCC2C3C(CC[C@@]21C)[C@@]1(C)CC[C@@H](O)C[C@H]1C[C@@H]3O]

Compound was prepared according to the published procedure (*J. Med. Chem.* 2004, 47, 4559-4569.

$^1H$ NMR (400 MHz, $CD_3OD$): $\delta_H$ 0.73 (s, 3H), 0.98 (d, J=6.4 Hz, 6H), 1.02-1.70 (m, 19H), 1.77-1.95 (m, 4H), 2.05 (dt, J=12.5, 3.2 Hz, 1H), 2.57-2.81 (m, 2H), 3.43-3.55 (m, 2H).

$^{13}C$ NMR (101 MHz, $CD_3OD$): $\delta_C$ 12.6, 19.4, 22.4, 24.0, 27.9, 29.8, 31.0, 35.2, 35.2, 36.1, 38.0, 38.6, 39.4, 39.7, 40.7, 41.6, 44.0, 44.5, 44.8, 56.8, 57.5, 71.9, 72.1.

ESI MS: 364.3 ([M+H]$^+$).

HR ESI MS: calcd for $C_{23}H_{42}O_2N$: 364.32101; found: 364.32088.

Benzyl 2-((bis(benzyloxy)phosphoryl)methyl-5-(((3R)-3-((3R,7S,10S,13R,17R)-3,7-dihydroxy-10,13-dimethylhexadecahydro-1H-cyclopenta[a]phenanthren-17-yl)butyl)amino)-5-oxopentanoate (IS-101-019)

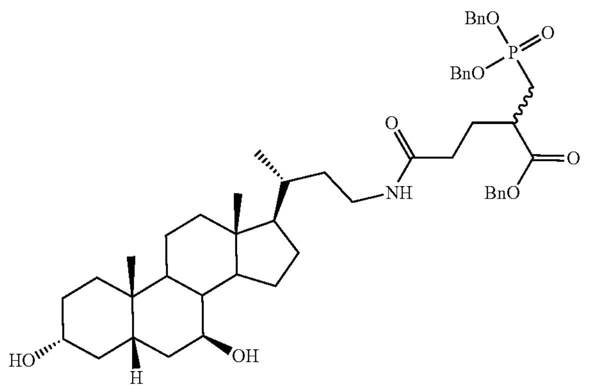 [SMILES: C[C@H](CCNC(=O)CCC(CP(=O)(OCc1ccccc1)OCc1ccccc1)C(=O)OCc1ccccc1)[C@H]1CCC2C3C(CC[C@@]21C)[C@@]1(C)CC[C@@H](O)C[C@H]1C[C@@H]3O]

Compound LTP560 (1.50 g, 3.02 mmol, 1 equiv.) was dissolved in DMF (50 mL) and HATU (1.15 g, 3.02 mmol, 1 equiv.) followed by DIEA (1.58 mL, 9.07 mmol, 3 equiv.) were added. Reaction mixture was stirred for 5 minutes and compound TT220219 (1.10 g, 3.02 mmol, 1 equiv.) dissolved in DMF (5 ML) was added. Reaction mixture was stirred at room temperature for 16 h. Volatiles were evaporated and EtOAc (100 mL) was added and organic layer was washed with 10% aq. $KHSO_4$ (30 mL), sat. $NaHCO_3$ (30 mL) and brine (30 mL). Organic portion was dried over $Na_2SO_4$ and volatiles were evaporated under reduced pressure. The mixture was purified by column chromatography (DCM/MeOH, 20:1) to afford the desired product IS-101-019 (2.02 g, 80% yield) as a colorless solid.

$^1H$ NMR (400 MHz, $CDCl_3$): $\delta_H$ 0.66 (s, 3H), 0.94 (d, J=5.2 Hz, 6H), 0.98-2.11 (m, 29H), 2.32 (td, J=16.8, 8.5 Hz, 1H), 2.73-2.86 (m, 1H), 3.02-3.13 (m, 1H), 3.15-3.29 (m, 1H), 3.52-3.78 (m, 2H), 4.79-5.09 (m, 6H), 5.41 (d, J=5.9 Hz, 1H), 7.20-7.40 (m, 15H).

$^{31}P$ NMR (162 MHz, $CDCl_3$): $\delta_P$ 32.39.

ESI MS: 864.5 ([M+Na]$^+$).

HR ESI MS: calcd for $C_{50}H_{68}O_8NNaP$: 864.45748; found: 864.45679.

5-(((3R)-3-((3R,7S,10S,13R,17R)-3,7-Dihydroxy-10,13-dimethylhexadecahydro-1H-cyclopenta[a]phenanthren-17-yl)butyl)amino)-5-oxo-2-(phosphonomethyl)pentanoic acid (9, IS-101-020)

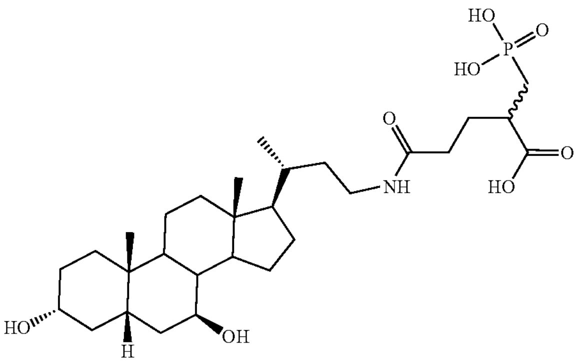 [SMILES: C[C@H](CCNC(=O)CCC(CP(=O)(O)O)C(=O)O)[C@H]1CCC2C3C(CC[C@@]21C)[C@@]1(C)CC[C@@H](O)C[C@H]1C[C@@H]3O]

Compound IS-101-019 (2.02 g, 2.39 mmol) was dissolved in anhydrous THF (60 mL) and 10% palladium on carbon (200 mg) was added. Reaction flask was evacuated and filled with hydrogen and stirred at rt for 16 h. Palladium on carbon was removed by filtration through Celite™ and volatiles were evaporated under reduced pressure to afford the desired product 9 (1.25 g, 91% yield) as a colorless solid.

$^1H$ NMR (400 MHz, $CD_3OD$): $\delta_H$ 0.72 (s, 3H), 0.91-1.01 (m, 6H), 1.02-1.73 (m, 22H), 1.74-2.33 (m, 9H), 2.66-2.79 (m, 1H), 3.06-3.18 (m, 1H), 3.18-3.29 (m, 1H), 3.41-3.55 (m, 2H).

$^{31}P$ NMR (162 MHz, $CD_3OD$): $\delta_P$ 28.82.

ESI MS: 570.3 ([M−H]$^+$).

HR ESI MS: calcd for $C_{29}H_{49}O_8NP$: 570.32013; found: 570.31981.

Scheme 5

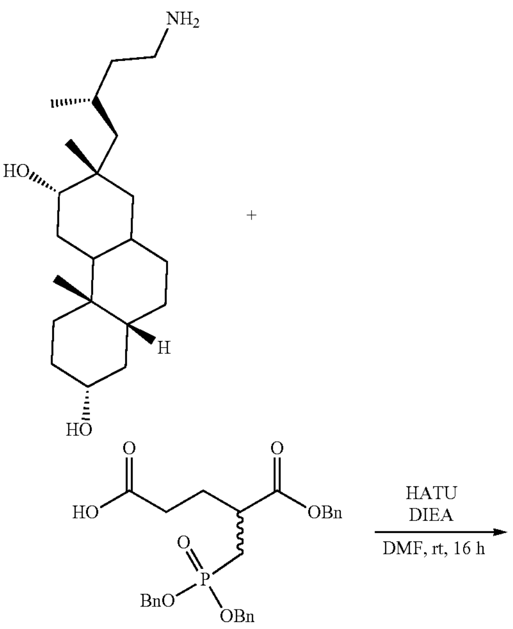

-continued

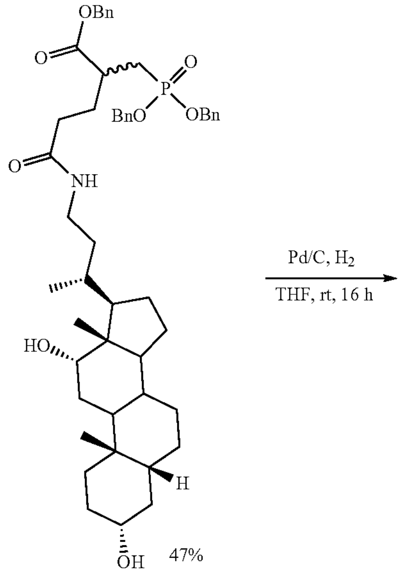

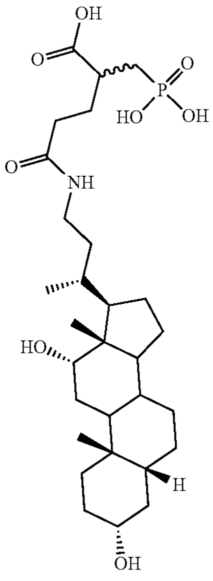

10 IS-101-077 96%

Benzyl 2-((bis(benzyloxy)phosphoryl)methyl)-5-(((3R)-3-((3R,10S,12S,13R,17R)-3,12-dihydroxy-10,13-dimethylhexadecahydro-1H-cyclopenta[a]phenanthren-17-yl)butyl)amino)-5-oxopentanoate (IS-101-076)

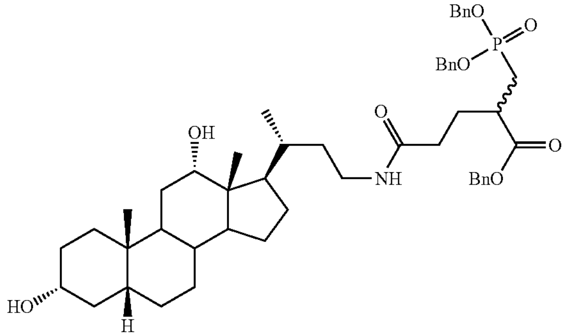 [SMILES: C[C@H](CCNC(=O)CCC(CP(=O)(OCc1ccccc1)OCc1ccccc1)C(=O)OCc1ccccc1)[C@H]1CCC2C3CC[C@@H]4C[C@H](O)CC[C@]4(C)C3C[C@H](O)[C@@]21C]

Compound LTP560 (1.70 g, 3.44 mmol, 1 equiv.) was dissolved in DMF (50 mL) and HATU (1.30 g, 3.44 mmol, 1 equiv.) followed by DIEA (1.79 mL, 10.3 mmol, 3 equiv.) were added. Reaction mixture was stirred for 5 minutes and compound IS-100-076 (1.25 g, 3.44 mmol, 1 equiv.) dissolved in DMF (5 mL) was added. Reaction mixture was stirred at room temperature for 16 h. Volatiles were evaporated and EtOAc (100 mL) was added and organic layer was washed with 10% aq. $KHSO_4$ (30 mL), sat. $NaHCO_3$ (30 mL) and brine (30 mL). Organic portion was dried over $Na_2SO_4$ and volatiles were evaporated under reduced pressure. The mixture was purified by column chromatography (DCM/MeOH, 20:1) to afford the desired product IS-101-076 (2.05 g, 70% yield) as a colorless solid.

$^1H$ NMR (400 MHz, $CDCl_3$): $\delta_H$ 0.66 (s, 3H), 0.90 (s, 3H), 0.93-2.13 (m, 32H), 2.24-2.39 (m, 1H), 2.74-2.85 (m, 1H), 3.04-3.29 (m, 2H), 3.53-3.65 (m, 1H), 3.95 (s, 1H), 4.85-5.07 (m, 6H), 5.65 (bs, 1H), 7.23-7.38 (s, 15H).

$^{31}P$ NMR (162 MHz, $CDCl_3$): $\delta_P$ 32.14, 32.17.

ESI MS: 864.6 ($[M+Na]^+$).

HR ESI MS: calcd for $C_{50}H_{69}O_8NP$: 842.47553; found: 842.47532.

5-(((3R)-3-((3R,10S,12S,13R,17R)-3,12-Dihydroxy-10,13-dimethylhexadecahydro-1H-cyclopenta[a]phenanthren-17-yl)butyl)amino)-5-oxo-2-(phosphonomethyl)pentanoic acid (10, IS-101-077)

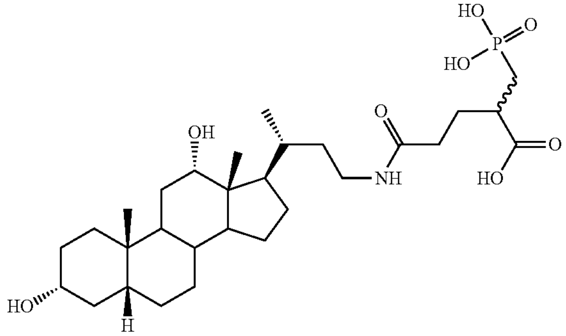 [SMILES: C[C@H](CCNC(=O)CCC(CP(=O)(O)O)C(=O)O)[C@H]1CCC2C3CC[C@@H]4C[C@H](O)CC[C@]4(C)C3C[C@H](O)[C@@]21C]

Compound IS-101-076 (2.00 g, 2.37 mmol, 1 equiv.) was dissolved in anhydrous THF (50 mL) and 10% palladium on carbon (100 mg) was added. Reaction flask was evacuated and filled with hydrogen and stirred at rt for 16 h. Palladium on carbon was removed by filtration through Celite™ and volatiles were evaporated under reduced pressure to afford the desired product 10 (1.31 g, 96% yield) as a colorless solid.

$^{1}$H NMR (400 MHz, $d_6$-DMSO): $\delta_H$ 0.59 (s, 3H), 0.84 (s, 3H), 0.93 (d, J=6.5 Hz, 3H), 0.96-2.12 (m, 31H), 2.93 (d, J=7.6 Hz, 1H), 3.02-3.19 (m, 1H), 3.30-3.42 (m, 1H), 3.79 (d, J=2.7 Hz, 1H), 7.72 (s, 1H).

$^{31}$P NMR (162 MHz, $d_6$-DMSO): $\delta_P$ 26.61.

ESI MS: 570.3 ($[M-H]^+$).

HR ESI MS: calcd for $C_{29}H_{49}O_8NP$: 570.32013; found: 570.31989.

Scheme 6

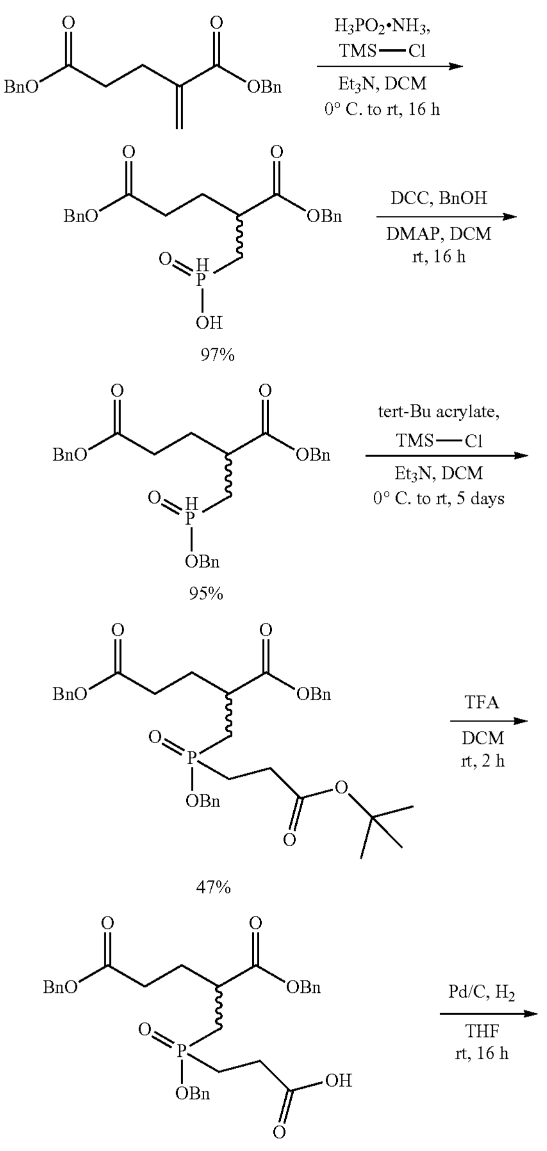

-continued

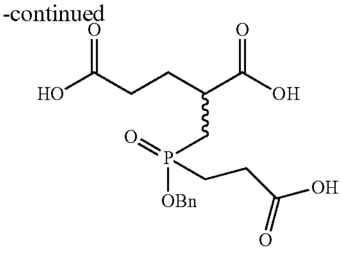

11 IS-100-026 90%

(5-(Benzyloxy)-2-((benzyloxy)carbonyl)-5-oxopentyl)phosphinic acid (IS-100-018)

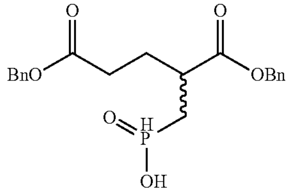

Compound was prepared according to the published procedure. $^{1}$H and $^{13}$C NMR spectra were in agreement with previously published data (*Tet. Asym.* 2002, 13, 1609-1614).

Di-benzyl 2-[(benzyloxyphosphinyl)methy]pentanedioate (IS-100-020)

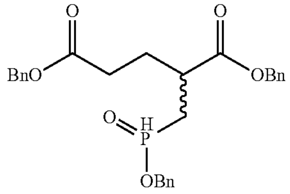

Compound IS-100-018 (3.15 g, 8.07 mmol, 1 equiv.) was dissolved in anhydrous THF (50 mL) and benzylalcohol (1.1 mL, 10.5 mmol, 1.3 equiv.) followed by addition of DCC (1.75 g, 8.47 mmol, 1.05 equiv.) and DMAP (0.09 g, 0.8 mmol, 0.1 equiv.). The reaction mixture was stirred at room temperature for 16 h. After completion, DCU was filtered off and volatiles were evaporated under reduced pressure. Residue was dissolved in EtOAc (60 mL) and organic layer was extracted with 1M aq. HCl (30 mL) and brine (30 mL). Organic portion was dried over $Na_2SO_4$ and volatiles were evaporated under reduced pressure. The crude product was purified by column chromatography (DCM/MeOH, 50:1) to afford the desired product IS-100-020 (3.68 g, 95% yield) as a colourless oil. $^{1}$H and $^{13}$C NMR spectra were in agreement with previously published data (*J. Med. Chem.* 2001, 44, 4170-4175).

Dibenzyl 2-(((benzyloxy)(3-(tert-butoxy)-3-oxopropyl)phosphoryl)methyl)pentanedioate (IS-100-021)

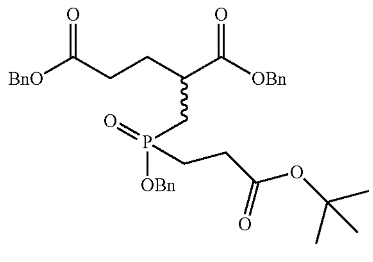 [SMILES: CC(C)(C)OC(=O)CCP(=O)(CC(CCC(=O)OCc1ccccc1)C(=O)OCc1ccccc1)OCc1ccccc1]

Compound IS-100-020 (4.00 g, 8.32 mmol, 1 equiv.) was dissolved in anhydrous DCM (70 mL), $Et_3N$ (5.22 ML, 37.5 mmol, 4.5 equiv.) was added and the reaction mixture was cooled down to 0° C. Trimethylsilyl chloride (4.22 mL, 33.3 mmol, 4 equiv.) was added slowly and after 1 hour tert-butyl acrylate (3.62 mL, 24.9 mmol, 3 equiv.) was added. The reaction mixture was slowly warmed up to room temperature and stirred for 5 days. Further DCM (100 mL) was added and organic layer was extracted with 1M aq. HCl (50 mL) and brine (50 mL). Organic portion was dried over $Na_2SO_4$ and volatiles were evaporated under reduced pressure. The crude product was purified by column chromatography (DCM/MeOH, 40:1) to afford the desired product IS-100-021 (2.38 g, 47% yield) as a colourless oil.

$^1H$ NMR (400 MHz, $CDCl_3$): $\delta_H$ 1.42 (s, 9H), 1.75-1.86 (m, 1H), 1.90-2.05 (m, 4H), 2.20-2.54 (m, 5H), 2.81-2.93 (m, 1H), 4.70 (s, 1H), 4.91-5.09 (m, 5H), 7.27-7.40 (m, 15H), $^{31}P$ NMR (162 MHz, $CDCl_3$): $\delta_P$ 57.42, 57.02.

ESI MS: 631.3 ($[M+Na]^+$).

HR ESI MS: calcd for $C_{34}H_{41}O_8PNa$: 631.24313; found: 631.24337.

3-((Benzyloxy)(5-(benzyloxy)-2-((benzyloxy)carbonyl)-5-oxopentyl)phosphoryl) propanoic acid (IS-100-025)

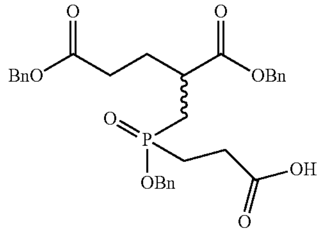 [SMILES: O=C(O)CCP(=O)(CC(CCC(=O)OCc1ccccc1)C(=O)OCc1ccccc1)OCc1ccccc1]

Compound IS-100-021 (0.50 g, 0.82 mmol, 1 equiv.) was dissolved in DCM (1 mL) and trifluoroacetic acid (5 mL, 65.3 mmol) and the reaction mixture was stirred at rt for 2 hours. Volatiles were evaporated under reduced pressure and the residue was redissolved in DCM (20 mL) and evaporated to remove residual TFA three times. Crude compound IS-100-025 (0.44 g, 97% yield) was used in the next step without further purification.

$^1H$ NMR (400 MHz, $CDCl_3$): $\delta_H$ 1.80-2.13 (m, 5H), 2.22-2.40 (m, 3H), 2.42-2.66 (m, 2H), 2.79-2.92 (m, 1H), 4.91-5.10 (m, 6H), 7.23-7.37 (m, 15H).

$^{31}P$ NMR (162 MHz, $CDCl_3$): $\delta_P$ 59.69, 59.46.

ESI MS: 551.2 ($[M-H]^+$).

HR ESI MS: calcd for $C_{30}H_{32}O_8P$: 551.18403; found: 551.18332.

2-(((2-Carboxyethyl)(hydroxy)phosphoryl)methyl) pentanedioic acid (11, IS-100-026)

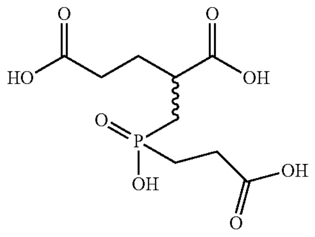 [SMILES: O=C(O)CCC(CP(=O)(O)CCC(=O)O)C(=O)O]

Compound IS-100-025 (0.44 g, 0.79 mmol, 1 equiv.) was dissolved in anhydrous THF (20 mL) and 10% palladium on carbon (60 mg) was added. Reaction flask was evacuated and OH filled with hydrogen (1 atm) and stirred at rt for 16 h. Palladium on carbon was removed by filtration through Celite™ and volatiles were evaporated under reduced pressure to afford the desired product 11 (0.21 g, 90% yield) as a colourless oil. $^1H$ and $^{13}C$ NMR spectra were in agreement with previously published data (*J. Med. Chem.* 1996, 39, 619-622).

Scheme 7

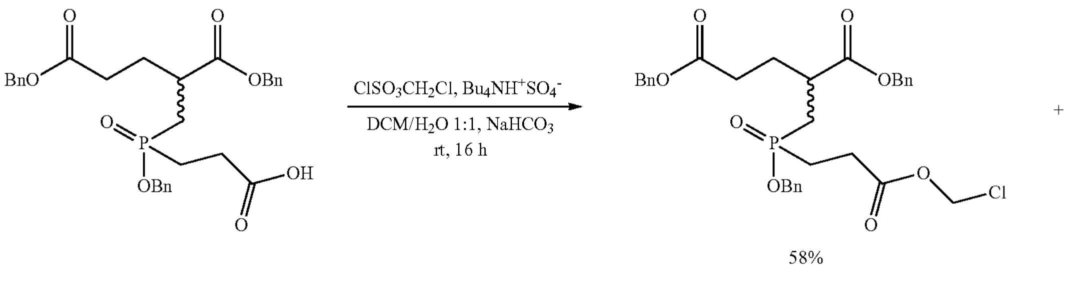

-continued

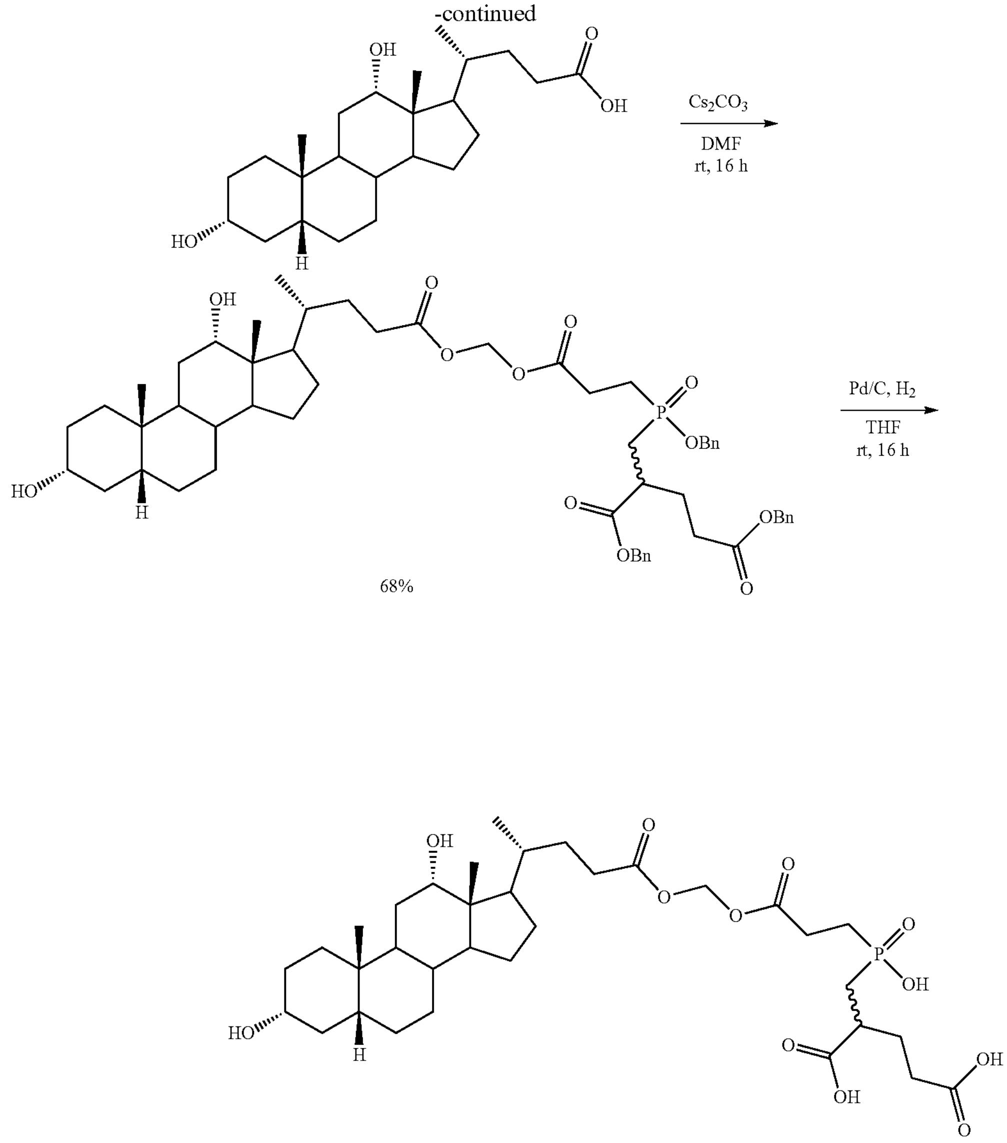

12 IS-100-058 77%

Dibenzyl 2-(((benzyloxy)3-(chloromethoxy)-3-oxopropyl)phosphoryl)methyl)pentanedioate (IS-100-055)

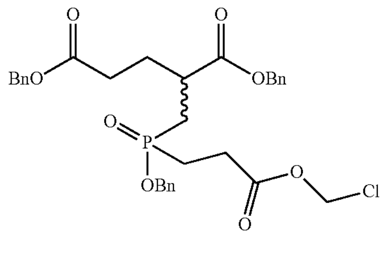 [SMILES: O=C(CCP(=O)(CC(CCC(=O)OCc1ccccc1)C(=O)OCc1ccccc1)OCc1ccccc1)OCCl]

Compound IS-100-025 (0.68 g, 1.23 mmol, 1 equiv.) was dissolved in DCM (10 mL), distilled water (10 mL), $NaHCO_3$ (0.52 g, 6.2 mmol, 5 equiv.) and $Bu_4N^+HSO_4^-$ (42 mg, 0.12 mmol, 0.1 equiv.) were added. The reaction mixture was vigorously stirred for 5 minutes at rt and chloromethyl chlorosulphate (0.15 mL, 1.47 mmol, 1.2 equiv.) in DCM (5 mL) was added during 1 minute. The resulting mixture was stirred for 20 h at rt. Further DCM (20 mL) was added and phases were separated. Aqueous phase was extracted with DCM (50 mL) and combined organic fractions were washed with sat. NaCl (50 mL), dried over $Na_2SO_4$ and all volatiles were evaporated under reduced pressure. The crude product was purified by column chromatography (DCM/MeOH, 30:1) to afford the desired product IS-100-055 (0.43 g, 58% yield) as a colourless oil.

$^1H$ NMR (400 MHz, $CDCl_3$): $\delta_H$ 1.74-1.86 (m, 1H). 1.91-2.08 (m, 4H), 2.20-2.39 (m, 3H), 2.46-2.71 (m, 2H), 2.80-2.93 (m, 1H), 4.68 (s, 1H), 4.88-5.11 (m, 5H), 5.63 (d, J=1.2 Hz, 2H), 7.28-7.39 (m, 15H).

$^{31}P$ NMR (162 MHz, $CDCl_3$): $\delta_P$ 56.23, 55.81.

ESI MS: 623.2 ([M+Na]$^+$).

HR ESI MS: calcd for $C_{31}H_{34}O_8ClPNa$: 623.15720; found: 623.15742.

Dibenzyl 2-(((benzyloxy)(3-((((4R-4-((3R,10S,12S,13R,17R)-3,12-dihydroxy-10,13-dimethylhexadecahydro-1H-cyclopenta[a]phenanthren-17-yl)pentanoyl)oxy)methoxy)-3-oxopropyl)phosphoryl)methyl)pentanedioate (IS-100456)

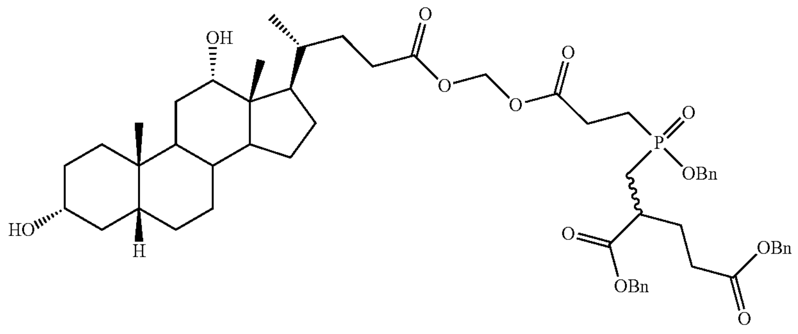 [SMILES: C[C@H](CCC(=O)OCOC(=O)CCP(=O)(CC(CCC(=O)OCc1ccccc1)C(=O)OCc1ccccc1)OCc1ccccc1)[C@H]1CCC2C3CC[C@@H]4C[C@H](O)CC[C@]4(C)C3C[C@H](O)[C@@]21C]

Compound IS-100-055 (0.12 g, 0.20 mmol, 1 equiv.), deoxycholic acid (0.16 g, 0.40 mmol, 2 equiv.) and $Cs_2CO_3$ (77 mg, 0.22 mmol, 1.1 equiv.) were suspended in anhydrous DMF (10 mL). The resulting mixture was stirred under inert atmosphere for 16 h at rt. DMF was evaporated, the residue was dissolved in DCM (50 mL) and washed with 1M aq. HCl (10 mL) and brine (10 mL), dried over $Na_2SO_4$ and volatiles were evaporated. The crude product was purified by column chromatography (DCM/MeOH, 20:1) to afford the desired compound IS-100-056 as a colorless foam (0.13 g, 68% yield). $^1$H NMR (400 MHz, $CDCl_3$): $\delta_H$ 0.65 (s, 3H), 0.88 (s, 3H), 0.94 (d, J=6.0 Hz, 3H), 0.97-2.66 (m, 37H), 3.54-3.62 (m, 1H), 3.94 (t, J=3.1 Hz, 1H), 4.88-5.08 (m, 6H), 5.66-5.71 (m, 2H), 7.26-7.36 (m, 15H).

$^{31}$P NMR (162 MHz, $CDCl_3$): $\delta_P$ 56.47, 56.43, 56.06, 56.02.

ESI MS: 979.5 ([M+Na]$^+$).

HR ESI MS: calcd for $C_{55}H_{74}O_{12}P$: 957.49124; found: 957.49036.

2-(((3-((((4R)-4-((3R,10S,12S,13R,17R)-3,12Z-Dihydroxy-10,13-dimethylhexadecahydro-1H-cyclopenta[a]phenanthren-17-yl)pentanoyl)oxy)methoxy)-3-oxopropyl)(hydroxy)phosphoryl)methyl)pentanedioic acid (12, IS-100-M58)

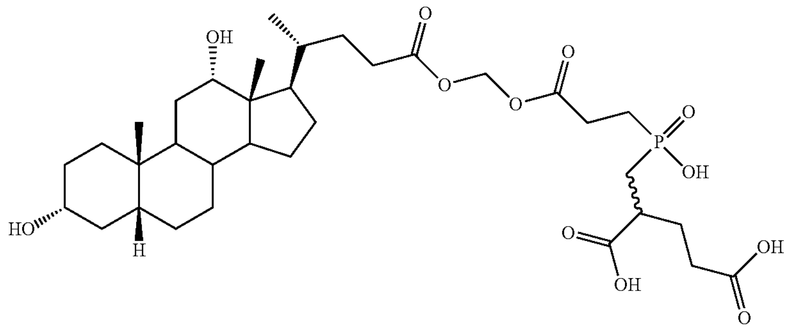 [SMILES: C[C@H](CCC(=O)OCOC(=O)CCP(=O)(O)CC(CCC(=O)O)C(=O)O)[C@H]1CCC2C3CC[C@@H]4C[C@H](O)CC[C@]4(C)C3C[C@H](O)[C@@]21C]

Compound IS-100-056 (0.12 g, 0.012 mmol, 1 equiv.) was dissolved in anhydrous THF (15 mL) and 10% palladium on carbon (30 mg) was added. Reaction flask was evacuated and filled with hydrogen and stirred at rt for 16 h. Palladium on carbon was removed by filtration through Celite™ and volatiles were evaporated under reduced pressure to afford the desired product 12 (66 mg, 77% yield) as a colourless solid.

$^1$H NMR (400 MHz, $CD_3OD$): $\delta_H$ 0.71 (s, 3H), 0.93 (s, 3H), 1.01 (s, 5H), 1.23-1.68 (m, 17H), 1.72-2.17 (m, 12H), 2.16-2.53 (m, 6H), 2.54-2.70 (m, 2H), 2.74-2.68 (m, 1H), 3.53 (s, 1H), 3.87-4.00 (m, 2H), 4.36 (t, J=7.1 Hz, 1H), 5.71-5.80 (m, 2H).

$^{31}$P NMR (162 MHz, $CD_3OD$): $\delta_P$ 53.75, 53.08.

ESI MS: 685.3 ([M−H]$^+$).

HR ESI MS: calcd for $C_{34}H_{54}O_{12}P$: 685.33584; found: 685.33521.

Scheme 8

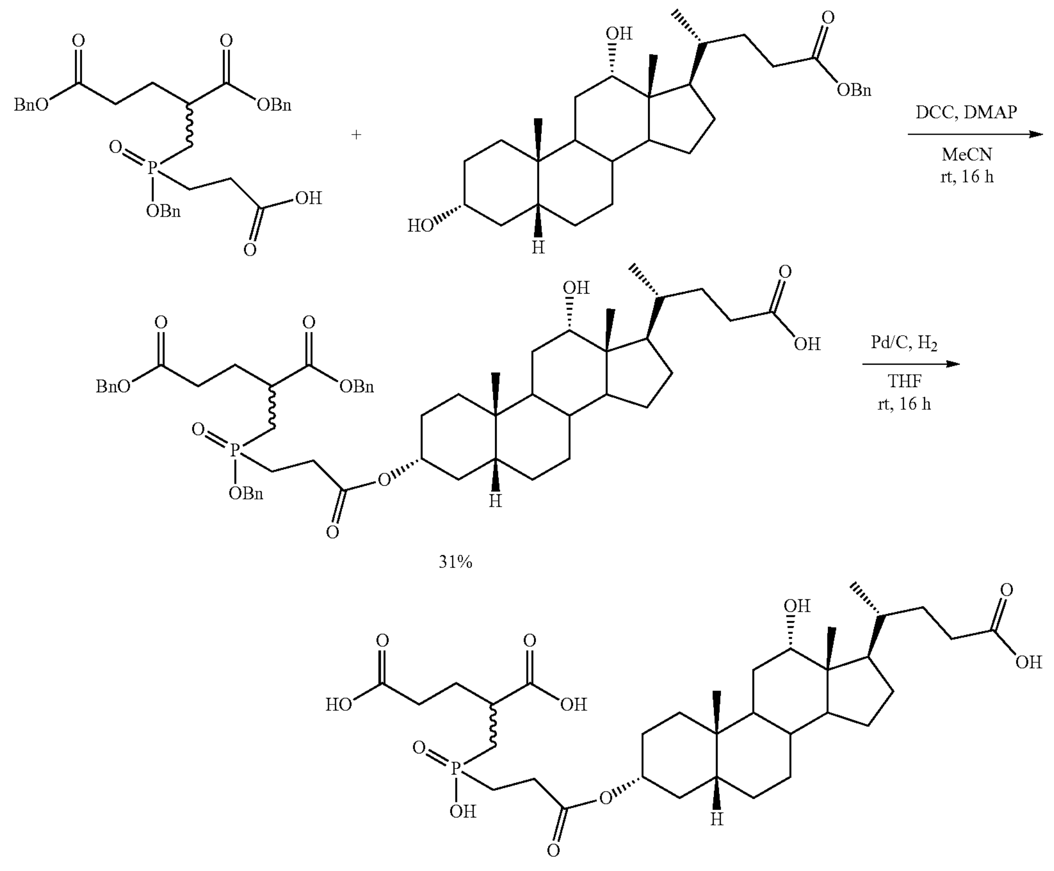

13 IS-100-032 89%

(4R)-4-((3R,10S,12S,13R,17R)-3-((3-((Benzyloxy)(5-(benzyloxy)-2-((benzyloxy)carbonyl)-5-oxopentyl)phosphoryl)propanoyl)oxy)-12-hydroxy-10,13-dimethylhexadecahydro-1H-cyclopenta[a]phenanthren-17-yl)pentanoic acid (IS-100-030)

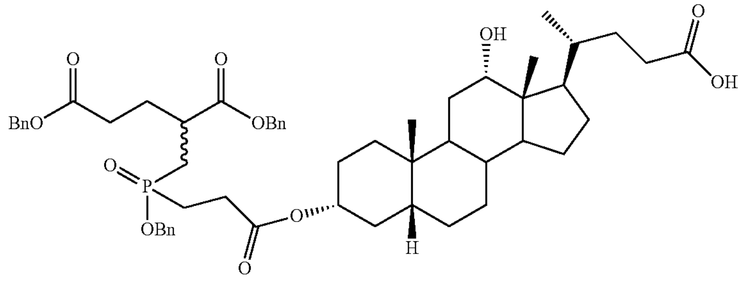 [SMILES: C[C@H](CCC(=O)O)[C@H]1CCC2C3CC[C@@H]4C[C@H](OC(=O)CCP(=O)(CC(CCC(=O)OCc5ccccc5)C(=O)OCc5ccccc5)OCc5ccccc5)CC[C@]4(C)C3C[C@H](O)[C@@]21C]

Compound IS-100-025 (0.35 g, 0.63 2 mmol, 1 equiv.) was dissolved in acetonitrile (10 mL) and benzyl deoxycholate (0.32 g, 0.66 mmol, 1.05 equiv.), DCC (0.14 g, 0.66 mmol, 1.05 equiv.) and DMAP (7.7 mg, 0.06 mmol, 0.1 equiv.) were added. The reaction mixture was stirred at room temperature for 16 h. After completion, DCU was filtered off and volatiles were evaporated under reduced pressure. Residue was purified by column chromatography (DCM/MeOH, 20:1) to afford partially debenzylated product IS-100-030 (0.20 g, 31% yield) as a colourless solid.

$^1H$ NMR (400 MHz, $CDCl_3$): $\delta_H$, 0.63 (s, 3H), 0.87 (s, 3H), 0.90-2.11 (m, 36H), 2.16-2.63 (m, 6H), 2.81-2.97 (m, 1H), 3.92-4.00 (m, 1H), 4.25-4.39 (m, 1H), 5.03-5.20 (m, 6H), 7.27-7.38 (m, 15H).

$^{31}P$ NMR (162 MHz, $CDCl_3$): $\delta_P$ 57.22, 57.13, 56.87.

ESI MS: 949.5 ($[M+Na]^+$).

HR ESI MS: calcd for $Cs_4H_{71}O_{11}NaP$: 949.46262; found: 949.46295.

2-(((3-(((3R,10S,12S,13R,17R)-17-((R)-4-Carboxybutan-2-yl)-12-hydroxy-10,13-dimethylhexadecahydro-1H-cyclopenta[a]phenanthren-3-yl) oxy)-3 oxopropylxhydroxy)phosphoryl)methyl) pentanedioic acid (IS-100-032)

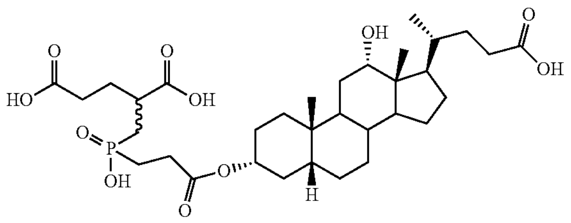 [SMILES: C[C@H](CCC(=O)O)[C@H]1CCC2C3CC[C@@H]4C[C@H](OC(=O)CCP(=O)(O)CC(CCC(=O)O)C(=O)O)CC[C@]4(C)C3C[C@H](O)[C@@]21C]

Compound IS-100-030 (0.18 g, 0.19 mmol, 1 equiv.) was dissolved in anhydrous THF (10 mL) and 10% $X_0$ palladium on carbon (30 mg) was added. Reaction flask was evacuated and filled with hydrogen (1 atm) and stirred at rt for 16 h. Palladium on carbon was removed by filtration through Celite™ and volatiles were evaporated under reduced pressure to afford the desired product (0.13 g, 89% yield) as a white solid.

$^1$H NMR (400 MHz, $CD_3OD$): $\delta_H$ 0.72 (s, 3H), 0.94 (s, 3H), 1.01 (d, J=6.4 Hz, 6H), 1.24-2.45 (m, 32H), 2.49-2.64 (m, 2H), 2.74-2.86 (m, 1H), 3.98 (s, 1H), 4.26-4.39 (m, 1H).

$^{31}$P NMR (162 MHz, $CD_3OD$): $\delta_P$ 58.29, 58.27, 57.97, 57.92.

ESI MS: 655.4 ([M−H]$^+$).

HR ESI MS: calcd for $C_{33}H_{51}O_{11}P$: 655.32527; found: 655.32451.

Scheme 9

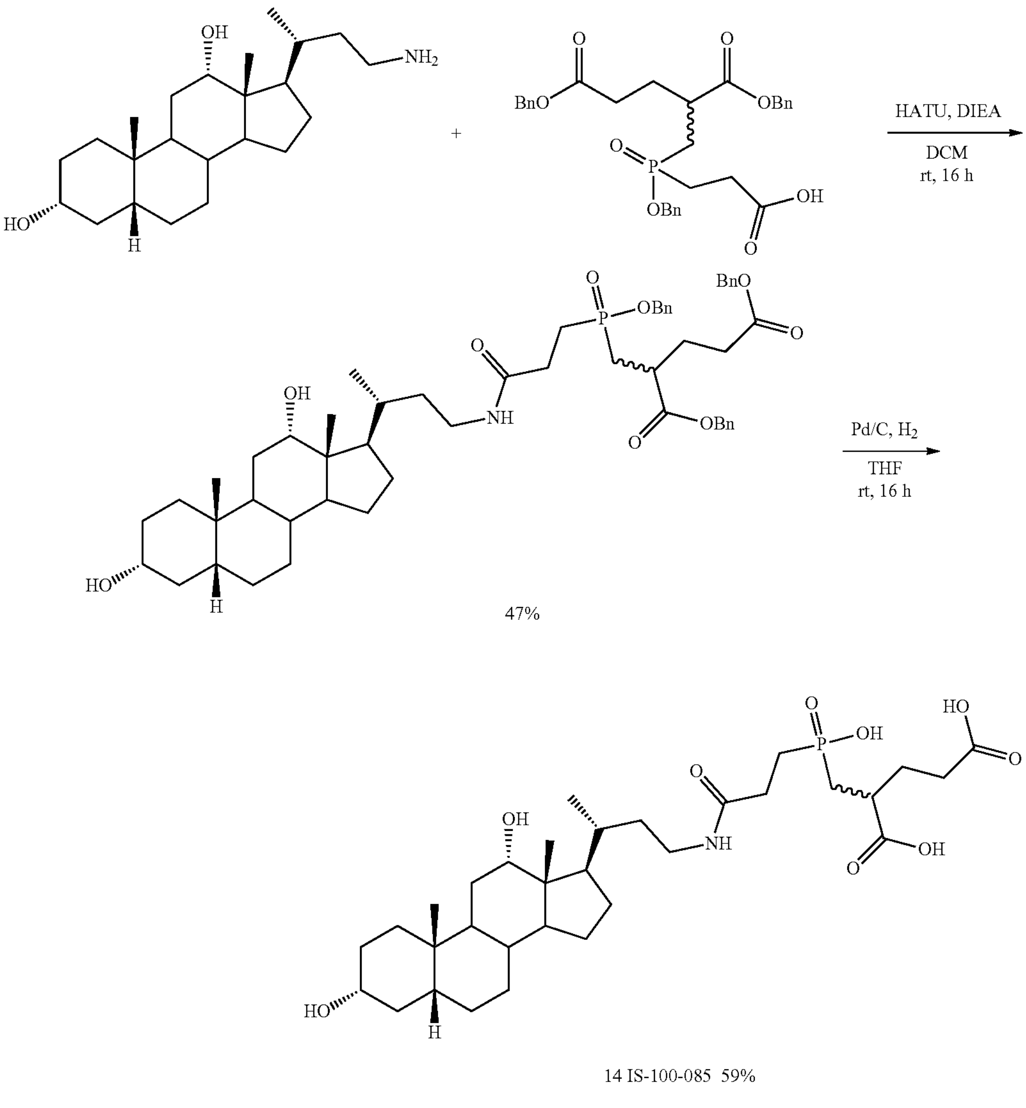

14 IS-100-085 59%

(2R,4aS,6S,7R)-7-((S)-4-Amino-2-methylbutyl)-4a,7-dimethyltetradecahydrophenanthrene-2,6-diol (IS-100-076)

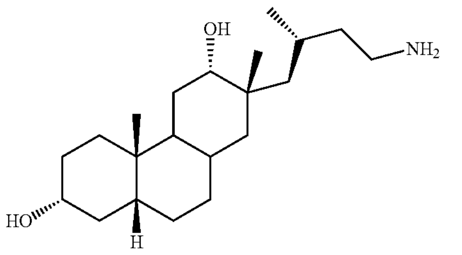

Compound was prepared according to the published procedure. $^1$H and $^{13}$C NMR spectra were in agreement with published data (*J. Med. Pharm. Chem.* 1962, 5, 281-2%).

Dibenzyl 2-(((benzyloxy)(3-(((3R)-3-((3R,10S,12S,13R,17R)-3,12-dihydroxy-10,13-dimethylhexadecahydro-1H-cyclopenta[a]phenanthren-17-yl)butyl)amino)-3-oxopropyl)phosphoryl)methyl)pentanedioate (IS-100-080)

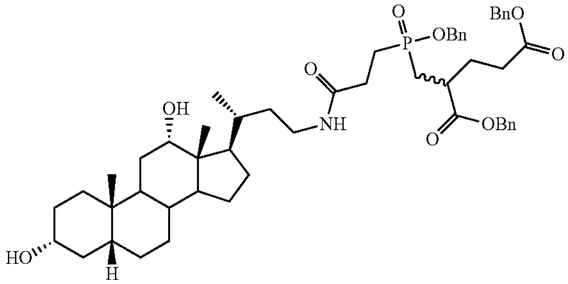 [SMILES: C[C@H](CCNC(=O)CCP(=O)(CC(CCC(=O)OCc1ccccc1)C(=O)OCc1ccccc1)OCc1ccccc1)[C@H]1CCC2C3CC[C@@H]4C[C@H](O)CC[C@]4(C)C3C[C@H](O)[C@@]21C]

Compound IS-100-026 (0.1 g, 0.26 mmol, 1 equiv.) was dissolved in DCM (3 mL) and HATU (0.1 g, 0.26 mmol, 1 equiv.) followed by DIEA (0.14 mL, 0.78 mmol, 3 equiv.) were added. Reaction mixture was stirred for 5 minutes and compound IS-100-076 (0.1 g, 0.26 mmol, 1 equiv.) dissolved in DCM (1 mL) was added. Reaction mixture was stirred at rt for 16 h. Further DCM (20 mL) was added and organic layer was extracted with 1M HCl (10 mL) and brine (10 mL). Organic portion was dried over $Na_2SO_4$ and volatiles were evaporated under reduced pressure. The mixture was purified by column chromatography (DCM/MeOH, 20:1) to afford the desired product IS-100-080 (0.11 g, 47% yield) as a colourless solid.

$^1H$ NMR (400 MHz, $CDCl_3$): $\delta_H$ 0.65 (s, 3H), 0.73-2.18 (m, 34H), 2.18-2.52 (m, 5H), 2.74-2.90 (m, 1H), 3.05-3.34 (m, 2H), 3.48-4.14 (m, 5H), 4.85-5.13 (m, 6H), 6.38 (s, 1H), 7.18-7.44 (m, 15H).

$^{31}P$ NMR (162 MHz, $CDCl_3$): $\delta_P$ 60.14, 59.91.

ESI MS: 920.5 ($[M+Na]^+$).

HR ESI MS: calcd for $Cs_3H_{72}O_9PNa$: 920.48369; found: 920.48320.

2-(((3-(((3R)-3-((3R,10S,12S,13R,17R)-3,12Z-Dihydroxy-10,13-dimethylhexadecahydro-1H-cyclopenta[a]phenanthren-17-yl)butyl)amino)-3-oxopropylxhydroxy)phosphoryl)methyl)pentanedioic acid (14, IS-100-085)

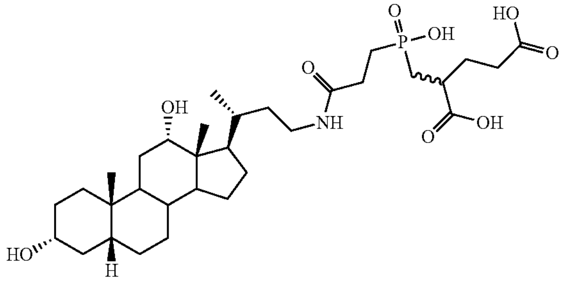 [SMILES: C[C@H](CCNC(=O)CCP(=O)(O)CC(CCC(=O)O)C(=O)O)[C@H]1CCC2C3CC[C@@H]4C[C@H](O)CC[C@]4(C)C3C[C@H](O)[C@@]21C]

Compound IS-100-80 (0.1 g, 0.11 mmol, 1 equiv.) was dissolved in anhydrous THF (10 mL) and 10% palladium on carbon (30 mg) was added. Reaction flask was evacuated and filled with hydrogen (1 atm) and stirred at rt for 16 h. Palladium on carbon was removed by filtration through Celite™ and volatiles were evaporated under reduced pressure to afford the desired product 14 (42 mg, 59% yield) as a white solid.

$^1H$ NMR (400 MHz, $CD_3OD$): $\delta_H$ 0.72 (s, 3H), 0.83-2.09 (m, 36H), 2.12-2.63 (m, 6H), 2.80 (t, J=8.7 Hz, 1H), 3.08-3.28 (m, 2H), 3.46-3.58 (m, 1H), 3.68-3.78 (m, 1H), 3.96 (t, J=2.9 Hz, 1H).

$^{31}P$ NMR (162 MHz, $CD_3OD$): $\delta_P$ 53.71.

ESI MS: 626.3 ($[M-H]^+$).

HR ESI MS: calcd for $C_{32}H_{53}O_9NP$: 626.34634; found: 626.34570.

Scheme 10

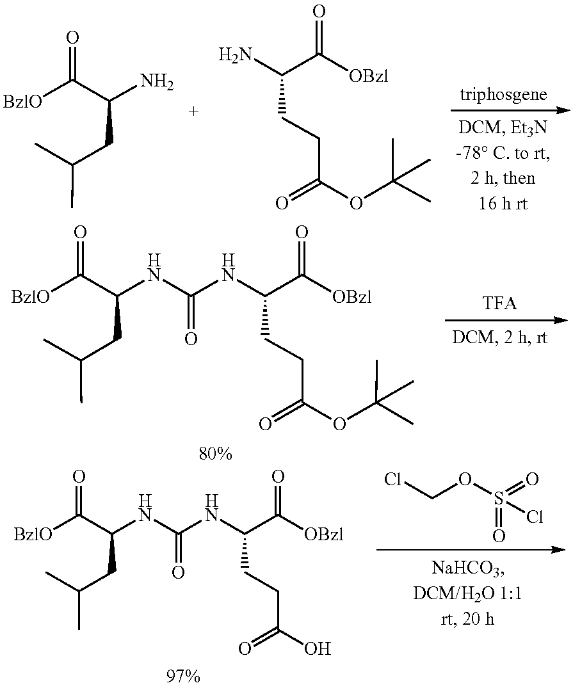

-continued

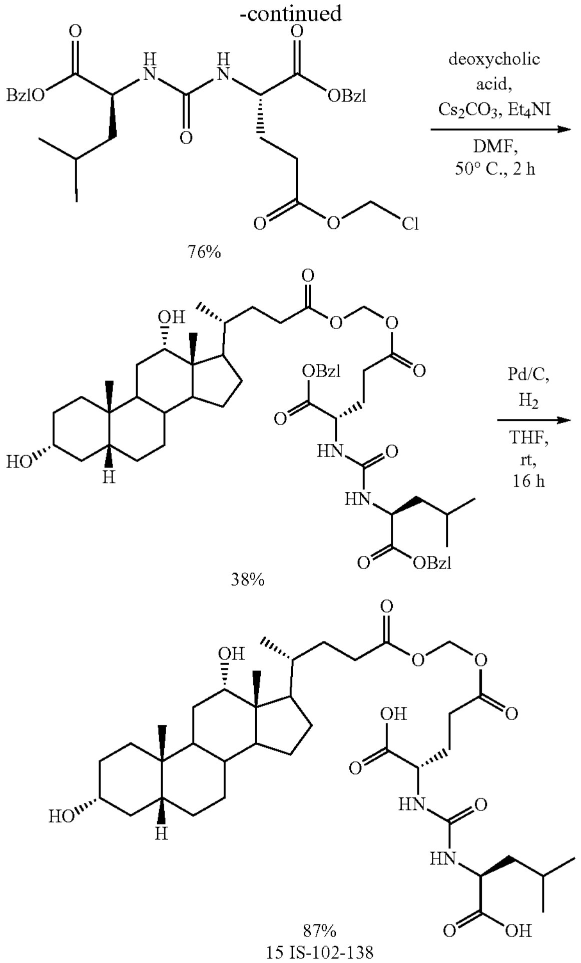

15 IS-102-138

1-Benzyl 5-(ten-butyl) (((S)-1-(benzyloxy)-4-methyl-1-oxopentan-2-yl)carbamoyl)-L-glutamate (AN-1-%6)

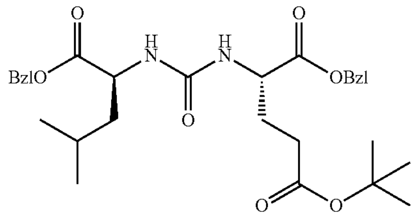

A solution of L-glutamic acid α-benzyl ester 7-tert-butyl ester (1.70 g, 5.80 mmol, 3 equiv.) and DIEA (10.0 mL, 58.0 mmol, 30 equiv.) in anhydrous DCM (80 mL) was added dropwise (during 2 h) to a solution of triphosgene (0.57 g, 1.93 mmol, 1 equiv) in anhydrous DCM (100 mL) at −78° C. under $N_2$ atmosphere. After stirring for another 30 min at −78° C., the cold bath was removed and a solution of L-leucine benzyl ester (1.28 g, 5.80 mmol, 3 equiv.) and DIEA (1.04 mL, 5.80 mmol, 30 equiv.) in anhydrous DCM (20 mL) was added to the mixture at rt. The resulting mixture was stirred overnight (16 h), then concentrated under reduced pressure, quenched with 1M HCl, and extracted with ethyl acetate (200 mL). Organic portion was dried over $Na_2SO_4$ and volatiles were evaporated under reduced pressure. The mixture was purified by column chromatography (cyclohexane/EtOAc, 3:1) to afford the desired product AN-1-%6 (2.50 g, 80% yield) as a colorless solid.

$^1H$ NMR (400 MHz, $CDCl_3$): $\delta_H$ 0.89 (dd, J=6.4, 4.3 Hz, 6H), 1.41 (s, 9H), 1.44-1.71 (m, 3H), 1.85-1.98 (m, 1H), 2.03-2.15 (m, 1H), 2.19-2.38 (m, 2H), 4.47-4.57 (m, 2H), 5.04 (d, J=8.5 Hz, 1H), 5.09-5.20 (m, 4H), 5.27 (d, J=8.1 Hz, 1H), 7.27-7.41 (m, 10H).

$^{13}C$ NMR (101 MHz, $CDCl_3$): $\delta_C$ 22.1, 22.9, 24.9, 28.1, 28.2, 31.6, 42.2, 51.9, 52.8, 65.5, 67.1, 67.3, 80.8, 127.1, 127.8, 128.3, 128.3, 128.4, 128.5, 128.6, 128.7, 128.7, 135.4, 135.6, 156.8, 172.5, 173.0, 174.0.

ESI MS: 541.3 ([M−H]$^+$).

HR ESI MS: calcd for $C_{30}H_{41}O_7N_2$: 541.29083; found: 541.28990.

(S)-5-(Benzyloxy)-4-(3-((S)-1-(benzyloxy)-4-methyl-1-oxopentan-2-yl)ureido)-5-oxopentanoic acid (IS-102-130)

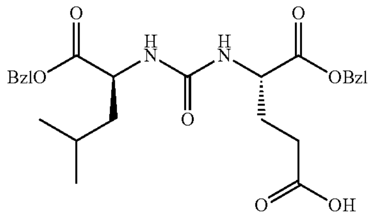

Compound AN-1-96 (2.50 g, 0.82 mmol, 1 equiv.) was dissolved in DCM (1 mL) and trifluoroacetic acid (5 mL) was added and the reaction mixture was stirred at rt for 2 h. Volatiles were evaporated under reduced pressure and the residue was redissolved in DCM (20 mL) and evaporated to remove residual TFA (three times). Crude compound IS-102-130 (2.15 g, 97% yield) was used in the next step without further purification.

$^1H$ NMR (400 MHz, $CDCl_3$): $\delta_H$ 0.78-0.99 (m, 6H), 1.45-1.79 (m, 3H), 1.93-2.13 (m, 1H), 2.18-2.81 (m, 3H), 4.45-4.67 (m, 2H), 5.09-5.29 (m, 4H), 7.28-7.47 (m, 10H).

ESI MS: 483.2 ([M−H]$^+$).

HR ESI MS: calcd for $C_{26}H_{31}O_7N_2$: 483.21367; found: 483.21332.

1-Benzyl 5-(chloromethyl) (((S)-1-(benzyloxy)-4-methyl-1-oxopentan-2-yl)carbamoyl)-L-glutamate (IS-102-131)

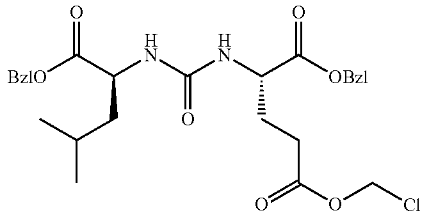

Compound IS-102-130 (2.40 g, 4.95 mmol, 1 equiv.) was dissolved in DCM (75 mL), distilled water (75 mL), $NaHCO_3$ (2.08 g, 24.7 mmol, 5 equiv.) and $Bu_4N^+HSO_4^-$ (0.17 g, 0.49 mmol, 0.1 equiv.) were added. The reaction mixture was vigorously stirred for 5 minutes at rt and chloromethyl chlorosulphate (0.75 mL, 7.40 mmol, 1.5 equiv.) in DCM (10 mL) was added during 1 minute. The resulting mixture was stirred for 20 h at rt. Further DCM (50 mL) was added and phases were separated. Aqueous phase was extracted with DCM (3×50 mL) and combined organic fractions were washed with sat. NaCl (50 mL), dried over $Na_2SO_4$ and all volatiles were evaporated under reduced pressure. The crude product was purified by column chromatography (cyclohexane/EtOAc, 3:1) to afford the desired product IS-102-131 (1.92 g, 76% yield) as a colorless solid.

$^1H$ NMR (400 MHz, $CDCl_3$): $\delta_H$ 0.82-0.98 (m, 6H), 1.43-1.75 (m, 3H), 1.91-2.07 (m, 1H), 2.14-2.29 (m, 1H), 2.35-2.54 (m, 2H), 4.47-4.62 (m, 2H), 5.02-5.26 (m, 6H), 5.64 (d, J=1.5 Hz, 2H), 7.29-7.45 (m, 10H).

$^{13}C$ NMR (101 MHz, $CDCl_3$): $\delta_C$ 22.1, 22.9, 24.9, 27.9, 30.2, 42.1, 51.9, 52.5, 67.2, 67.6, 68.9, 128.3, 128.4, 128.4, 128.5, 128.7, 128.7, 128.8, 135.3, 135.6, 156.8, 171.2, 172.7, 174.1.

ESI MS: 533.2 ($[M-H]^+$).

HR ESI MS: calcd for $C_{27}H_{34}O_7ClN_2$: 533.20491; found: 533.20478.

1-Benzyl 5-((((4R)-4-((3R,10S,12S,13R,17R)-3,12-dihydroxy-10,13-dimethylhexadecahydro-1H-cyclopenta[a]phenanthren-17-yl)pentanoyl)oxy)methyl) (((S)-1-(benzyloxy)-4-methyl-1-oxopentan-2-yl) carbamoyl)-L-glutamate (IS-102-133)

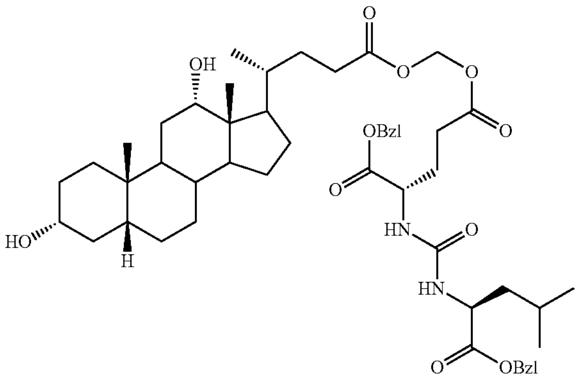

Compound IS-102-131 (1.90 g, 3.55 mmol, 1 equiv.), deoxycholic acid (3.49 g, 8.88 mmol, 2.5 equiv.), tetrabutylammonium iodide (35 mg, 0.1 mmol) and $Cs_2CO_3$ (1.16 g, 3.55 mmol, 1 equiv.) were suspended in anhydrous DMF (10 mL). The resulting mixture was stirred under inert atmosphere for 2 h at 50° C. DMF was evaporated, the residue was dissolved in EtOAc (100 mL) and washed with 1M HCl (40 mL), sat. $NaHCO_3$ (40 mL) and brine (40 mL), dried over $Na_2SO_4$ and volatiles were evaporated. The crude product was purified by column chromatography (EtOAc/cyclohexane, 2:1) to afford the desired compound IS-102-133 as a colorless solid (1.20 g, 38% yield).

$^1H$ NMR (400 MHz, $CDCl_3$): $\delta_H$ 0.67 (s, 3H), 0.88-0.93 (m, 9H), 0.96 (d, J=6.2 Hz, 3H), 1.01-1.98 (m, 26H), 2.14-2.52 (m, 5H), 3.61 (td, J=10.9, 5.3 Hz, 1H), 3.96 (t, J=3.0 Hz, 1H), 4.45-4.60 (m, 2H), 5.00-5.24 (m, 6H), 5.63-5.78 (m, 2H), 7.29-7.43 (m, 10H).

$^{13}C$ NMR (101 MHz, $CDCl_3$): $\delta_C$ 12.9, 17.5, 22.1, 23.0, 23.3, 23.8, 24.9, 26.3, 27.2, 27.6, 27.8, 28.8, 30.3, 30.6, 31.0, 33.8, 34.3, 35.2, 35.3, 36.2, 36.6, 42.1, 42.2, 46.7, 47.3, 48.4, 51.9, 52.6, 67.1, 67.5, 72.0, 73.3, 79.8, 128.3, 128.4, 128.5, 128.6, 128.7, 128.8, 135.3, 135.6, 156.9, 161.0, 161.8, 171.8, 172.6, 173.3, 174.0.

ESI MS: 889.5 ($[M-H]^+$).

HR ESI MS: calcd for $C_{51}H_{73}O_{11}N_2$: 889.52089; found: 889.52073.

(2S,6S,16R)-6-Carboxy-16-((3R,10S,12S,13R,17R)-3,12-dihydroxy-10,13-dimethylhexadecahydro-1H-cyclopenta[a]phenanthren-17-yl)-2-isobutyl-4,9,13-trioxo-10,12-dioxa-3,5-diazaheptadecanoic acid (15, IS-102-138)

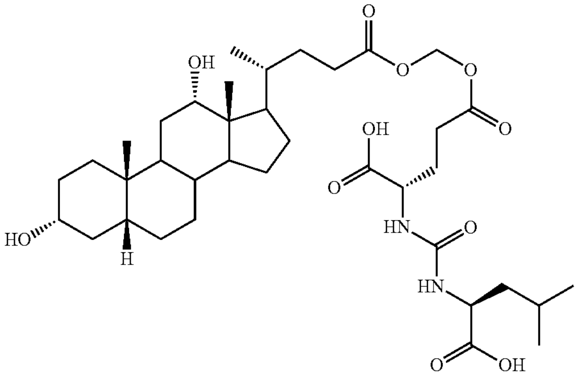 [SMILES: CC(C)C[C@H](NC(=O)N[C@@H](CCC(=O)OCOC(=O)CC[C@@H](C)C1CCC2C3CC[C@@H]4C[C@H](O)CC[C@]4(C)C3C[C@H](O)[C@@]21C)C(=O)O)C(=O)O]

Compound IS-102-133 (0.89 g, 0.1 mmol, 1 equiv.) was dissolved in anhydrous THF (20 mL) and 10% palladium on carbon (50 mg) was added. Reaction flask was evacuated and filled with hydrogen (1 atm) and stirred at rt for 16 h. Palladium on carbon was removed by filtration through Celite™ and volatiles were evaporated under reduced pressure to afford the desired product 15 (0.62 g, 87% yield) as a white solid.

$^1H$ NMR (400 MHz, DMSO-$d_6$): $\delta_H$ 0.59 (s, 3H), 0.78-0.94 (m, 12H), 0.96-1.87 (m, 31H), 1.90-2.02 (m, 1H), 2.19-2.45 (m, 4H), 3.78 (s, 1H), 4.03-4.15 (m, 2H), 4.20 (bs, 1H), 4.45 (bs, 1H), 5.66 (q, J=5.9 Hz, 2H), 6.27 (dd, J=16.8, 8.4 Hz, 2H).

$^{13}C$ NMR (101 MHz, DMSO-$d_6$): $\delta_C$ 12.4, 16.8, 21.7, 22.8, 23.1, 23.5, 24.3, 26.1, 27.0, 27.2, 27.2, 28.6, 29.7, 30.2, 30.3, 30.4, 32.9, 33.8, 34.9, 35.2, 35.6, 36.3, 41.1, 41.6, 46.0, 46.1, 47.5, 50.9, 51.5, 69.9, 71.0, 79.0, 157.2, 171.2, 172.3, 173.9, 175.0.

ESI MS: 731.4 ($[M+Na]^+$).

HR ESI MS: calcd for $C_{37}H_{60}O_{11}N_2Na$: 731.40893; found: 731.40915.

Scheme 11
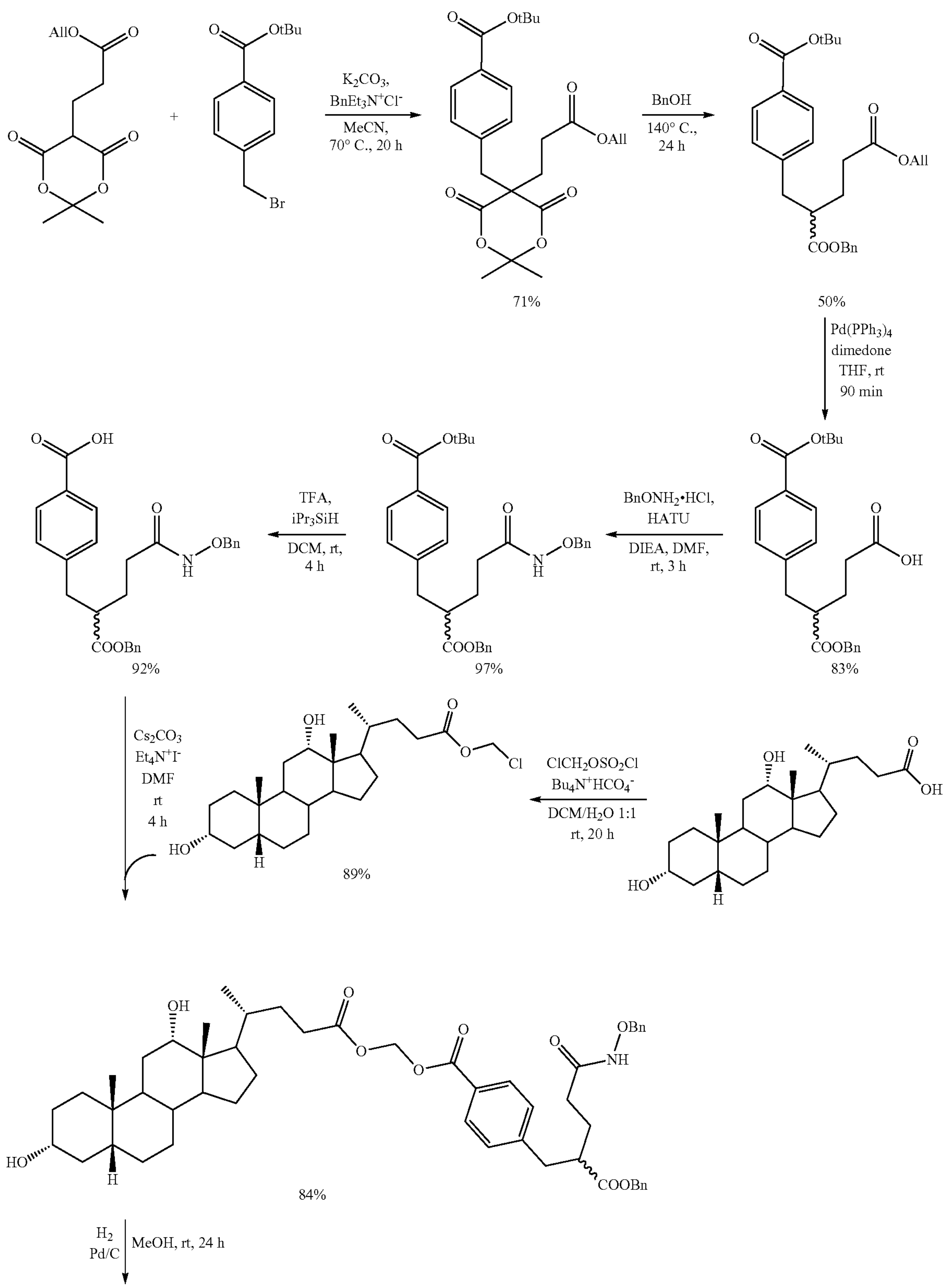

-continued

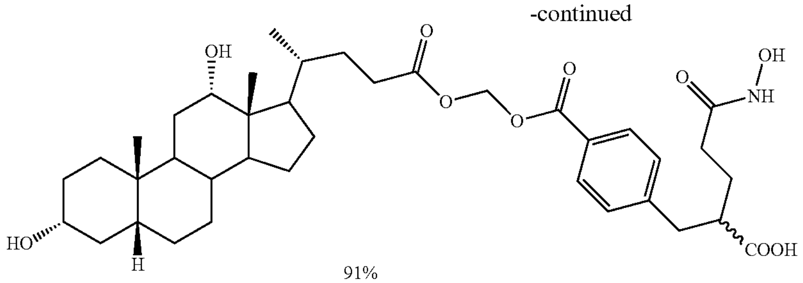

91%

16 TT-220420 tert-Butyl 4-((5((allyloxy)-3-oxopropyl)-22-dimethyl-4,6-dioxo-1,3-dioxan-5-yl)methyl)benzoate (TT-110320)

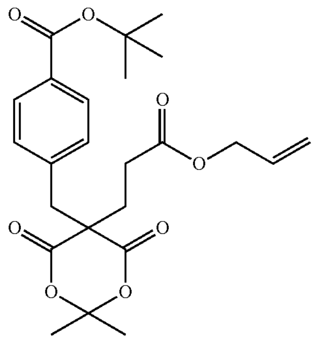 [SMILES: C=CCOC(=O)CCC1(Cc2ccc(C(=O)OC(C)(C)C)cc2)C(=O)OC(C)(C)OC1=O]

Mixture of starting material LTP487 (6.28 g, 24.5 mmol, 1 equiv.), benzyltriethylammonium chloride (5.58 g, 24.5 mmol, 1 equiv.) and $K_2CO_3$ (3.39 g, 24.5 mmol, 1 equiv.) in anhydrous MeCN (100 ml) was heated to 70° C. for 20 min under inert. Then, a solution of tert-butyl 4-(bromomethyl) benzoate (8.00 g, 29.5 mmol, 1.2 equiv.) in anhydrous MeCN (100 ml) was added and the mixture was stirred at 70° C. overnight (20 h). The solvent was evaporated, EtOAc (200 ml) was added and the organic phase was washed with aq. $KHSO_4$ (200 ml), dried over $MgSO_4$ and concentrated. The residue was purified on a silica gel column in 20-25% acetone/hexane followed by PR flash chromatography on 415 g C18 Aq column in 50-100% MeCN/$H_2O$ gradient (20 min, 140 mi/min). Product TT-110320 was isolated in 71% yield (7.75 g) of colorless solid.

$^1$H NMR (400 MHz, $CDCl_3$): $\delta_H$ 0.74 (s, 3H), 1.53 (s, 9H), 1.58 (s, 3H), 2.37-2.44 (m, 2H), 2.44-2.51 (m, 2H), 3.34 (s, 2H), 4.55 (dm, J=5.7 Hz, 2H), 5.21 (dm, J=10.4 Hz, 1H), 5.29 (dm, J=17.1 Hz, 1H), 5.81-5.93 (m, 1H), 7.20 (d, J=8.0 Hz, 2H), 7.85 (d, J=8.0 Hz, 2H).

$^{13}$C NMR (101 MHz, $CDCl_3$): $\delta_C$ 28.22, 29.27, 29.33, 29.92, 35.29, 43.18, 56.03, 65.74, 81.31, 106.16, 118.87, 129.94, 130.43, 131.65, 131.86, 139.55, 165.29, 168.21, 170.87.

ESI MS: 469.2 ($[M+Na]^+$).

HR ESI MS: calcd for $C_{24}H_{30}O_8Na$: 469.18329; found: 469.18320.

5-Allyl 1-benzyl 2-(4-(tert-butoxycarbonyl)benzyl) pentanedioate (TT-250320)

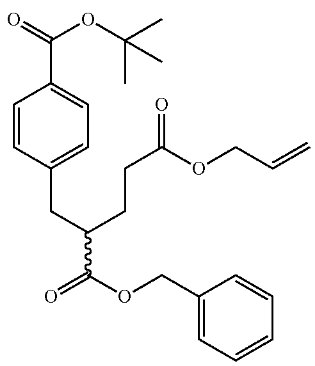 [SMILES: C=CCOC(=O)CCC(Cc1ccc(C(=O)OC(C)(C)C)cc1)C(=O)OCc1ccccc1]

A solution of TT-110320 (7.75 g, 17.4 mmol, 1 equiv.) in anhydrous BnOH (45 ml) was heated to 140° C. for 24 h under inert. The mixture was concentrated at 105-110° C. and the residue was purified using RP flash chromatography on 415 g C18 Aq column in 50-100% MeCN/$H_2O$ gradient (20 min, 150 ml/min). Product TT-250320 was isolated in 50% yield (3.96 g) of syrup.

$^1$H NMR (400 MHz, $CDCl_3$): $\delta_H$ 1.53 (s, 9H), 1.85-2.03 (m, 2H), 2.27-2.43 (m, 2H), 2.75-2.87 (m, 2H), 2.95-3.03 (m, 1H), 4.55 (dt, J=5.8, 1.4 Hz, 2H), 5.00 (d, J=12.2 Hz, 1H), 5.06 (d, J=12.2 Hz, 1H), 5.22 (dq, J=10.4, 1.3 Hz, 1H), 5.29 (dq, J=17.2, 1.5 Hz, 1H), 5.88 (ddt, J=17.2, 10.4, 5.8 Hz, 1H), 7.13-7.19 (m, 4H), 7.28-7.32 (m, 3H), 7.85 (dm, J=8.4 Hz, 2H).

$^{13}$C NMR (101 MHz, $CDCl_3$): $\delta_C$ 27.12, 28.31, 31.81, 38.46, 46.55, 65.29, 66.46, 80.92, 118.40, 128.32 (2C), 128.58, 128.83, 129.72, 130.43, 132.16, 135.68, 143.55, 165.72, 172.39, 174.40.

ESI MS: 475.2 ($[M+Na]^+$).

HR ESI MS: calcd for $C_{27}H_{32}O_6Na$: 475.20911; found: 475.20880.

5-(Benzyloxy)-4-(4-(tert-butoxycarbonyl)benzyl)-5-oxopentanoic acid (TT-270320)

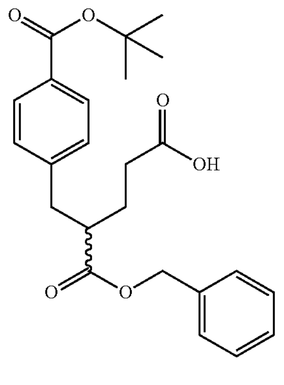 [SMILES: CC(C)(C)OC(=O)c1ccc(CC(CCC(=O)O)C(=O)OCc2ccccc2)cc1]

A solution of TT-250320 (3.93 g, 8.69 mmol, 1 equiv.) and dimedone (1.46 g, 10.42 mmol, 1.2 equiv.) in anhydrous THF (120 ml) was treated with a solution of $Pd(PPh_3)_4$ (400 mg, 0.35 mmol, 0.04 equiv.) in THF (40 ml). The mixture was stirred for 90 min at rt. Solvent was evaporated and the residue was purified using RP flash chromatography on 415 g C18 Aq column in 25-100% $MeCN/H_2O$+0.1% HCOOH gradient (30 min, 150 ml/min). Product TT-270320 was isolated in 83% yield (2.98 g) of colorless oil.

$^1H$ NMR (400 MHz, $CDCl_3$): $\delta_H$ 1.60 (s, 9H), 1.83-2.03 (m, 2H), 2.28-2.46 (m, 2H), 2.76-2.88 (m, 2H), 2.95-3.04 (m, 1H), 5.00 (d, J=12.2 Hz, 1H), 5.07 (d, J=12.2 Hz, 1H), 7.13-7.20 (m, 4H), 7.28-7.32 (m, 3H), 7.85 (dm, J=8.2 Hz, 2H).

$^{13}C$ NMR (101 MHz, $CDCl_3$): $\delta_C$ 26.81, 28.34, 31.61, 38.48, 46.48, 66.58, 81.02, 128.40 (2C), 128.63, 128.86, 129.78, 130.49, 135.63, 143.46, 165.79, 174.37, 178.54.

ESI MS: 435 ($[M+Na]^+$).

HR ESI MS: calcd for $C_{27}H_{32}O_6Na$: 435.17781; found: 435.17790.

tert-Butyl 4-(5-((benzyloxy)amino)-2-((benzyloxy) carbonyl)-5-oxopentyl)benzoate (TT-300320)

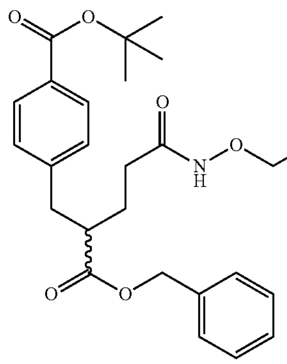

A solution of TT-270320 (2.94 g, 7.13 mmol, 1 equiv.) in anhydrous DMF (15 ml) was cooled down to 0° C., then treated with DIEA (5.0 ml, 28.5 mmol, 4 equiv.) and subsequently with a solution of HATU (2.98 g, 7.84 mmol, 1.1 equiv.) in DMF (10 ml). The resulting mixture was stirred 10 min at 0° C. and then treated with a solution of O-benzylhydroxylamine hydrochloride (1.25 g, 7.84 mmol, 1.1 equiv.) and DIEA (1.4 ml, 7.84 mmol, 1.1 equiv.) in DMF (10 ml). Reaction mixture was stirred 3 h at rt, then concentrated and purified using RP flash chromatography on 415 g C18 Aq column in 30-100% $MeCN/H_2O$ gradient (30 min, 150 ml/min). Product TT-300320 was obtained in 97% yield (3.58 g) of colorless solid.

$^1H$ NMR (400 MHz, $CDCl_3$): $\delta_H$ 1.59 (s, 9H), 1.82-2.47 (m, 4H), 2.69-2.85 (m, 2H), 2.96 (dd, J=13.3, 8.6 Hz, 1H), 4.62-4.91 (m, 2H), 4.93-5.05 (m, 2H), 7.10-7.19 (m, 4H), 7.25-7.30 (m, 3H), 7.35 (bs, 5H), 7.84 (dm, J=8.2 Hz, 2H).

$^{13}C$ NMR (101 MHz, $CDCl_3$): $\delta_C$ 27.77, 28.32, 30.60, 38.44, 46.57, 66.43, 78.24, 80.96, 128.44, 128.53, 128.58, 128.63, 128.74, 128.81, 129.30, 129.73, 130.43, 135.36, 135.71, 143.48, 165.75, 169.74, 174.43.

ESI MS: 540.2 ($[M+Na]^+$).

HR ESI MS: calcd for $C_{31}H_{35}O_6NNa$: 540.23566; found: 540.23572.

4-(5-((Benzyloxy)amino)-2-((benzyloxy)carbonyl)-5-oxopentyl)benzoic acid (TT-010420)

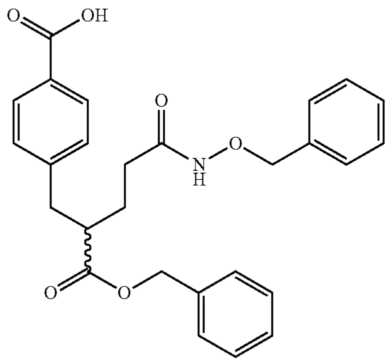 [SMILES: O=C(CCC(Cc1ccc(C(=O)O)cc1)C(=O)OCc1ccccc1)NOCc1ccccc1]

A solution of TT-300320 (3.52 g, 6.80 mmol, 1 equiv.) and $iPr_3SiH$ (1.4 ml, 6.80 mmol, 1 equiv.) in anhydrous $CH_2Cl_2$ (40 ml) was cooled down to 0° C. and treated with TFA (20 ml). The resulting mixture was stirred 4 h at RT and volatiles were evaporated. The syrupy residue crystallized after addition of small amount of MeCN and sonication. Resulting suspension was diluted $Et_2O$ and hexane. The crystals were filtered off and washed with $Et_2O$-hexane. Product TT-010420 was obtained in 92% yield (2.90 g) of colorless solid.

$^1H$ NMR (400 MHz, $CDCl_3$): $\delta_H$ 1.84-2.46 (m, 4H), 2.71-2.88 (m, 2H), 3.00 (dd, J=13.3, 8.6 Hz, 1H), 4.65-4.92 (m, 2H), 4.93-5.09 (m, 2H), 7.14-7.22 (m, 4H), 7.26-7.31 (m, 3H), 7.36 (bs, 5H), 7.95 (dm, J=8.2 Hz, 2H).

$^{13}C$ NMR (101 MHz, $CDCl_3$): $\delta_C$ 27.91, 30.66, 38.55, 46.49, 66.57, 78.33, 128.40-128.87 (m, 6C), 129.13, 129.34, 130.51, 135.30, 135.65, 144.89, 169.93, 171.38, 174.45.

ESI MS: 484.2 ($[M+Na]^+$).

HR ESI MS: calcd for $C_{27}H_{27}O_6NNa$: 484.17306; found: 484.17268.

Chloromethyl (R)-4-((3R,5R,8R,9S,10S,12S,13R,14S,17R)-3,12-dihydroxy-10,13-dimethylhexadecahydro-1H-cyclopenta[a]phenanthren-17-yl)pentanoate (TT-170420)

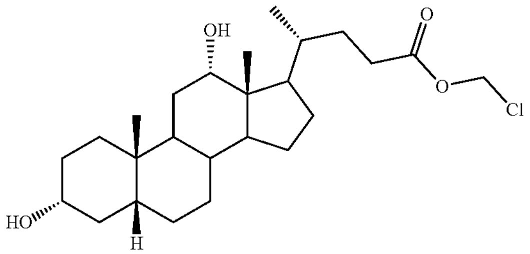 [SMILES: C[C@H](CCC(=O)OCCl)C1CCC2C3CC[C@@H]4C[C@H](O)CC[C@]4(C)C3C[C@H](O)[C@@]21C]

Deoxycholic acid (5.50 g, 14.0 mmol, 1 equiv.) and $NaHCO_3$ (5.88 g, 70.0 mmol, 5 equiv.) were suspended in water (100 ml), then $Bu_4NHSO_4$ (475 mg, 1.4 mmol, 0.1 equiv.) H and $CH_2Cl_2$ (100 ml) were added and the resulting mixture was stirred and cooled down to 0° C. A solution of chloromethyl chlorosulfonate (2.55 ml, 25.2 mmol, 1.8 equiv.) in $CH_2Cl_2$ (10 ml) was slowly added and the mixture was stirred overnight at rt (20 h). Organic portion was separated and the water phase was extracted with $CHCl_3$ (2×100 ml). Combined organic portions were dried ($MgSO_4$) and concentrated. The syrupy residue was chromatographed on a silica gel column in EtOAc. Compound TT-170420 was obtained in 89% yield (5.48 g) as an amorphous foam.

$^1H$ NMR (400 MHz, $CDCl_3$): $\delta_H$ 0.67 (s, 3H), 0.90 (s, 3H), 0.97 (d, J=4.9 Hz, 3H), 0.99-1.89 (m, 22H), 2.25-2.48 (m, 4H), 3.56-3.67 (m, 1H), 3.95-3.99 (m, 1H), 5.66-5.72 (m, 2H).

$^{13}C$ NMR (101 MHz, $CDCl_3$): $\delta_C$ 12.85, 17.37, 23.25, 23.78, 26.24, 27.24, 27.59, 28.80, 30.48, 30.61, 31.16, 33.75, 34.24, 35.13, 35.32, 36.13, 36.42, 42.17, 46.62, 47.33, 48.36, 68.73, 71.99, 73.31, 172.30.

ESI MS: 463.3 ($[M+Na]^+$).

HR ESI MS: calcd for $C_{25}H_{41}O_4ClNa$: 463.25856; found: 463.25840.

(((R)-4-((3R,5R,8R,9S,10S,12S,13R,14S,17R)-3,12-Dihydroxy-10,13-dimethylhexadecahydro-1H-cyclopenta[a]phenanthren-17-yl)pentanoyl)oxy)methyl 4-(5-((benzyloxy)amino)-2-((benzyloxy)carbonyl)-5-oxopentyl)benzoate (TT-200420)

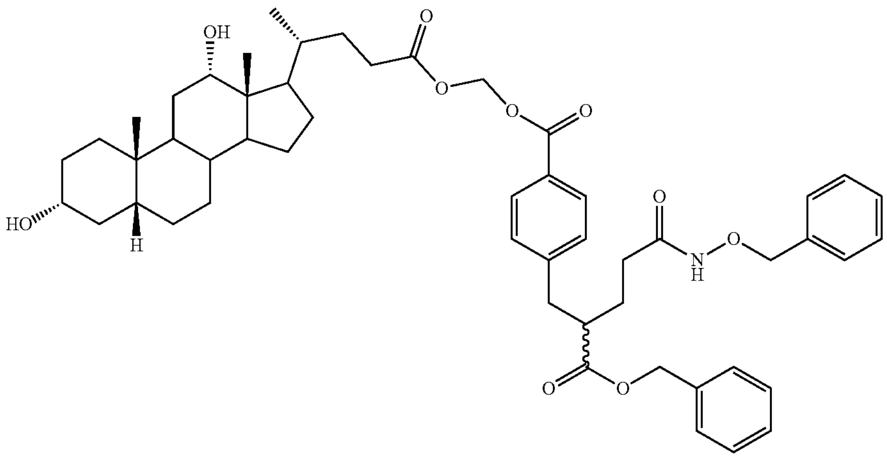 [SMILES: C[C@H](CCC(=O)OCOC(=O)c1ccc(CC(CCC(=O)NOCc2ccccc2)C(=O)OCc2ccccc2)cc1)C1CCC2C3CC[C@@H]4C[C@H](O)CC[C@]4(C)C3C[C@H](O)[C@@]21C]

A mixture of hydroxamate TT-010420 (2.86 g, 6.20 mmol, 1 equiv.) and $Cs_2CO_3$ (2.02 g, 6.20 mmol, 1 equiv.) in anhydrous DMF (12 ml) was stirred and sonicated (10 min). Tetraethylammonium iodide (2.55 g, 9.92 mmol, 1.6 equiv.) was added followed by starting material TT-170420 (4.37 g, 9.92 mmol, 1.6 equiv.). The resulting mixture was stirred 4 h at rt and filtered through celite. The concentrate was purified using RP flash chromatography on 415 g C18 Aq column in 60-100% $MeCN/H_2O$ gradient (25 min, 150 ml/min). Compound TT-200420 was obtained in 84% yield (4.50 g) of colorless syrup.

$^1H$ NMR (400 MHz, $CDCl_3$): $\delta_H$ 0.63 (s, 3H), 0.88 (s, 3H), 0.94 (d, J=6.0 Hz, 3H), 0.96-1.96 (m, 27H), 2.24-2.48 (m, 3H), 2.69-2.86 (m, 2H), 2.96 (dd, J=13.5, 8.8 Hz, 1H), 3.57 (tt, J=10.8, 4.6 Hz, 1H), 3.90-3.95 (m, 1H), 4.63-4.89 (m, 2H), 4.94-5.04 (m, 2H), 5.94-5.99 (m, 2H), 7.13-7.19 (m, 4H), 7.24-7.29 (m, 3H), 7.35 (bs, 5H), 7.90 (d, J=8.2 Hz, 2H).

$^{13}C$ NMR (101 MHz, $CDCl_3$): $\delta_C$ 12.79, 17.36, 23.22, 23.71, 26.21, 27.20, 27.51, 27.81, 28.73, 30.45, 30.62 (2C), 31.14, 33.68, 34.18, 35.14, 35.30, 36.07, 36.41, 38.46, 42.13, 46.49, 46.55, 47.29, 48.27, 66.50, 71.85, 73.16, 78.18, 79.59, 128.36-128.81 (m, 6C), 129.13, 129.30, 130.32, 135.44, 135.62, 145.00, 165.16, 169.66, 173.04, 174.36.

ESI MS: 888.5 ($[M+Na]^+$).

HR ESI MS: calcd for $C_{52}H_{67}O_{10}NNa$: 888.46572; found: 888.46597.

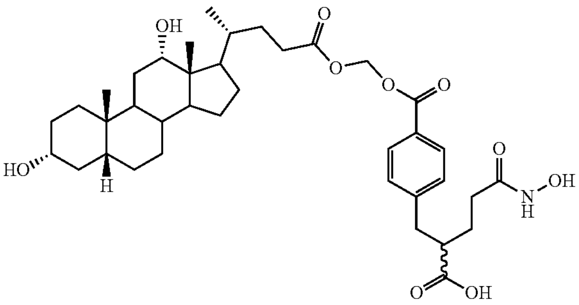 [SMILES: C[C@H](CCC(=O)OCOC(=O)c1ccc(CC(CCC(=O)NO)C(=O)O)cc1)C1CCC2C3CC[C@@H]4C[C@H](O)CC[C@]4(C)C3C[C@H](O)[C@@]21C]

2-(4-(((((R)-4-((3R,5R,8R,9S,1(0S,12S,13R,14S, 17R)-3,12-Dihydroxy-10,13-dimethylhexadecahydro-1H-cyclopenta[a]phenanthren-17-yl)pentanoyl)oxy)methoxy) carbonyl)benzyl)-5-(hydroxyamino)-5-oxopentanoic acid (16, TT-220420)

To a solution of starting material TT-200420 (4.42 g, 5.10 mmol, 1 equiv.) in MeOH (250 ml), Pd/C (5%, 150 mg) was added and the mixture was stirred at rt under atmosphere of $H_2$ for 24 h. The catalyst was filtered off and the filtrate was concentrated. The syrupy residue was chromatographed using RP flash chromatography on 415 g C18 Aq column in 20-100% MeCN/$H_2O$+0.1% HCOOH gradient (30 min, 150 ml/min). Final product 16 was isolated in 91% yield (3.18 g) of colorless lyophilizate.

$^1$H NMR (400 MHz, $CD_3OD$): $\delta_H$ 0.62 (d, J=2.0 Hz, 3H), 0.92 (s, 3H), 0.97 (d, J=6.2 Hz, 3H), 1.07-1.64 (m, 16H), 1.71-1.95 (m, 10H), 2.08-2.25 (m, 2H), 2.29-2.38 (m, 1H), 2.40-2.49 (m, 1H), 2.67-2.75 (m, 1H), 2.88 (dd, J=13.7, 6.1 Hz, 1H), 3.01 (dd, J=13.7, 8.6 Hz, 1H), 3.52 (tt, J=11.2, 4.6 Hz, 1H), 3.89-3.93 (m, 1H), 5.96 (d, J=12.5 Hz, 1H), 5.97 (d, J=12.5 Hz, 1H), 7.35 (d, J=8.3 Hz, 2H), 7.95 (dm, J=8.3 Hz, 2H).

$^{13}$C NMR (101 MHz, $CD_3OD$): $\delta_C$ 13.24, 17.51, 23.77, 24.84, 27.45, 28.41, 28.63, 28.95, 29.87, 31.05, 31.40, 31.90, 31.96, 34.79, 35.29, 36.44, 36.52, 37.18, 37.40, 39.11, 43.60, 47.54, 47.76, 47.77, 48.13, 72.54, 73.99, 80.76, 128.52, 130.44, 131.02, 147.26, 166.34, 171.95, 174.30, 177.97.

ESI MS: 708.4 ($[M+Na]^+$).

HR ESI MS: calcd for $C_{38}H_{55}O_{10}NNa$: 708.37182; found: 708.37158.

Chiral Separation of Compound LTP576 and Synthesis of Enantiomers 2a and 2b

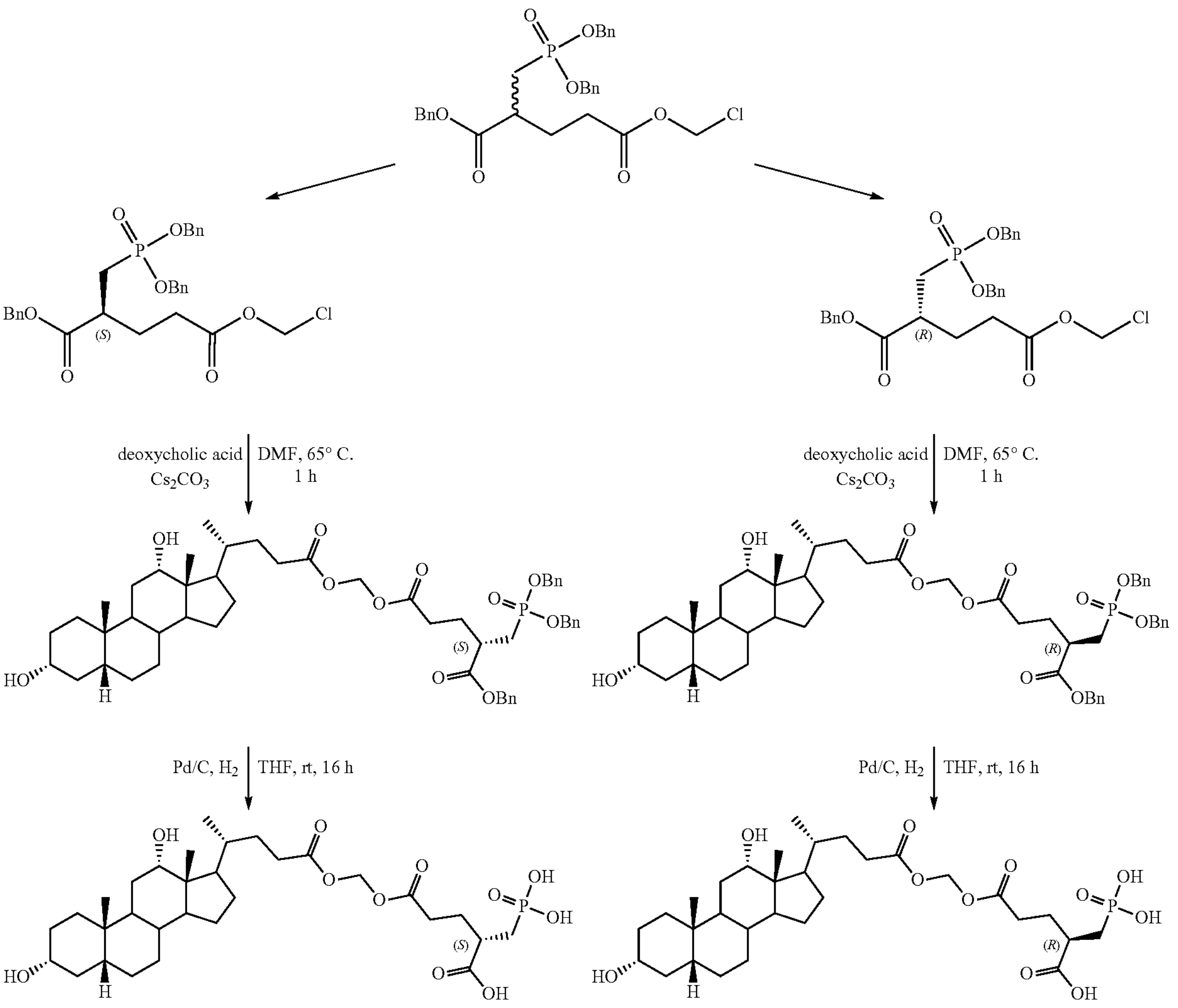

2a S-isomer

2b R-isomer

Example 2

Dextran Sodium Sulfate (DSS)-Induced Colitis 2.1 Experimental Methods

Six- to eight-week-old male C57BM6NHsd mice were acquired from Harlan Laboratories/Envigo (Indianapolis, IN). Animals were housed in the Johns Hopkins animal facility under controlled temperature (25° C.) and photoperiod (12-hour-light/12-hour-dark cycle) with access to standard diet and water (or specified DSS-containing drinking water) ad libitum. All animal studies were approved by the Animal Care and Use Committee of Johns Hopkins University, Baltimore, MD and adhered to all of the applicable institutional and governmental guidelines for the humane treatment of laboratory animals. Mice were housed 4-5 per cage and allowed to acclimate to their environment for at least 5 days before inclusion in experiments. Mice (n=5-30/group) were randomized by body weight into equivalent experimental groups: (a) DSS with vehicle or (b) DSS with test article. Acute colitis was induced by administration of 2.5%-4.0% (w/v) DSS (MW 40,000-50,000; Affymetrix Santa Clara, CA) in the drinking water for 5 days, followed by exposure to freshwater for two days. Daily oral (PO) dosing of vehicle or test article was initiated on study day 0 and was continued until sacrifice on study day 7. Disease activity index (DAI) was calculated daily using the following validated scoring system: (a) weight loss (0=none; 1=1%-5% loss; 2=5%-10% loss; 3=10%-15% loss; 4=more than 15% loss); (b) stool consistency (0=normal; 1=slightly soft; 2=soft but still formed; 3=soft and not formed; 4=watery diarrhea); and (c) bleeding (0=negative; 1=blood test +; 2=blood test ++; 3=visible blood trace in stool; 4=rectal bleeding) as assessed by the ColoScreen occult blood test (Helena Laboratories Product #5076). All data are expressed as mean+/−standard error of the mean (SEM). Statistical analysis was performed using GraphPad Prism 8.0. DAI were compared using 2-way ANOVA. P values of less than 0.05 were considered statistically significant.

2.2 Results

Figure 1A:
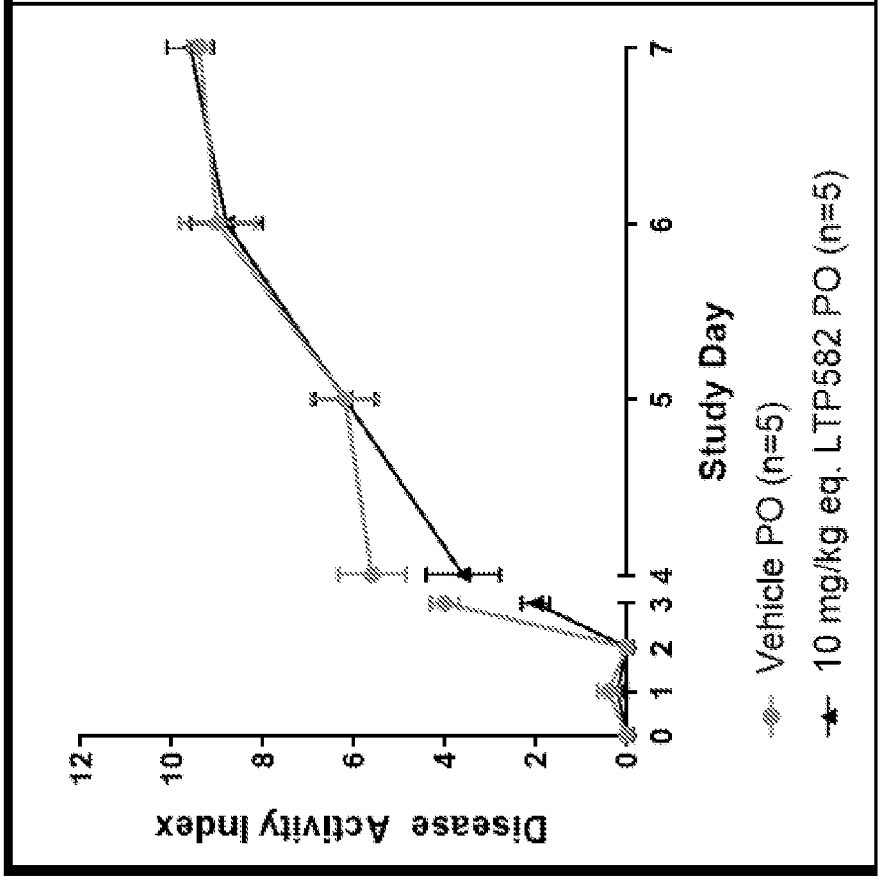
Figure 1B:
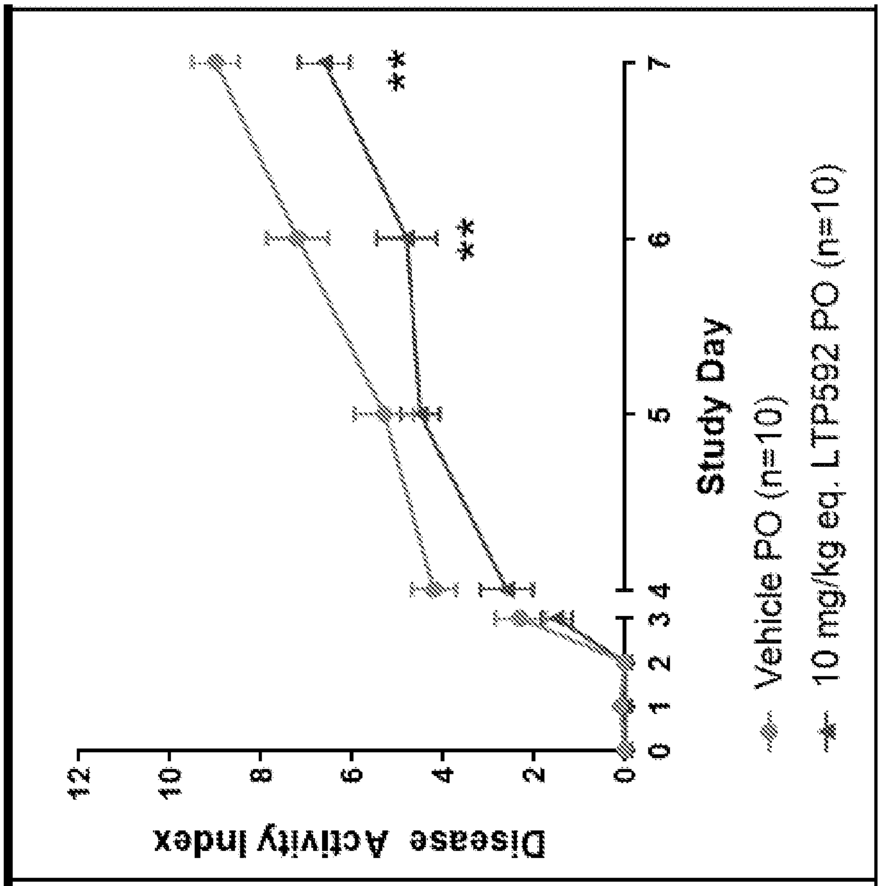
Figure 1D:
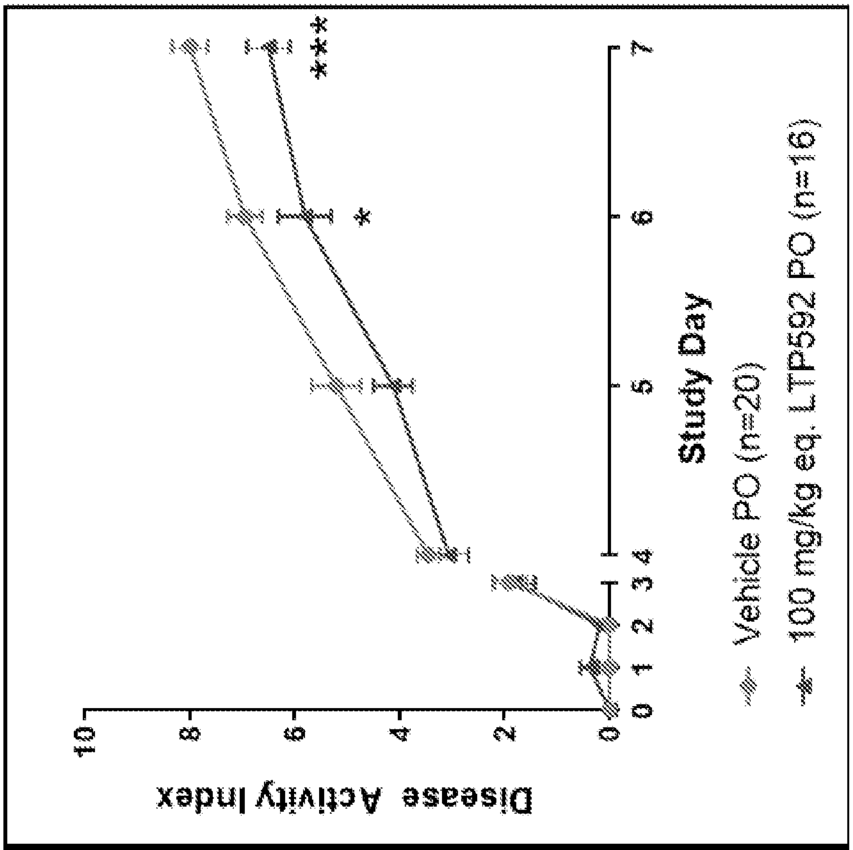
Figure 1C:
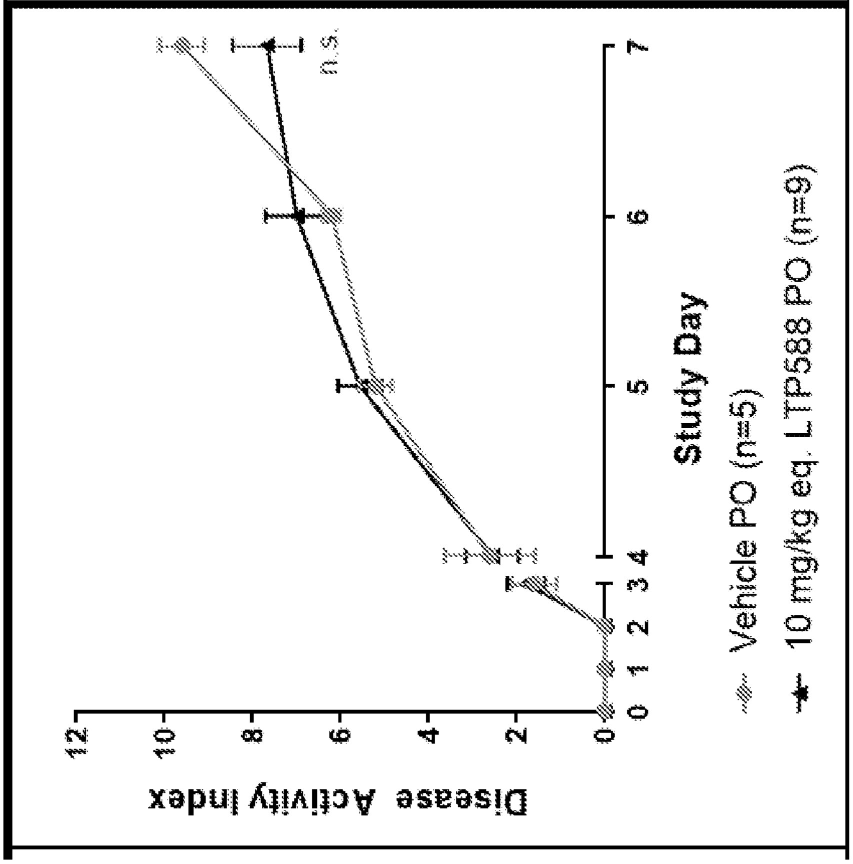
Figure 1F:
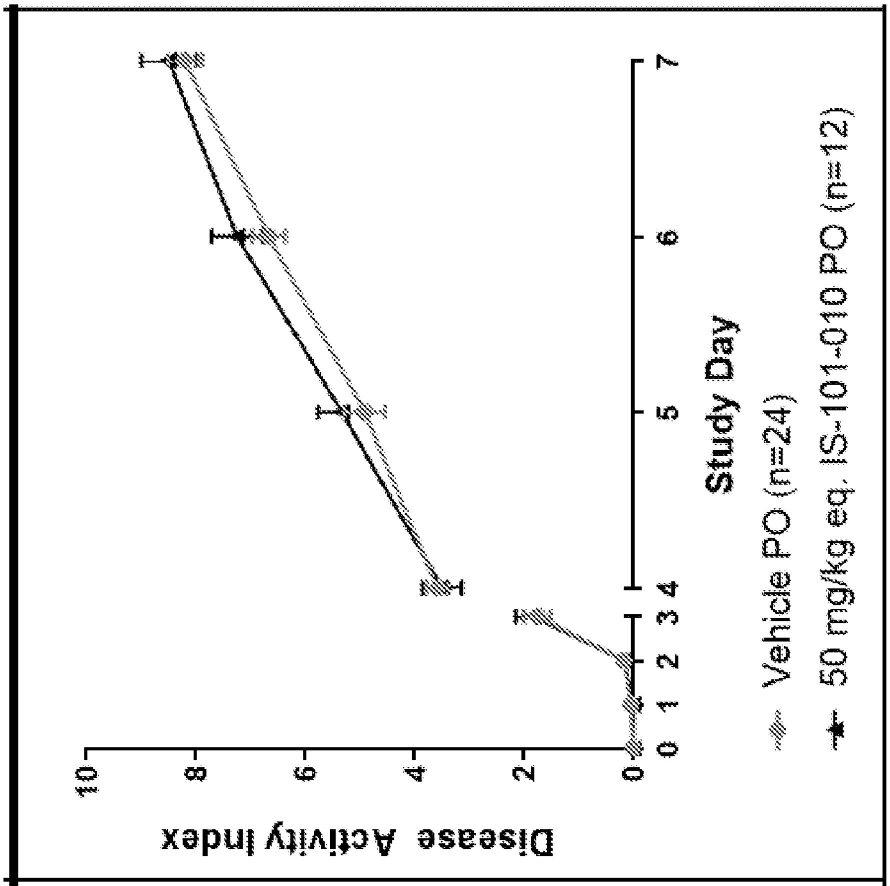
Figure 1E:
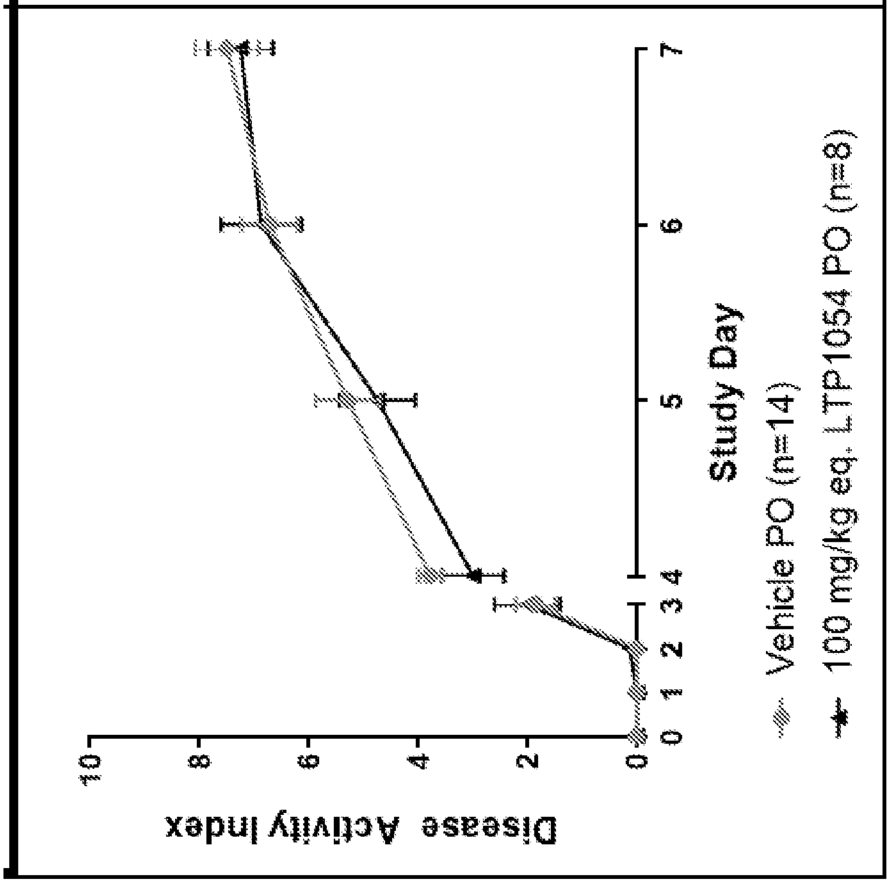
Figure 1G:
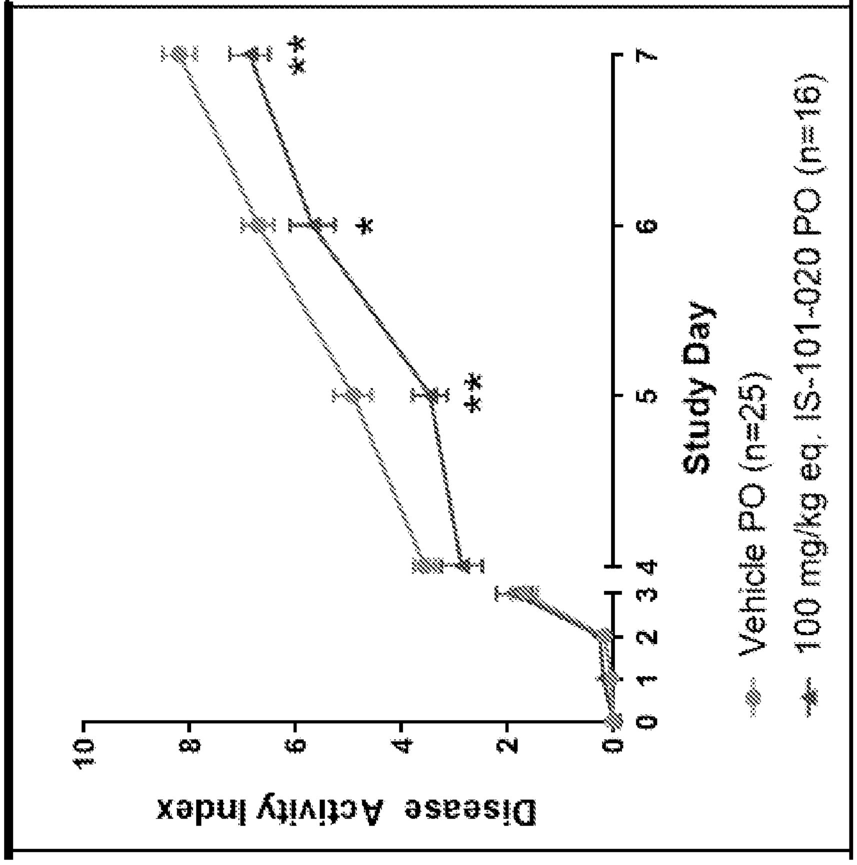
Figure 1H:
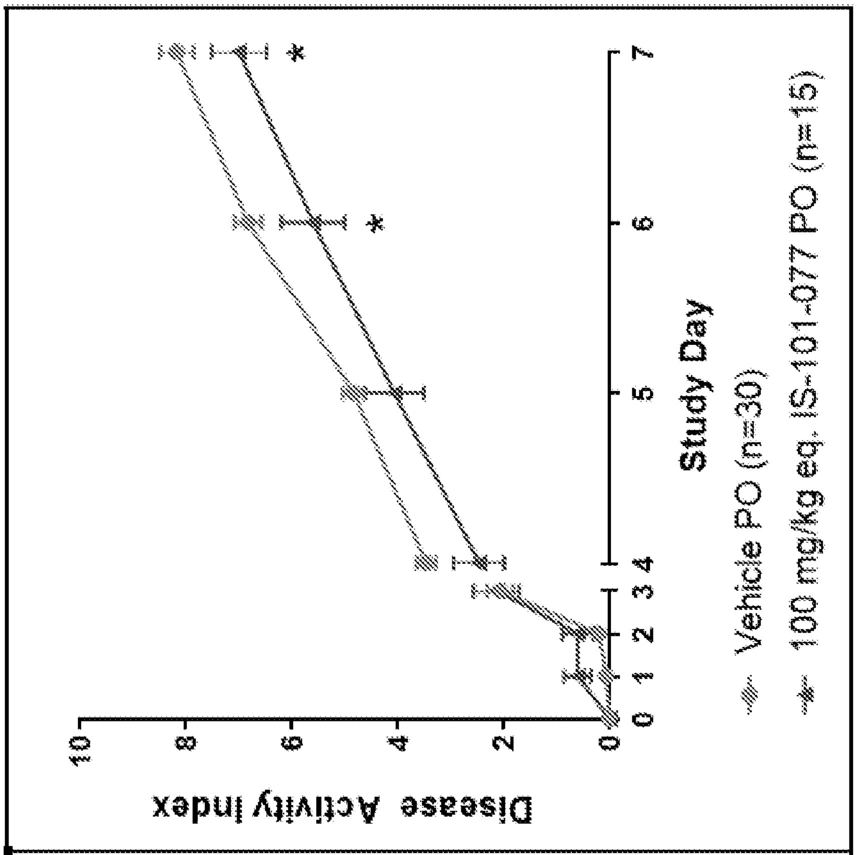

Test articles evaluated in the DSS-colitis model included LTP582 (#1), LTP592 (#2), LTP588 (#3), LTP1054 (#4), IS-101-010 (#8), IS-101-020 (#9) and IS-101-077 (#10). The concentrations evaluated were based upon the known efficacy of parent compound 2-PMPA in this model system and solubility of test articles; final concentrations tested ranged from 10 mg/kg to 100 mg/kg 2-PMPA molar equivalent dose. Test articles LTP592 (#2; FIG. 1B, FIG. 1D), IS-101-020 (#9; FIG. 1G) and IS-101-077 (#10; FIG. 1H) displayed selective anti-IBD efficacy in the DSS colitis exhibiting significant reductions in DAI on Study Days 6 and 7. Test articles LTP582 (#1; FIG. 1A), LTP588 (#3; FIG. 1C), LTP1054 (#4; FIG. 1E) and IS-101-010 (#8, FIG. 1F) were inactive in this model.

2.3 GCPII Enzymatic Activity in Murine Colon Tissue

A 5-mm length location-matched segment of proximal colon was harvested and flash-frozen following euthanasia on study day 6 of DSS-induced colitis, 4-hours after the final dose with vehicle or compound. Glutamate carboxypeptidase activity was measured using a radioenzymatic assay that was optimized and described previously. Rojas et al., 2002; Robinson et al., 1987.

2.4 Isolation of Colonic Lamina Propria Mononuclear Cells (LPMCs) and Flow Cytometry.

On DSS study day 5, a subset of mice (n=8-9/group) were euthanized and colons were processed for flow cytometry. Specifically, the distal 3 cm of colon was separated, mesenteric fat dissected away and intestinal contents removed. Then colon was transected longitudinally, washed with PBS, and minced thoroughly. Minced colon tissues were transferred into 5 ml HBSS with 10 mM HEPES containing 5% FBS and 0.2 mg/ml collagenase D (Sigma). Tissues were digested at 37° C. for 20 min with constant agitation (250 r.p.m.), then vigorously vortexed for 20 s. The resulting cell suspension containing LPMCs was filtered through a 70-μm nylon cell strainer and washed with 10 ml PBS. LPMC cell suspensions were pellets by centrifugation at 500 g for 10 min at 4° C., followed by resuspension in 8 ml 44% Percoll (GE healthcare, #57-0891-01) and overlaid over 5 ml of 67% Percoll. Gradients were centrifuged at 500 g for 20 min at 4° C. and cells at the interface were collected and washed with 10 ml PBS. Cells were transferred to 1.5 ml low-bind tube and stained for flow cytometric analysis. Immune cells were identified using previously reported markers, Nedelcovych et al., 2019; Baldwin et al., 2015, including: Total WBCs (CD11b+), Neutrophils (CD11b+Ly6G+), Monocytes (CD45+CD11b+Ly6ChiMHCII-CX3CR1lo) and transitioning monocytes (CD11b+Ly6ChiMHCII+).

Example 3

Pharmacokinetic Evaluation 3.1 Pharmacokinetic Evaluation in Beagle Dogs

Dog pharmacokinetic studies were conducted in accordance with the guidelines recommended in the Guide for the Care and Use of Laboratory Animals and were approved by the Charles River Labs (Wilmington, MA) Institutional Animal Care and Use Committee. LTP-592 was administered orally at three dose levels of 1.67, 5.00, and 16.67 mg/kg equivalent. In addition LTP-592 (5 mg/kg) also were administered via IV route for bioavailability determination. Blood samples were collected from the jugular vein (approximately 1 mL) via direct vein puncture at specified time points (0.083-24 h) post dose and placed into sodium heparin tubes. Blood samples were centrifuged at 2000 g for 15 min at 4° C. Plasma samples were collected in tubes and stored at −80° C. until bioanalysis.

3.2 Pharmacokinetic Evaluation in Mice

All pharmacokinetic studies in mice were conducted according to protocols approved by the Animal Care and Use Committee at Johns Hopkins University. Male CD-1 mice between 25 and 30 g were obtained from Harlan and maintained on a 12 h light-dark cycle with ad libitum access to food and water. In vivo pharmacokinetic evaluation of LTP-592 was conducted following oral and IV administration at three dose levels of 10, 30, and 100 mg/kg equivalent. The mice were sacrificed at specified time points (0.083-24 h) post drug administration. For the collection of plasma and colon, animals were euthanized with $CO_2$, and blood samples were collected in heparinized microtubes by cardiac puncture. Colon samples were dissected and immediately flashfrozen (−80° C.). Blood samples were spun at 2000 g for 15 min, and plasma was removed and stored at −80° C. until LC-MS/MS analysis.

3.3 Results

Concentration-time profiles for LTP-592 at various doses in plasma are shown in FIG. 6A and FIG. 6B, respectively. Following IV administration, LTP-592 delivered peak plasma concentrations ($C_{max}$) of 31.7 nmol/mL at 5 min post dose ($T_{max}$), with total exposures ($AUC_{0-t}$) of 9.9 h*nmol/mL. All dogs showed low levels of intact LTP-592 following PO administration with the absolute oral bioavailability≤1% (FIG. 6).

Concentration-time profile for intact LTP-592 and the respective pharmacokinetic parameters in plasma and colon of mice are shown in FIG. 7A, FIG. 7B, and FIG. 7C. In mice, following IV administration, LTP-592 delivered peak plasma concentrations ($C_{max}$) of 0.59 nmol/mL at 5 min post dose ($T_{max}$), with total exposures ($AUC_{0-t}$) of 0.53 h*nmol/mL. At all dose levels except 100 mg/kg intact LTP-592 levels in plasma were below the limit of quantification of 30 nM (FIG. 7A). In contrast, in colon, high exposures of LTP-592 (20.5-80.8 h*nmol/mL; FIG. 7B and FIG. 7C) were observed following oral administration suggesting restricted gastrointestinal delivery. Thus, in both mice and dogs we confirmed low oral bioavailability and gut restricted delivery of LTP-592 following oral administration, the intended route for clinical translation.

Example 4

Off-Target Safety Screen of LTP-592

Eurofins SafetyScreen44™ was conducted to evaluate off target interaction of LTP-592 (10 μM). LTP-592 did not show significant interaction with any targets at (Table 1).

| ASSAY NUMBER | ASSAY NAME | MEASUREMENT | VALUE |
|---|---|---|---|
| 439 | 5-HT transporter (h) (antagonist radioligand) | Mean % Inhibition | −1.17E+00 |
| 131 | 5-HT1A (h) (agonist radioligand) | Mean % Inhibition | −1.20E+01 |
| 4376 | 5-HT1B (h) (antagonist radioligand) | Mean % Inhibition | −2.55E+01 |
| 471 | 5-HT2A (h) (agonist radioligand) | Mean % Inhibition | −2.15E+01 |
| 1333 | 5-HT2B (h) (agonist radioligand) | Mean % Inhibition | −3.90E+01 |
| 411 | 5-HT3 (h) (antagonist radioligand) | Mean % Inhibition | −1.12E+01 |
| 4 | A2A (h) (agonist radioligand) | Mean % Inhibition | −1.45E+01 |
| 363 | acetylcholinesterase (h) | Mean % Inhibition | −9.01E−01 |
| 2338 | alpha 1A (h) (antagonist radioligand) | Mean % Inhibition | −4.63E+00 |
| 13 | alpha 2A (h) (antagonist radioligand) | Mean % Inhibition | 11.3122 |
| 933 | AR(h) (agonist radioligand) | Mean % Inhibition | −8.12E+00 |
| 18 | beta 1 (h) (agonist radioligand) | Mean % Inhibition | −1.02E+00 |
| 20 | beta 2 (h) (antagonist radioligand) | Mean % Inhibition | −5.79E+00 |
| 28 | BZD (central) (agonist radioligand) | Mean % Inhibition | 4.35277 |
| 161 | Ca2+ channel (L, dihydropyridine site) (antagonist radioligand) | Mean % Inhibition | 7.10864 |
| 4708 | CB1 (h) (agonist radioligand) | Mean % Inhibition | −8.38E+00 |
| 37 | CB2 (h) (agonist radioligand) | Mean % Inhibition | −5.38E+00 |
| 39 | CCK1 (CCKA) (h) (agonist radioligand) | Mean % Inhibition | −3.82E+01 |
| 4173 | COX1(h) | Mean % Inhibition | 14.0408 |
| 4186 | COX2(h) | Mean % Inhibition | 11.3876 |
| 44 | D1 (h) (antagonist radioligand) | Mean % Inhibition | −2.03E+01 |
| 1322 | D2S (h) (agonist radioligand) | Mean % Inhibition | −4.70E+00 |
| 114 | delta (DOP) (h) (agonist radioligand) | Mean % Inhibition | 21.5416 |
| 52 | dopamine transporter (h) (antagonist radioligand) | Mean % Inhibition | −8.59E−01 |
| 54 | ETA (h) (agonist radioligand) | Mean % Inhibition | −4.11E+00 |
| 469 | GR (h) (agonist radioligand) | Mean % Inhibition | 11.1756 |
| 870 | H1 (h) (antagonist radioligand) | Mean % Inhibition | 4.91892 |
| 1208 | H2 (h) (antagonist radioligand) | Mean % Inhibition | −3.23E+00 |
| 4461 | kappa (h) (KOP) (agonist radioligand) | Mean % Inhibition | 1.14318 |
| 166 | KV channel (antagonist radioligand) | Mean % Inhibition | 1.61725 |
| 2906 | Lck kinase (h) | Mean % Inhibition | −1.05E+01 |
| 91 | M1 (h) (antagonist radioligand) | Mean % Inhibition | 1.20755 |
| 93 | M2 (h) (antagonist radioligand) | Mean % Inhibition | −1.44E+00 |
| 95 | M3 (h) (antagonist radioligand) | Mean % Inhibition | −1.56E+00 |
| 443 | MAO-A (antagonist radioligand) | Mean % Inhibition | 0.18432 |
| 118 | mu (MOP) (h) (agonist radioligand) | Mean % Inhibition | −4.55E+00 |
| 3029 | N neuronal alpha 4beta 2 (h) (agonist radioligand) | Mean % Inhibition | −7.42E+00 |
| 169 | Na+ channel (site 2) (antagonist radioligand) | Mean % Inhibition | −9.71E+00 |
| 66 | NMDA (antagonist radioligand) | Mean % Inhibition | 7.24414 |
| 355 | norepinephrine transporter (h) (antagonist radioligand) | Mean % Inhibition | 9.59389 |
| 4072 | PDE3A (h) | Mean % Inhibition | 19.1337 |
| 4077 | PDE4D2 (h) | Mean % Inhibition | 7.77619 |
| 4094 | Potassium Channel hERG (human)-[3H] Dofetilide | Mean % Inhibition | 4.72558 |
| 159 | V1a (h) (agonist radioligand) | Mean % Inhibition | −1.96E+00 |

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Rais, R.; Jiang, W.; Zhai, H.; Wozniak, K. M.; Stathis, M.; Hollinger, K. R.; Thomas, A. G.; Rojas, C.; Vomov, J. J.; Marohn, M.; Li, X.; Slusher, B. S., FOLH1/GCPII is elevated in IBD patients, and its inhibition ameliorates murine IBD abnormalities. *JCI Insight* 2016, 1 (12).

Sipka, S.; Bruckner, G., The immunomodulatory role of bile acids. *Int Arch Allergy Immunol* 2014, 165 (1), 1-8.

Calmus, Y.; Poupon, R., Shaping macrophages function and innate immunity by bile acids: mechanisms and implication in cholestatic liver diseases. *Clin Res Hepatol Gastroenterol* 2014, 38 (5), 550-6.

Colombel, J. F.; Sandborn, W. J.; Rutgeerts, P.; Enns, R.; Hanauer, S. B.; Panaccione, R.; Schreiber, S.; Byczkowski, D.; Li, J.; Kent, J. D.; Pollack, P. F., Adalimumab for maintenance of clinical response and remission in patients with Crohn's disease: the CHARM trial. *Gastroenterology* 2007, 132:52-65.

Hamilton, M. J.; Snapper, S. B.; Blumberg, R. S., Update on biologic pathways in inflammatory bowel disease and their therapeutic relevance. *J. Gastroenterol.* 2012, 47: 1-8.

Hanauer, S. B.; Feagan, B. G.; Lichtenstein, G. R.; Mayer, L. F.; Schreiber, S.; Colombel, J. F.; Rachmilewitz, D.; Wolf, D. C.; Olson, A.; Bao, W.; Rutgeerts, P., Maintenance infliximab for Crohn's disease: the ACCENT I randomised trial. *Lancet* 2002, 359: 1541-1549.

Ho, P. P.; Steinman, L., Obeticholic acid, a synthetic bile acid agonist of the farnesoid X receptor, attenuates experimental autoimmune encephalomyelitis. *Proc Natl Acad Sci USA* 2016, 113 (6), 1600-5.

Kaser, A.; Zeissig, S.; Blumberg, R. S., Inflammatory bowel disease. *Annu. Rev. Immunol.* 2010, 28:573-621.

Kozuch, P. L. and Hanauer, S. B., Treatment of inflammatory bowel disease: A review of medical therapy. World *J. Gastroenterol.* 2008, 14:354-377.

Laukens, D.; Devisscher, L.; Van den Bossche, L.; Hindryckx, P.; Vandenbroucke, R. E.; Vandewynckel, Y. P.; Cuvelier, C.; Brinkman, B. M.; Libert, C.; Vandenabeele, P.; De Vos, M., Tauroursodeoxycholic acid inhibits experimental colitis by preventing early intestinal epithelial cell death. *Lab Invest* 2014, 94 (12), 1419-30.

Lawrance, I. C. What is left when anti-tumour necrosis factor therapy in inflammatory bowel diseases fails? *World J. Gastroenterol.* 2014, 20: 1248-1258.

Regueiro, M.; Siemanowski, B.; Kip, K. E.; Plevy, S., Infliximab dose intensification in Crohn's disease. *Inflamm. Bowel Dis.* 2007, 13: 1093-1099.

Sartor, R. B., Mechanisms of disease: pathogenesis of Crohn's disease and ulcerative colitis. *Nat. Clin. Pract. Gastroenterol. Hepatol.* 2006, 3:390-407.

Schmidt, C; Giese, T.; Hermann, E.; Zeuzem, S.; Meuer, S. C.; Stallmach, A., Predictive value of mucosal TNF-alpha transcripts in steroid-refractory Crohn's disease patients receiving intensive immunosuppressive therapy. *Inflamm. Bowel Dis.* 2007, 13:65-70.

Schreiber, S.; Khaliq-Kareemi, M.; Lawrance, I. C.; Thomsen, O. O.; Hanauer, S. B.; McColm, J.; Bloomfield, R.; Sandborn, W. J., Maintenance therapy with certolizumab pegol for Crohn's disease. *N. Engl. J. Med.* 2007, 357: 239-250.

Strober, W.; Fuss, I.; and Mannon, P., The fundamental basis of inflammatory bowel disease. *J. Clin. Invest.* 2007, 1 17:514-521.

Xavier, R. J. and Podolsky, D. K., Unravelling the pathogenesis of inflammatory bowel disease. *Nature* 2007, 448:427-434.

Van, A. G.; Van, R. M.; Sciot, R.; Dubois, B.; Vermeire, S.; Noman, M.; Verbeeck, J.; Geboes, K.; Robberecht, W.; Rutgeerts, P., Progressive multifocal leukoencephalopathy after natalizumab therapy for Crohn's disease. *N. Engl. J. Med.* 2005, 353:362-368.

Rojas, C.; Frazier, S. T.; Flanary, J.; Slusher, B. S., Kinetics and inhibition of glutamate carboxypeptidase II using a microplate assay. *Anal Biochem* 2002, 310 (1), 50-4.

Robinson, M. B.; Blakely, R. D.; Couto, R.; Coyle, J. T., Hydrolysis of the brain dipeptide N-acetyl-L-aspartyl-L-glutamate. Identification and characterization of a novel N-acetylated alpha-linked acidic dipeptidase activity from rat brain. *J Biol Chem* 1987, 262(30), 14498-506.

Nedelcovych, M. T.; Kim, B. H.; Zhu, X.; Lovell, L. E.; Manning, A. A.; Kelschenbach, J.; Hadas, E.; Chao, W.; Prchalova, E.; Dash, R. P.; Wu, Y.; Alt, J.; Thomas, A. G.; Rais, R.; Kamiya, A.; Volsky, D. J.; Slusher, B. S., Glutamine Antagonist JHU083 Normalizes Aberrant Glutamate Production and Cognitive Deficits in the EcoHIV Murine Model of HIV-Associated Neurocognitive Disorders. *Journal of neuroimmune pharmacology: the official journal of the Society on NeuroImmune Pharmacology* 2019.

Baldwin, K. T.; Carbajal, K. S.; Segal, B. M.; Giger, R. J., Neuroinflammation triggered by beta-glucan/dectin-1 signaling enables CNS axon regeneration. *Proceedings of the National Academy of Sciences of the United States of America* 2015, 112 (8), 2581-6.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound selected from the group consisting of:

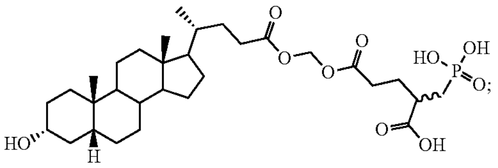

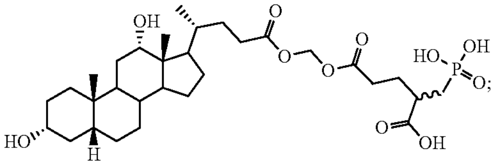

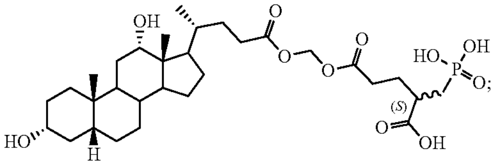

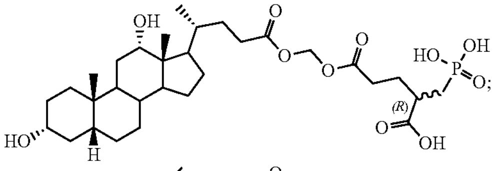

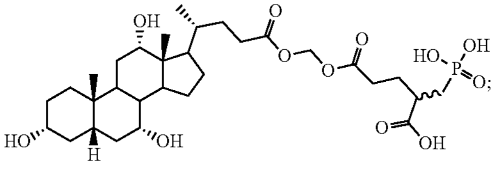

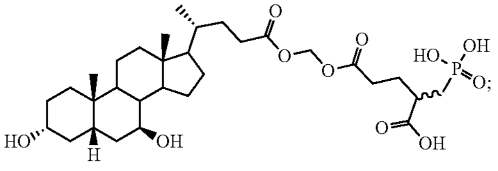

-continued

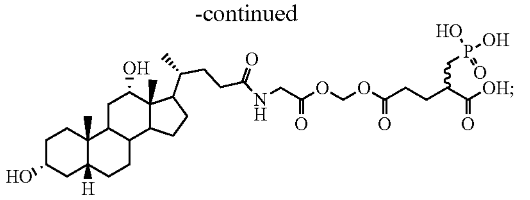

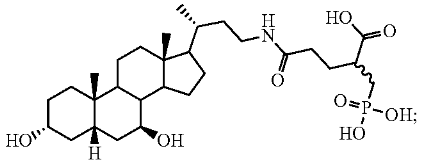

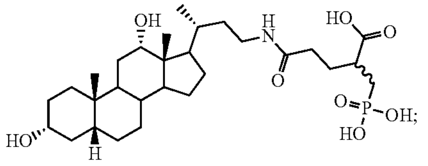

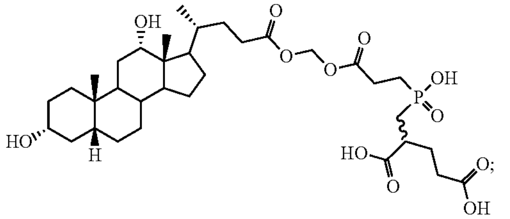

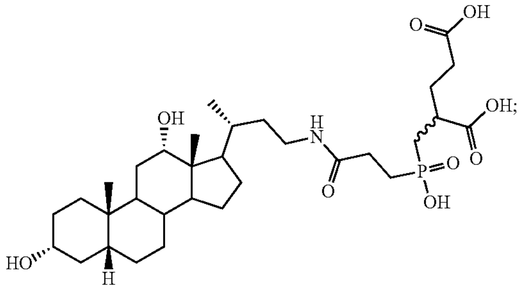

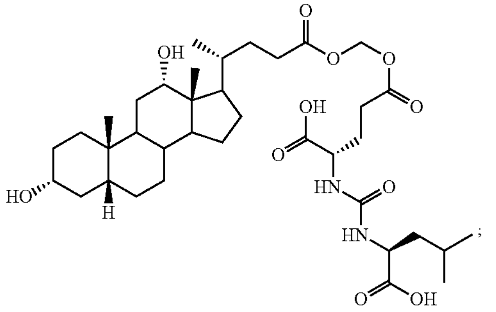

-continued

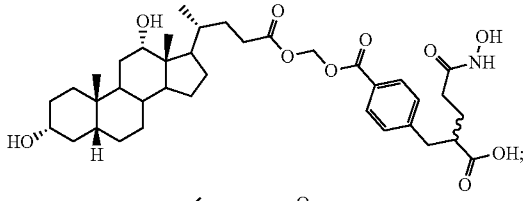

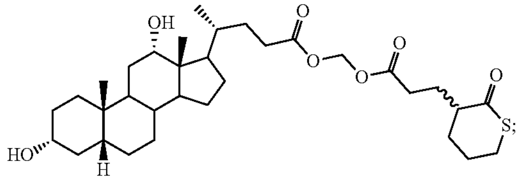

and

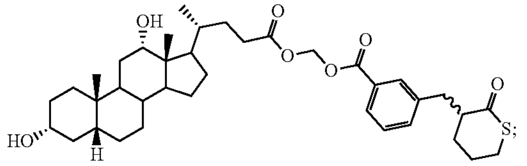

and pharmaceutically acceptable salts thereof.

2. A method for treating a disease or condition associated with an elevated GCPII activity in a subject in need of treatment thereof, the method comprising administering to the subject a therapeutically effective amount of a compound of claim 1 or a pharmaceutically acceptable salt thereof wherein the disease or condition associated with an elevated GCPII activity is an inflammatory bowel disease.

3. The method of claim 2, wherein the inflammatory bowel disease is selected from the group consisting of Crohn's disease (CD) and ulcerative colitis (UC).

4. The method of claim 2, wherein the method for treating a disease or condition associated with an elevated GCPII activity inhibits GCPII activity in the subject.

5. A pharmaceutical composition, comprising at least one compound of claim 1, in admixture with a pharmaceutically acceptable excipient.

6. The pharmaceutical composition of claim 5, further comprising one or more additional therapeutic agents.

* * * * *